(12) United States Patent
Plettenburg et al.

(10) Patent No.: US 8,710,077 B2
(45) Date of Patent: Apr. 29, 2014

(54) CYCLOALKYLAMINE SUBSTITUTED ISOQUINOLINE AND ISOQUINOLINONE DERIVATIVES

(75) Inventors: Oliver Plettenburg, Frankfurt am Main (DE); Katrin Lorenz, Frankfurt am Main (DE); Jochen Goerlitzer, Frankfurt am Main (DE); Matthias Löhn, Frankfurt am Main (DE); Sandrine Biscarrat, Paris (FR); Fréderic Jeannot, Paris (FR); Olivier Duclos, Paris (FR)

(73) Assignee: Sanofi, Paris (FR)

( * ) Notice: Subject to any disclaimer, the term of this patent is extended or adjusted under 35 U.S.C. 154(b) by 759 days.

(21) Appl. No.: 12/487,503

(22) Filed: Jun. 18, 2009

(65) Prior Publication Data

US 2010/0056553 A1 Mar. 4, 2010

Related U.S. Application Data

(63) Continuation of application No. PCT/EP2007/011169, filed on Dec. 19, 2007.

(30) Foreign Application Priority Data

Dec. 27, 2006 (EP) .................................. 06026897

(51) Int. Cl.
*A61K 31/47* (2006.01)
*C07D 217/00* (2006.01)

(52) U.S. Cl.
USPC .......................................... 514/309; 546/139

(58) Field of Classification Search
None
See application file for complete search history.

(56) References Cited

U.S. PATENT DOCUMENTS

| | | | |
|---|---|---|---|
| 5,480,883 A | 1/1996 | Spada et al. | |
| 6,903,107 B1 | 6/2005 | Timmers et al. | |
| 7,217,722 B2 | 5/2007 | Takami et al. | |
| 7,618,985 B2 | 11/2009 | Ray et al. | |
| 2003/0220368 A1 | 11/2003 | Ozaki et al. | |
| 2004/0138286 A1 | 7/2004 | Imazaki et al. | |
| 2006/0079556 A1 | 4/2006 | Sher et al. | |
| 2007/0060595 A1 | 3/2007 | Yoshizawa et al. | |
| 2008/0045566 A1 | 2/2008 | Ray et al. | |

FOREIGN PATENT DOCUMENTS

| | | |
|---|---|---|
| EP | 1403255 | 3/2004 |
| EP | 1541559 | 6/2005 |
| EP | 1550660 | 7/2005 |
| FR | 2485537 | 6/1980 |
| JP | 10087629 | 4/1998 |
| WO | 9202476 | 2/1992 |
| WO | 9706802 | 2/1997 |
| WO | 9723214 | 7/1997 |
| WO | WO 98/06433 | 2/1998 |
| WO | 9911642 | 3/1999 |
| WO | 0024718 | 5/2000 |
| WO | 0073299 | 12/2000 |
| WO | WO 01/39726 | 6/2001 |
| WO | 0153288 | 7/2001 |
| WO | 0156988 | 8/2001 |
| WO | 0164656 | 9/2001 |
| WO | WO 01/64238 | 9/2001 |
| WO | 0177101 | 10/2001 |
| WO | 0192227 | 12/2001 |
| WO | 0234712 | 5/2002 |
| WO | 02055496 | 7/2002 |
| WO | 02076457 | 10/2002 |
| WO | 02088101 | 11/2002 |
| WO | 03018556 | 3/2003 |
| WO | 03024450 | 3/2003 |
| WO | WO 03/053330 | 7/2003 |
| WO | 2004113297 | 12/2004 |
| WO | WO 2004/106325 | 12/2004 |
| WO | 2005035933 | 2/2005 |
| WO | 2005035516 | 4/2005 |
| WO | WO 2005/030130 | 4/2005 |
| WO | WO 2005/030791 | 4/2005 |
| WO | 2005054202 | 6/2005 |
| WO | 2005074535 | 8/2005 |
| WO | 2005087226 | 9/2005 |
| WO | 2005095362 | 10/2005 |
| WO | 2007012421 A1 | 2/2007 |
| WO | 2007012422 A1 | 2/2007 |
| WO | WO 2007/012422 | 2/2007 |
| WO | 2007039563 A1 | 4/2007 |
| WO | WO 2007/065916 | 6/2007 |

(Continued)

OTHER PUBLICATIONS

U.S. Appl. No. 11/961,193, filed Dec. 20, 2007, Plettenburg, et. al.
U.S. Appl. No. 12/019,866, filed Jan. 25, 2008, Plettenburg, et. al.
U.S. Appl. No. 12/019,799, filed Jan. 25, 2008, Plettenburg, et. al.
U.S. Appl. No. 12/487,479, filed Jun. 18, 2009, Plettenburg, et. al.
U.S. Appl. No. 12/487,455, filed Jun. 18, 2009, Plettenburg, et. al.

(Continued)

*Primary Examiner* — Heidi Reese
(74) *Attorney, Agent, or Firm* — Scully, Scott, Murphy & Presser, P.C.

(57) ABSTRACT

The invention relates to 6-substituted isoquinoline and isoquinolinone derivatives of the formula (I)

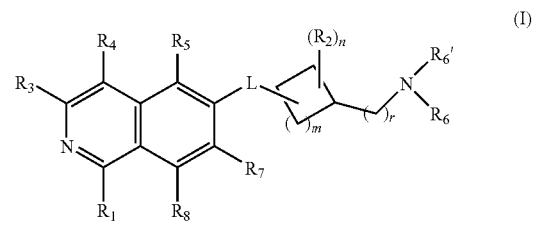

useful for the treatment and/or prevention of diseases associated with Rho-kinase and/or Rho-kinase mediated phosphorylation of myosin light chain phosphatase, and compositions containing such compounds.

47 Claims, No Drawings

(56) References Cited

FOREIGN PATENT DOCUMENTS

| WO | WO 2008/020081 | 2/2008 |
|---|---|---|
| WO | 2008077555 A2 | 7/2008 |
| WO | 2008077556 A1 | 7/2008 |

OTHER PUBLICATIONS

U.S. Appl. No. 12/487,525, filed Jun. 18, 2009, Plettenburg, et. al.
U.S. Appl. No. 12/487,386, filed Jun. 18, 2009, Plettenburg, et. al.
U.S. Appl. No. 12/487,409, filed Jun. 18, 2009, Plettenburg, et. al.
U.S. Appl. No. 12/487,403, filed Jun. 18, 2009, Plettenburg, et. al.
Al, S., et. al., Rho-Rho Kinase Is involved in Smooth Muscle Cell Migration Through Myosin Light Chain Phosphorylation-Dependent and Independent Pathways, Atherosclerosis, vol. 155, pp. 321-327, (2001).
Amano, M., et. al., Formation of Actin Stress Fibers and Focal Adhesions Enhanced by Rho-Kinase, Science, vol. 275, pp. 1308-1311, (1997).
Bauer, M., et. al., Dichotomous Regulation of Myosin Phosphorylation and Shape Change by Rho-Kinase and Calcium in Intact Human Platelets, Blood, vol. 94, No. 5, (1999), pp. 1665-1672.
Chellaiah, M., et. al.,, Rho-Dependent Rho Kinase Activation increases CD44 Surface Expression and Bone Resorption in Osteoclasts, The Journal of Biological Chemistry, vol. 278, No. 31, (2003), pp. 29086-29097.
Chitaley, K., et. al., Antagonism of Rho-Kinase Stimualates Rat Penile Erection Via a Nitric Oxide-Independent Pathway, Nature Medicine, vol. 7, No. 1, (2001), pp. 119-122.
Demiryurek, S., et. al., Effects of Fasudil, a Rho-Kinase Inhibitor, On Myocardial Preconditioning in Anesthetized Rats, European Journal of Pharmacology, vol. 527, (2005), pp. 129-140.
Fukumoto, Y., et. al., Acute Vasodilator Effects of a Rho-Kinase Inhibitor, Fasudil, in Pateients With Severe Pulmonary Hybertension, Heart, (2005), vol. 91, pp. 391-392.
Furukawa, N.. et, al., Role of Rho-Kinase in Regulation of Insulin Action and Glucose Homeostasis, Cell Metabolism, vol. 2, pp. 119-129, (2005).
Gingras, D., et. al., Tyrosine Phosphorylation of the Vascular Endothelial-Growth-Factor Receptor-2 (VEGFR-2) is Modulated by Rho Proteins, Biochem. J., (2000), vol. 348, pp. 273-280.
Gokina, N. I., et. al., Effects of Rho Kinase Inhibition on Cerebral Artery Myogenic Tone and Reactivity, J. Appl. Physiol. vol. 98, pp. 1940-1948, (2005).
Hara, M., et. al., Protein Kinase inhibition by Fasudil Hydrochloride Promotes Neurological Recovery After Spinal Cord Injury in Rats, J Neurosurg. (Spine 1), vol. 93, pp. 94-101, (2000).
Hattori, T., et al., Long-Term Inhibition of Rho-Kinase Suppresses Left Ventricular Remodeling After Myocardial Infarction in Mice, Circulation, (2004), vol. 109, pp. 2234-2239.
Okada, H., et. al., Synthesis and Antitumor Activities of Prodrugs of Benzoylphenylureas, Chem. Pharm. Bull (1994), pp. 57-61, vol. 42, No. 1.
Hitomi, A., et. al., Hemorheological Abnormalities in Experimental Cerebral Ischemia and Effects of Protein Kinase Inhibitor on Blood Fluidity, Life Sciences, vol. 67, (2000), pp. 1929-1939.
Honjo, M., et. al., Effects of Rho-Associated Protein Kinase Inhibitors Y-27632 on Intraocular Pressure and Outflow Facitlity, Investigative Ophthalmology & Visual Science, (2001), vol. 42. No. 1, pp. 137-144.
Inoue, M., et. al., Initiation of Neuropathic Pain Requires Lysophospatidic Acid Receptor Signaling, Nature Medicine, vol. 10, No. 7, pp. 712-718, (2004).
Itoh, et. al., An Essential Part for Rho-Associated Kinase in the Transcellular Invasion of Tumor Cells, Nature Medicine, vol. 5, No. 2, pp. 221-225, (1999).
Kawaguchi, A., et. al., The Effect of a Rho Kinase Inhibitor Y-27632 on Superoxide Production, Aggregation and Adhesion in Human Polymorphonuclear Leukocytes, European Journal of Pharmacology, vol. 403, (2000), pp. 203-208.
Kim, I., et. al., Thin and Thick Filament Regulation of Contractility in Experiments Cerebral Vasospasm, Neurosurgery, vol. 46, No. 2, (2000), pp. 440-447.
Kimura, K., et. al., Regulation of the Association of Adducin With Actin Filaments by Rho-Associated Kinase (Rho-Kinase) and Myosin Phosphatase, The Journal of Biological Chemistry, vol. 273, No. 10, pp. 5542-5548, (1998).
Kishi, T., et. al., Rho-Kinase inhibitor Improves Increased Vascular Resistance and Impaired Vasodilation of the Forearm in Patients With Heart Failure, Circulation, (2005), vol. 111, pp. 2741-2747.
Klages, B., et. al., Activation of G12/G13 Results in Shape Change and Rho/Rho-Kinase-Mediated Myosin Light Chain Phosphorylation in Mouse Platelets. The Journal of Cell Biology, vol. 144, No. 4. (1999), pp. 745-754.
Lin, T., et. al,, Rho-ROCK-LIMK-Cofilin Pathway Regulates Shear Stress Activation of Sterol Regulatory Element Binding Proteins, Circulation Research, (2003), vol. 92, pp. 1296-1304.
Maruoka, S., et. al., Elastase Anti-Elastase Imbalance in the Pathogenesis of COPD, Nippon Rinsho, (1999), vol. 57, pp. 1982-1987.
Masumoto, A. et. al., Suppression of Coronary Artery Spasm by the Rho-Kinase Inhibitor Fasudil in Patients With Vasospastic Angina, Circulation, (2002), vol. 105, pp. 1545-1547.
Nakahara, T., et. al., Y-27632 Potentiates Relaxant Effects of B2 Adrenoceptor Agonists in Bovine Tracheal Smooth Muscle, European Journal of Pharmacology, vol. 389, (2000), pp. 103-106.
Negoro, N., et. al., The Kinase Inhibitor Fasudil (HA-1077) Reduces Intimal Hyperplasia through Inhibiting Migration and Enhancing Cell Loss of Vascular Smooth Muscle Cells, Biochemical and Biophysical Research Communications, vol. 262, pp. 211-215, (1999).
Noma, K., et. al., Physiological Role of ROCKS in the Cardiovascular System, Am. J. Physiol Cell Physiol , vol. 290, pp. C661-C668, (2006).
Pacaud, P., et. al., Rho Proteins and Vascular Diseases, Archives Des Maladies Du CCeur Et Des Vaisseaux, vol. 98, pp. 249-254, (2005).
Pommereau, A., et. al., Two Simple and Generic Antibody-Independent Kinase Assays: Comparison of a Bioluminescent and a Microfluidic Assay Format, J. Biomol. Screen, (2004), vol. 9, pp. 409-416.
Retzer, M., et. al., Lysophosphatidic Acid-Induced Platelet Shape Change Proceeds Via Rho/Rho Kinase-Mediated Myosin Light-Chain and Moesin Phosphorylation, Cellular Signalling, vol. 12, pp. 645-648, (2000).
Retzer, M., et. al, Mildly Oxidised Low Density Lipoprotein Induces Platelet Shape Change Via Rho-Kinase-Dependent Phosphorylation of Myosin Light Chain and Moesin. FEBS Letters, vol. 466, pp. 70-74. (2000).
Sandu, O. A., et. al., Diabetes in the Goto-Kakizaki Rat Is Accompanied by Impaired Insulin-Mediated Myosin-Bound Phosphatase Activation and Vascular Smooth Muscle Cell Relaxation, Diabetes, vol. 49, (2000), pp. 2178-2189.
Sato, M., et. al., Involvement of Rho-Kinase-Mediated Phosphorylation of Myosin Light Chain in Enhancement of Cereberal Vasospasm, Circulation Research, (2000), vol. 87, pp. 195-200.
Satoh, S.-I., et. al., Pharmacological Profile of Hydroxy Fasudil as a Selective Rho Kinase Inhitor on Ischemic Brain Damage, Life Sciences, vol. 69, (2001), pp. 1441-1453.
Seasholtz, T. M., et. el., Rho and Rho Kinase Mediate Thrombin-Stimulated Vascular Smooth Muscle Cell DNA Synthesis and Migration , Circulation Research, (1999), vol. 84, pp. 1186-1193.
Setoguchi, H., et. al., Leukotriene C4 Enhances the Contraction of Porcine Tracheal Smooth Muscle Through the Activation of Y-27632, a Rho Kinase Inhibitor, Sensitive Pathway, British journal of Pharmacology, (2001), vol. 132, pp. 111-118.
Shimokawa, H., et. al., Anti-Anginal Effect of Fasudil, a Rho-Kthase Inhibitor, in Patients With Stable Effort Angina: A Multicenter Study, Journal of Cardiovascular Pharmacology, (2002)), vol. 40, pp. 751-761.
Somlyo, A. V., et. al., Rho-Kinase Inhibitor Retards Migration and In Vivo Dissemination of Human Prostate Cancer Cells, Biochemical and Biophysical Research Communications, vol. 269, pp. 652-659, (2000).

(56) References Cited

OTHER PUBLICATIONS

Steioff, K., et. al., Long Term Rho-Kinase Inhibition Ameliorates Endothelial Dysfunction in LDL-Receptor Deficient Mice, European Journal of Pharmacology, vol. 512, (2005), pp. 247-249.
Tatsumi, S., et. al., Involvement of Rho-Kinase in Inflammatory and Neuropathic Pain Through Phosphorylation of Myristoylated Alainine-Rich C-Kinase Substrate (MARCKS), Neuroscience, vol. 131, pp. 491-498, (2005).
Totsukawa, G., et. al., Distinct Roles of ROCK (Rho-Kinase) and MLCK in Spatial Regulation of MLC Phosphorylation for Assembly of Stress Fibers and Focal Adhesions in 3T3 Fibroblasts, The Journal of Cell Biology, vol. 150, No. 4, pp. 797-806, (2000).
Uchida, S., et. al., The Suppression of Small GTPase Rho Signal Transduction Pathway Inhibits Angiogenesis in Vitro and in Vivo, Biochemical and Biophysical Research Communications, vol. 269, pp. 633-640, (2000).
Uehata, M., et. al., Calcium Sensitization of Smooth Muscle Mediated by a Rho-Associated Protein Kinase in Hypertension, Nature, vol. 389, pp. 990-994, (1997).
Vicente-Manzanares, M., et. al., A Role for the Rho-p160 Rho Coiled-Coil Kinase Axis in the Chemokine Stromal Cell-Derived Factor-1a-Induced Lymphocyte Actomyosin and Microtubular Organization and Chemotaxis, The Journal of Immunology, (2002), vol. 168, pp. 400-410.
Vicente-Manzanares, M., et. al., The RhoA Effector MDia is Induced During T Cell Activation and Regulates Actin Polymerization and Cell Migration in T Lymphocytes, The Journal of Immunology, (2003), vol. 171, pp. 1023-1034.
Wakino, S., et. al., Rho/Rho Kinase as a Potential Target for the Treatment of Renal Disease, Drug News Perspective, (2005), vol. 18, pp. 639-643.
Yamakawa. T., et. al., Involvement of Rho-Kinase in Angiotensin II-Induced Hypertrophy of Rat Vascular, Smooth Muscle Cells, Hypertension, (2000), vol. 35, pp. 313-318.
Yamamoto, Y., et. al., The Protein Kinase Inhibitor Fasudil Protects Against Ischemic Myocardial Injury Induced by Endothelin-1 in the Rabbit, Journal of Cardiovascular Pharmacology, vol. 35, pp. 203-211, (2000).
Yoshida, Y., et. al., Studies on Anti-Helicobacter pylori Agents. Part 1: Benzyloxyisoquinoline Derivatives. Bioorg. & Med. Chem., vol. 7 (1999), pp. 2647-2666.
Yoshii, A., et. al., Relaxation of Contracted Rabbit Tracheal and Human Bronchial Smooth Muscle by Y-27632 Through Inhibition of Ca2+ Sensitization, Am. J. Resp. Cell Mol. Biol., vol. 20, pp. 1190-1200. (1999).
Zhou, Y., et. al., Nonsteroidal Anti-Inflammatory Drugs Can Lower Amyloidogenic AB42 by Inhibiting Rho, Science, vol 302, pp. 1215-1217, (2003).

Takami, et. al., Design and synthesis of rho kinase inhibitors, Bloorgehic & Medicinal Chem. 2004 (12) 9 pp. 2115-2137.
Iwakubo, M., et. al., Design and Synthesis of Rho Kinase inhibitors (III), Bloorgenic & Medicinal Chemistry, vol. 15, (2007), pp. 1022-1033.
Iwakubo, M., et. al., Design and Synthesis of Rho Kinase Inhibitors (II), Bioorganic & Medicinal Chemistry, vol. 15, (2007), pp. 350-364.
Alvarez, M. et al., "Product Class 5: Isoquinolines" Science of Synthesis (2005) pp. 661-838, vol. 15.
Alvarez, M. et al., "Product Class 6: Isoquinolines" Science of Synthesis (2005) pp. 839-890, vol. 15.
Remington's Pharmaceutical Sciences 17th Edition (1985), p. 1418.
Forzato, C. et al., "Baker's yeast reduction of 4-hetero-2-(2-nitroethyl)cyclohexanones" Tetrahedron: Asymmetry (1997) pp. 1811-1820, vol. 8.
U.S. Appl. No. 12/970,376, filed Dec. 16, 2010, Inventor: Plettenburg, et al, entitled: "6-Substituted Isoquinolines and Isoquinolinones".
U.S. Appl. No. 13/000,754, filed Apr. 20, 2011, Inventor: Plettenburg et al., entitled: "Substituted Isoquinolines and Isoquinolinones as Rho Kinase Inhibitors".
U.S. Appl. No. 13/000,202, filed Dec. 20, 2010, Inventor: Plettenburg et al., entitled: "Bi- and Polycyclic Substituted Isoquinoline and Isoquinolinone Derivatives".
Bonjoch, J. et al., "A New Synthetic Entry to the Tricyclic Skeleton of FR901483 by Palladium-Catalyzed Cyclization of Vinyl Bromides with Ketone Enolates" Tetrahedron Letters (2003) pp. 8387-8390, vol. 44.
Curran, T.T. et al., "The Preparation of Optically Active 2-Cyclopenten-1,4-Diol Derivatives from Furfuryl Alcohol" Tetrahedron, pp. 1983-2004, vol. 53(6).
Tamura, M. et al., "Development of Specific Rho-Kinase Inhibitors and Their Clinical Application" Biochimicia et Biophysica Acta (2005) pp. 245-252, vol. 1754.
Becker, D.P. et al., "A Short Synthesis of 1-Azaadamantan-4-one and the 4r and 4s Isomers of 4-Amino-1-azaadamantane" Synthesis (1992) pp. 1080-1082, vol. 11.
Degraffenreid, M.R. et al., "An Efficient and Scalable One-Pot Double Michael Addition-Dieckmann Condensation for the Synthesis of 4,4-Disubstituted Cyclohexane β-Keto Esters" Journal of Organic Chemistry (2007) pp. 7455-7458, vol. 72.
Lednicer, D. et al., "4-Amino-4-arylcyclohexanones and Their Derivatives, a Novel Class of Analgesics. 1. Modification of the Aryl Ring" Journal of Medicinal Chemistry (1980) pp. 424-430, vol. 23.
Caron, S. et al., "The Synthesis of a Selective PDE4/TNFα Inhibitor" Organic Process Research and Development (2001) pp. 587-592, vol. 5.

CYCLOALKYLAMINE SUBSTITUTED ISOQUINOLINE AND ISOQUINOLINONE DERIVATIVES

FIELD OF THE INVENTION

The present invention relates to novel isoquinoline and isoquinolinone derivatives as described in the claims, their preparation and their use in the treatment and/or prevention of diseases related to the inhibition of Rho-kinase and/or of Rho-kinase mediated phosphorylation of myosin light chain phosphatase.

BACKGROUND OF THE INVENTION

Activation of a small GTPase RhoA upon agonist stimulation results in conversion of RhoA from the inactive GDP-bound form to the active GTP-bound form with a subsequent binding to and activation of Rho-kinase. Two isoforms, Rho-kinase 1 and Rho-kinase 2, are known. Rho-kinase 2 is expressed in vascular smooth muscle cells and endothelial cells. Activation of Rho-kinase 2 by the active GTP-bound RhoA leads to calcium sensitization of smooth muscle cells through phosphorylation-mediated inhibition of the myosin light chain phosphatase activity and thereby up-regulation of the activity of myosin regulatory light chain (Uehata et al., Nature 1997, 389, 990-994).

It is known that Rho-kinase is involved in vasoconstriction, including the development of myogenic tone and smooth muscle hypercontractility (Gokina et al. J. Appl. Physiol. 2005, 98, 1940-8), bronchial smooth muscle contraction (Yoshii et al. Am. J. Resp. Cell Mol. Biol. 20, 1190-1200), asthma (Setoguchi et al. Br J Pharmacol. 2001, 132, 111-8; Nakahara, et al. Eur J 2000, 389, 103) and chronic obstructive pulmonary disease (COPD, Maruoka, Nippon Rinsho, 1999, 57, 1982-7), hypertension, pulmonary hypertension (Fukumoto et al. Heart, 91, 391-2, 2005, Mukai et al. Nature 1997, 389, 990-4) and ocular hypertension and regulation of intraocular pressure (Honjo et al. Invest. Opthalmol. Visual Sci. 2001, 42, 137-144), endothelial dysfunction (Steioff et al. Eur. J. Pharmacol. 2005, 512, 247-249), angina (Masumoto et al. Circ 2002, 105, 1545-47, Shimokawa et al. JCP, 2002, 40, 751-761), nephropathy, including hypertension-induced, non-hypertension-induced, and diabetic nephropathies, renal failure and peripheral arterial occlusive disease (PAOD) (Wakino et al. Drug News Perspect. 2005, 18, 639-43), myocardial infarction (Demiryurek et al. Eur J Pharmacol. 2005, 527, 129-40, Hattori et al. Circulation, 2004, 109, 2234-9), cardiac hypertrophy and failure (Yamakawa, et al. Hypertension 2000, 35, 313-318, Liao et al. Am J Physiol Cell Physiol. 2006, 290, C661-8, Kishi et al. Circ 2005, 111, 2741-2747), coronary heart disease, artherosclerosis, restenosis (Pacaud et al. Arch. Mal. Coeur 2005, 98, 249-254, Retzer, et al. FEBS Lett 2000, 466, 70, Negoro, et al. Biochem Biophys Res Commun 1999, 262, 211), diabetes, diabetic complications, glucose utilization and metabolic syndrome (Sandu, et al. Diabetes 2000, 49, 2178, Maeda et al. Cell Metab. 2005, 2, 119-29), sexual dysfunction, e.g., penile erectile dysfunction (Chitaley et al. Nature Medicine 2001, 7, 119-122), retinopathy, inflammation, immune diseases, AIDS, osteoporosis, endocrine dysfunctions, e.g. hyperaldosteronism, central nervous system disorders such as neuronal degeneration and spinal cord injury (Hara, et al. J Neurosurg 2000, 93, 94), cerebral ischemia (Uehata, et al. Nature 1997, 389, 990; Satoh et al. Life Sci. 2001, 69, 1441-53; Hitomi, et al. Life Sci 2000, 67, 1929; Yamamoto, et al. J Cardiovasc Pharmacol. 2000, 35, 203-11), cerebral vasospasm (Sato, et al. Circ Res 2000, 87, 195; Kim, et al. Neurosurgery 2000, 46, 440), pain, e.g. neuropathic pain (Tatsumi, et al. Neuroscience 2005, 131, 491, Inoue, et al. Nature medicine 2004, 10, 712), infection of digestive tracts with bacteria (WO 98/06433), cancer development and progression, neoplasia where inhibition of Rho kinase has been shown to inhibit tumor cell growth and metastasis (Itoh, et al. Nature Medicine 1999, 5, 221; Somlyo, et al. Res Commun 2000, 269, 652), angiogenesis (Uchida, et al. Biochem Biophys Res 2000, 269, 633-40; Gingras, et al. Biochem J 2000, 348, 273), vascular smooth muscle cell proliferation and motility (Tammy et al. Circ. Res. 1999, 84, 1186-1193; Tangkijvanich et al. Atherosclerosis 2001, 155, 321-327), endothelial cell proliferation, endothelial cell retraction and motility (Oikawa et al. Biochem. Biophys. Res. Commun. 2000, 269, 633-640), stress fiber formation (Kimura et al. Science 1997, 275, 1308-1311; Yamashiro et al. J. Cell Biol. 2000, 150, 797-806), thrombotic disorders (Kikkawa, et al. FEBS Lett. 2000, 466, 70-74; Bauer et al. Blood 1999, 94, 1665-1672, Klages, et al. J Cell Biol 1999, 144, 745; Retzer, et al. Cell Signal 2000, 12, 645) and leukocyte aggregation (Kawaguchi, et al. Eur J Pharmacol. 2000, 403:203-8; Sanchez-Madrid, et al. J Immunol. 2003, 171, 1023-34, Sanchez-Madrid, et al. J Immunol. 2002, 168, 400-10), and bone resorption (Chellaiah, et al. J Biol. Chem. 2003, 278, 29086-97). Na/H exchange transport system activation (Kawaguchi, et al. Eur J Pharmacol. 2000, 403, 203-8), Alzheimer's disease (Zhou et al. Science 2003, 302, 1215-1217), adducin activation (Fukata et al. J. Biol. Chem., 1998, 273, 5542-5548), and in SREB (Sterol response binding element) signalling and its effects on lipid metabolism (Lin et al. Circ. Res., 92, 1296-304, 2003).

Therefore, a compound having inhibitory effect on Rho-kinase and/or on Rho-kinase mediated phosphorylation of myosin light chain phosphatase is useful for the treatment and/or prevention of cardiovascular and non-cardiovascular diseases involving Rho-kinase as the primary or secondary disease cause, like hypertension, pulmonary hypertension, ocular hypertension, retinopathy, and glaucoma, peripheral circulatory disorder, peripheral arterial occlusive disease (PAOD), coronary heart disease, angina pectoris, heart hypertrophy, heart failure, ischemic diseases, ischemic organ failure (end organ damage), fibroid lung, fibroid liver, liver failure, nephropathy, including hypertension-induced, non-hypertension-induced, and diabetic nephropathies, renal failure, fibroid kidney, renal glomerulosclerosis, organ hypertrophy, asthma, chronic obstructive pulmonary disease (COPD), adult respiratory distress syndrome, thrombotic disorders, stroke, cerebral vasospasm, cerebral ischemia, pain, e.g. neuropathic pain, neuronal degeneration, spinal cord injury, Alzheimer's disease, premature birth, erectile dysfunction, endocrine dysfunctions, arteriosclerosis, prostatic hypertrophy, diabetes and complications of diabetes, metabolic syndrome, blood vessel restenosis, atherosclerosis, inflammation, autoimmune diseases, AIDS, osteopathy such as osteoporosis, infection of digestive tracts with bacteria, sepsis, cancer development and progression, e.g. cancers of the breast, colon, prostate, ovaries, brain and lung and their metastases.

WO 01/64238 describes isoquinoline-5-sulfonamide derivatives optionally substituted by a —$(CH_2)_{1-6}$—O—$(CH_2)_{0-6}$—, a —$(CH_2)_{0-6}$—S—$(CH_2)_{0-6}$— or a —$(CH_2)_{0-6}$-linked heterocyclic group useful as neuroprotective agents.

WO 2004/106325 (Schering AG) describes prodrugs of the Rho-kinase inhibitor fasudil carrying an ether or ester group in the 1-position of the isoquinoline ring.

WO 2001/039726 generically describes —O—$(C_0$-$C_{10})$ alkyl-heteroaryl substituted cyclohexyl derivatives useful for the treatment of microbial infections. JP 10087629 A describes isoquinoline derivatives useful for the treatment of diseases caused by *Heliobacter pylori* such as for example gastritis cancer or ulcer. The isoquinoline derivatives may be substituted by OH in the 1-position and are preferably 5-substituted by $X-[(C_1-C_6)alkylene)]_{0-1}-Y$ wherein X may be oxygen and Y may be an aryl or a heterocyclic group.

Hagihara et al. (Bioorg. Med. Chem. 1999, 7, 2647-2666) disclose 6-benzyloxy-isoquinoline for the treatment of infections caused by *Heliobacter pylori*.

U.S. Pat. No. 5,480,883 generically discloses as EGF and/or PDGF receptor inhibitors useful for inhibiting cell proliferation compounds of the formula "Ar I-X-Ar II" wherein X may be $(CHR_1)_m-Z-(CHR_1)_n$, e.g. $Z-CH_2$, wherein Z may be O, $R_1$ is hydrogen or alkyl, Ar I may be among others an optionally substituted isoquinolone and Ar II may be among others an optionally substituted $C_{3-7}$ monocyclic saturated heterocyclic system.

WO 2005/030791 (Merck & Co.) generically describes as potassium channel inhibitors for the treatment of cardiac arrhythmias, stroke, congestive heart failure etc. isoquinolone derivatives which are optionally substituted in 6-position by a group $(CR^eR^f)_pOR^{43}$ wherein p may be zero, and $R^{43}$ is e.g. a $(C_3-C_{10})$cycloalkyl residue optionally substituted by $NR^{51}R^{52}$, wherein $R^{51}$ and $R^{52}$ may be hydrogen, $(C_1-C_6)$alkyl etc.; or $R^{43}$ is a group $R^{81}$ defined as a 4-6 membered unsaturated or saturated monocyclic heterocyclic ring with 1, 2, 3 or 4 heteroatoms; and are substituted by a directly bound optionally substituted aryl or heteroaryl ring in the 4-position.

WO 2005/030130 (Merck & Co.) generically describes as potassium channel inhibitors for the treatment of cardiac arrhythmias, stroke, congestive heart failure etc. isoquinoline derivatives which may be substituted by hydroxyl in the 1-position and are optionally substituted in 6-position by a group $(CR^eR^f)_pOR^{43}$ wherein p may be zero, and $R^{43}$ is e.g. a $(C_3-C_{10})$cycloalkyl residue optionally substituted by $NR^{51}R^{52}$, wherein $R^{51}$ and $R^{52}$ may be hydrogen, $(C_1-C_6)$alkyl etc.; or $R^{43}$ is a group $R^{81}$ defined as a 4-6 membered unsaturated or saturated monocyclic heterocyclic ring with 1, 2, 3 or 4 heteroatoms; and are substituted by a directly bound optionally substituted aryl or heteroaryl ring in the 4-position.

WO 03/053330 (Ube) generically describes isoquinolone derivatives of the formula

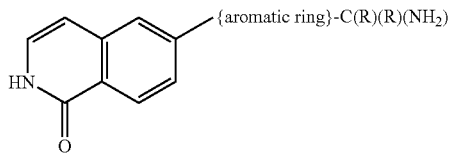

as Rho-kinase inhibitors.

SUMMARY OF THE INVENTION

An embodiment of the present invention is a compound of the formula (I)

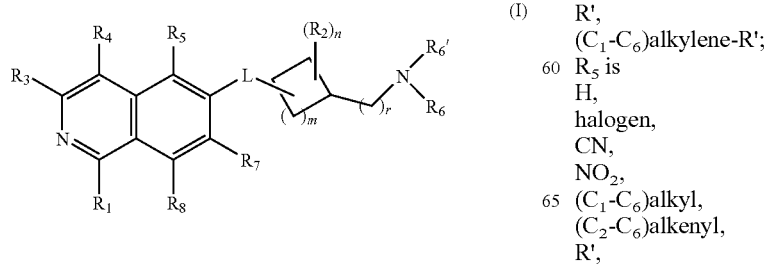

(I)

wherein
$R_1$ is H, OH or $NH_2$;
$R_2$ is
R',
$(C_7-C_8)$alkyl,
$(C_1-C_6)$alkylene-R',
$(C_2-C_6)$alkenyl,
$(C_2-C_6)$alkynyl,
$(C_1-C_6)$alkylene-O—$(C_1-C_6)$alkyl,
$(C_1-C_6)$alkylene-O—R',
$(C_1-C_6)$alkylene-CH[R']$_2$,
$(C_1-C_6)$alkylene-C(O)—R',
$(C_1-C_6)$alkylene-C(O)NH$_2$,
$(C_1-C_6)$alkylene-C(O)NH—R',
$(C_1-C_6)$alkylene-C(O)NH—$(C_1-C_6)$alkyl,
$(C_1-C_6)$alkylene-C(O)N[$(C_1-C_6)$alkyl]$_2$,
$(C_1-C_6)$alkylene-C(O)N[R']$_2$;
$(C_1-C_6)$alkylene-C(O)O—$(C_1-C_6)$alkyl,
C(O)O—$(C_1-C_6)$alkyl,
C(O)OR'
C(O)$(C_1-C_6)$alkyl,
C(O)R',
C(O)NH—$(C_1-C_6)$alkyl,
C(O)NHR',
C(O)—NH—$(C_2-C_6)$alkenyl,
C(O)—NH—$(C_2-C_6)$alkynyl,
C(O)—NH$(C_1-C_6)$alkylene-R',
C(O)N[$(C_1-C_6)$alkyl]R'
C(O)N[$(C_1-C_6)$alkyl]$_2$,
C(O)—$(C_1-C_6)$alkylene-R', or
C(O)O$(C_1-C_6)$alkylene-R'; or
$R_2$ is $(C_1-C_6)$alkyl, provided that in said alkyl residue at least one hydrogen is substituted by OH, $OCH_3$, COOH, $COOCH_3$, $NH_2$, $NHCH_3$, $N(CH_3)_2$, $CONH_2$, $CONHCH_3$ or $CON(CH_3)_2$; or
$R_2$ is a $(C_1-C_4)$alkylene bound to the cycloalkyl amine, in which the $(C_1-C_4)$ alkylene forms a second bond to a different carbon atom of the cycloalkyl amine ring and forms, together with carbon atoms of the cycloalkyl amine, a second, 4-8 membered ring;
$R_3$ is
H,
halogen,
$(C_1-C_6)$alkyl,
$(C_1-C_6)$alkylene-R',
OH,
O—R",
$NH_2$,
NHR",
NR"R" or
NH—C(O)—R",
$R_4$ is
H,
halogen,
hydroxy,
CN,
$(C_1-C_6)$alkyl,
R',
$(C_1-C_6)$alkylene-R';
$R_5$ is
H,
halogen,
CN,
$NO_2$,
$(C_1-C_6)$alkyl,
$(C_2-C_6)$alkenyl,
R', (C$_1$-C$_6$)alkylene-(C$_6$-C$_{10}$)aryl,
(C$_2$-C$_6$)alkenylene-(C$_6$-C$_{10}$)aryl,
(C$_1$-C$_6$)alkylene-(C$_5$-C$_{10}$)heterocyclyl,
CH(OH)—(C$_1$-C$_6$)alkyl,
NH$_2$,
NH—R',
NH—SO$_2$H,
NH—SO$_2$—(C$_1$-C$_6$)alkyl,
NH—SO$_2$—R',
NH—C(O)—(C$_1$-C$_6$)alkyl,
NH—C(O)—R',
C(O)N[(C$_1$-C$_6$)alkyl]$_2$,
C(O)OH, or
C(O)O—(C$_1$-C$_6$)alkyl;
R$_6$ and R$_6$' are independently of each other
H,
R',
(C$_1$-C$_8$)alkyl,
(C$_1$-C$_6$)alkylene-R',
(C$_1$-C$_6$)alkylene-O—(C$_1$-C$_6$)alkyl,
(C$_1$-C$_6$)alkylene-O—R',
(C$_1$-C$_6$)alkylene-CH[R']$_2$,
(C$_1$-C$_6$)alkylene-C(O)—R',
(C$_1$-C$_6$)alkylene-C(O)NH$_2$,
(C$_1$-C$_6$)alkylene-C(O)NH—R',
(C$_1$-C$_6$)alkylene-C(O)NH—(C$_1$-C$_6$)alkyl,
(C$_1$-C$_6$)alkylene-C(O)N[(C$_1$-C$_6$)alkyl]$_2$,
(C$_1$-C$_6$)alkylene-C(O)N[R']$_2$;
(C$_1$-C$_6$)alkylene-C(O)O—(C$_1$-C$_6$)alkyl,
C(O)O—(C$_1$-C$_6$)alkyl,
C(O)OR'
C(O)(C$_1$-C$_6$)alkyl,
C(O)R',
C(O)NH—(C$_1$-C$_6$)alkyl,
C(O)NHR',
C(O)N[(C$_1$-C$_6$)alkyl]R'
C(O)N[(C$_1$-C$_6$)alkyl]$_2$,
C(O)—(C$_1$-C$_6$)alkylene-R', or
C(O)O(C$_1$-C$_6$)alkylene-R', or
R$_6$ and R$_6$', together with the N-atom to which they are attached, form a (C$_5$-C$_{10}$) heterocyclyl group;
R$_7$ is
H,
halogen,
CN,
NO$_2$,
(C$_1$-C$_6$)alkyl,
O—(C$_1$-C$_6$)alkyl,
(C$_2$-C$_6$)alkenyl,
R',
(C$_2$-C$_6$)alkenylene-(C$_6$-C$_{10}$)aryl,
(C$_1$-C$_6$)alkylene-R',
CH(OH)—(C$_1$-C$_6$)alkyl,
NH$_2$,
NH—R',
NH—SO$_2$H,
NH—SO$_2$—(C$_1$-C$_6$)alkyl,
NH—SO$_2$—R',
SO$_2$—NH$_2$,
SO$_2$—NHR',
NH—C(O)—(C$_1$-C$_6$)alkyl,
NH—C(O)—R',
C(O)N[(C$_1$-C$_6$)alkyl]$_2$,
C(O)OH, or
C(O)O—(C$_1$-C$_6$)alkyl;
R$_8$ is H, halogen or (C$_1$-C$_6$)alkyl;
n is 1, 2, 3 or 4;
m is 1, 2, 3, 4 or 5;
r is 0, 1 or 2, and
L is O—(CH$_2$)p, S(CH$_2$)p, S(O)(CH$_2$)p, SO$_2$(CH$_2$)p, NH(CH$_2$)p, N(C$_1$-C$_6$)alkyl-(CH$_2$)p, N(C$_3$-C$_6$)cycloalkyl-(CH$_2$)p, N[CO(C$_1$-C$_6$)alkyl]-(CH$_2$)p or N[(C$_1$-C$_3$)alkylene-R']—(CH$_2$)p;
p is 0, 1, 2, 3 or 4;
R' is
(C$_3$-C$_8$)cycloalkyl,
(C$_5$-C$_{10}$)heterocyclyl,
(C$_6$-C$_{10}$)aryl; and
R" is
(C$_3$-C$_8$)cycloalkyl,
(C$_5$-C$_{10}$)heterocyclyl,
(C$_6$-C$_{10}$)aryl,
(C$_1$-C$_6$)alkyl,
(C$_1$-C$_6$)alkylene-R',
(C$_1$-C$_6$)alkylene-O—(C$_1$-C$_6$)alkyl,
(C$_1$-C$_6$)alkylene-O—R', or
(C$_1$-C$_6$)alkylene-NR$_x$R$_y$; and
R$_x$ and R$_y$ are independently of each other
(C$_1$-C$_6$)alkyl,
(C$_5$-C$_{10}$)heterocyclyl,
(C$_6$-C$_{10}$)aryl,
(C$_1$-C$_4$)alkylene-(C$_5$-C$_{10}$)heterocyclyl,
(C$_1$-C$_4$)alkylene-(C$_6$-C$_{10}$)aryl,
(C$_1$-C$_4$)alkylene-NH(C$_1$-C$_6$)alkyl,
(C$_1$-C$_4$)alkylene-N[(C$_1$-C$_6$)alkyl]$_2$,
(C$_1$-C$_4$)alkylene-N[(C$_6$-C$_{10}$)aryl]$_2$, or
(C$_1$-C$_4$)alkylene-N[(C$_5$-C$_{10}$)heterocyclyl]$_2$;
wherein in residues R$_2$, R$_4$, R$_5$, R$_6$, R$_6$', R$_7$ and R$_8$ as alkyl, alkylene or cycloalkyl can optionally be substituted one or more times by OH, OCH$_3$, COOH, COOCH$_3$, NH$_2$, NHCH$_3$, N(CH$_3$)$_2$, CONH$_2$, CONHCH$_3$ or CON(CH$_3$)$_2$;
wherein in residues R$_2$ to R$_8$ as alkyl or alkylene can optionally be substituted one or more times by halogen;
wherein in residues R$_2$ to R$_8$ as (C$_6$-C$_{10}$)aryl and (C$_5$-C$_{10}$)heterocyclyl are unsubstituted or substituted one or more times by a suitable group independently selected from halogen, OH, NO$_2$, N$_3$, CN, C(O)—(C$_1$-C$_6$)alkyl, C(O)—(C$_6$-C$_{10}$)aryl, COOH, COO(C$_1$-C$_6$)alkyl, CONH$_2$, CONH(C$_1$-C$_6$)alkyl, CON[(C$_1$-C$_6$)alkyl]$_2$, (C$_3$-C$_8$)cycloalkyl, (C$_1$-C$_6$)alkyl, (C$_1$-C$_6$)alkylene-OH, (C$_1$-C$_6$)alkylene-NH$_2$, (C$_1$-C$_6$)alkylene-NH(C$_1$-C$_6$)alkyl, (C$_1$-C$_6$)alkylene-N[(C$_1$-C$_6$)alkyl]$_2$, (C$_2$-C$_6$)alkenyl, (C$_2$-C$_6$)alkynyl, O—(C$_1$-C$_6$)alkyl, O—C(O)—(C$_1$-C$_6$)alkyl, PO$_3$H$_2$, SO$_3$H, SO$_2$—NH$_2$, SO$_2$NH(C$_1$-C$_6$)alkyl, SO$_2$N[(C$_1$-C$_6$)alkyl]$_2$, S—(C$_1$-C$_6$)alkyl, SO—(C$_1$-C$_6$)alkyl, SO$_2$—(C$_1$-C$_6$)alkyl, SO$_2$—N=CH—N[(C$_1$-C$_6$)alkyl]$_2$, C(NH)(NH$_2$), NH$_2$, NH—(C$_1$-C$_6$)alkyl, N[(C$_1$-C$_6$)alkyl]$_2$, NH—C(O)—(C$_1$-C$_6$)alkyl, NH—C(O)O—(C$_1$-C$_6$)alkyl, NH—SO$_2$—(C$_1$-C$_6$)alkyl, NH—SO$_2$—(C$_6$-C$_{10}$)aryl, NH—SO$_2$—(C$_5$-C$_{10}$)heterocyclyl, N(C$_1$-C$_6$)alkyl-C(O)—(C$_1$-C$_6$)alkyl, N(C$_1$-C$_6$)alkyl-C(O)O—(C$_1$-C$_6$)alkyl, N(C$_1$-C$_6$)alkyl-C(O)—NH—(C$_1$-C$_6$)alkyl], (C$_6$-C$_{10}$)aryl, (C$_1$-C$_6$)alkylene-(C$_6$-C$_{10}$)aryl, O—(C$_6$-C$_{10}$)aryl, O—(C$_1$-C$_6$)alkylene-(C$_6$-C$_{10}$)aryl, (C$_5$-C$_{10}$)heterocyclyl, (C$_1$-C$_6$)alkylene-(C$_5$-C$_{10}$)heterocyclyl and O—(C$_1$-C$_6$)alkylene-(C$_5$-C$_{10}$)heterocyclyl, wherein the (C$_6$-C$_{10}$)aryl or (C$_5$-C$_{10}$)heterocyclyl in the substituent may be substituted one to three times by a group independently selected from halogen, OH, NO$_2$, CN, O—(C$_1$-C$_6$)alkyl, (C$_1$-C$_6$)alkyl, NH$_2$, NH(C$_1$-C$_6$)alkyl, N[(C$_1$-C$_6$)alkyl]$_2$, SO$_2$CH$_3$, COOH, C(O)O—(C$_1$-C$_6$)alkyl, CONH$_2$, (C$_1$-C$_6$)alkylene-O—(C$_1$-C$_6$)alkyl, (C$_1$-C$_6$)alkylene-O—(C$_6$-C$_{10}$)aryl and O—(C$_1$-C$_6$)alkylene-(C$_6$-C$_{10}$)aryl; or wherein (C$_6$-C$_{10}$)aryl is vicinally substituted by a O—(C$_1$-C$_4$)alkylene-O group whereby a 5-8-membered ring is formed together with the carbon atoms the oxygen atoms are attached to; and wherein aryl substituent of $(C_6-C_{10})$aryl and $(C_5-C_{10})$heterocyclyl substituent groups may not be further substituted by an aryl or heterocyclyl containing group; or stereoisomeric form thereof and/or tautomeric form thereof and/or pharmaceutically acceptable salt thereof.

DETAILED DESCRIPTION OF THE INVENTION

Definitions

The terms $(C_1-C_2)$alkyl, $(C_1-C_4)$alkyl, $(C_1-C_6)$alkyl, $(C_1-C_8)$alkyl and the corresponding alkylene substituents are understood as a hydrocarbon residue which can be linear, i.e. straight-chain, or branched and has 1, 2, 3, 4, 5, 6, 7 or 8 carbon atoms, respectively. This also applies if an alkyl group occurs as a substituent on another group, for example in an alkoxy group (O-alkyl), S-alkyl or a —O($C_1-C_6$)alkylene-O—, an alkoxycarbonyl group or an arylalkyl group. Examples of alkyl groups are methyl, ethyl, propyl, butyl, pentyl or hexyl, the n-isomers of all these groups, isopropyl, isobutyl, 1-methylbutyl, isopentyl, neopentyl, 2,2-dimethylbutyl, 2-methylpentyl, 3-methylpentyl, isohexyl, sec-butyl, tert-butyl or tert-pentyl. Alkyl or alkylene groups may—if not otherwise stated—be halogenated once or more, e.g. alkyl groups may be fluorinated, e.g. perfluorinated. Examples of halogenated alkyl groups are $CF_3$ and $CH_2CF_3$, $OCF_3$, $SCF_3$, or —O—$(CF_2)_2$—O—.

The term $(C_2-C_6)$-alkenyl means a hydrocarbon residue whose carbon chain is straight-chain or branched and comprises 2 to 6 carbon atoms and have, depending on the chain length, 1, 2 or 3 double bonds, for example, vinyl, 1-propenyl, 2-propenyl (=allyl), 2-butenyl, 3-butenyl, 2-methyl-2-butenyl, 3-methyl-2-butenyl, 5-hexenyl or 1,3-pentadienyl. The double bond may where possible have the E or Z orientation. The double bonds may be both internal and terminal.

$(C_2-C_6)$-alkynyl groups are hydrocarbon radicals whose carbon chain is straight-chain or branched and comprises 2 to 6 carbon atoms and have, depending on the chain length, 1 or 2 triple bonds, for example, ethynyl, 1-propynyl, 2-propynyl (=propargyl) or 2-butynyl. The triple bonds may be both internal and terminal.

Halogen means fluoro, chloro, bromo or iodo.

$(C_3-C_8)$cycloalkyl groups are cyclic alkyl groups containing 3, 4, 5, 6, 7 or 8 ring carbon atoms like cyclopropyl, cyclobutyl, cyclopentyl, cyclohexyl or cyclooctyl, which can also be substituted and/or contain 1 or 2 double bounds (unsaturated cycloalkyl groups) like, for example, cyclopentenyl or cyclohexenyl can be bonded via any carbon atom.

A $(C_6-C_{10})$aryl group means an aromatic ring or a ring system which comprises two aromatic rings which are fused or otherwise linked, for example a phenyl, naphthyl, biphenyl, tetrahydronaphthyl, alpha- or beta-tetralon-, indanyl- or indan-1-on-yl group. A preferred $(C_6-C_{10})$aryl group is phenyl.

A $(C_5-C_{10})$heterocyclyl group means a mono- or bicyclic ring system in which one or more carbon atoms can be replaced by one or more heteroatoms such as, for example 1, 2 or 3 nitrogen atoms, 1 or 2 oxygen atoms, 1 or 2 sulfur atoms or combinations of different hetero atoms. The heterocyclyl residues can be bound at any positions, for example on the 1-position, 2-position, 3-position, 4-position, 5-position, 6-position, 7-position or 8-position. $(C_5-C_{10})$heterocyclyl groups may be (1) aromatic [=heteroaryl groups] or (2) saturated or (3) mixed aromatic/saturated.

Suitable $(C_5-C_{10})$heterocyclyl group include acridinyl, azocinyl, benzimidazolyl, benzofuryl, benzomorpholinyl, benzothienyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, furanyl, quinazolinyl, quinolinyl, 4H-quinolizinyl, quinoxalinyl, quinuclidinyl, chromanyl, chromenyl, chromen-2-onyl, cinnolinyl, decahydroquinolinyl, 2H,6H-1,5,2-dithiazinyl, dihydrofuro[2,3-b]-tetrahydrofuran, furyl, furazanyl, homomorpholinyl, homopiperazinyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, prolinyl, pteridinyl, purynyl, pyranyl, pyrazinyl, pyroazolidinyl, pyrazolinyl, pyrazolyl, pyridazinyl, pyridonyl, pyridooxazoles, pyridoimidazoles, pyridothiazoles, pyridinyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, 6H-1,2,5-thiadazinyl, thiazolyl, 1,2,3-thiadiazolyl, 1,2,4-thiadiazolyl, 1,2,5-thiadiazolyl, 1,3,4-thiadiazolyl, thienyl, triazolyl, tetrazolyl and xanthenyl. Pyridyl stands both for 2-, 3- and 4-pyridyl. Thienyl stands both for 2- and 3-thienyl. Furyl stands both for 2- and 3-furyl. Also included are the corresponding N-oxides of these compounds, for example, 1-oxy-2-, 3- or 4-pyridyl.

Substitutions in $(C_5-C_{10})$heterocyclyl residues can occur on free carbon atoms or on nitrogen atoms.

Preferred examples of $(C_5-C_{10})$heterocyclyl residues are pyrazinyl, pyridyl, pyrimidinyl, pyrazolyl, morpholinyl, pyrrolidinyl, piperazinyl, piperidinyl, thienyl, benzofuryl, quinolinyl, tetrazolyl and triazolyl. A preferred $(C_5-C_{10})$heterocyclyl is $(C_5-C_6)$heterocyclyl.

$(C_6-C_{10})$aryl and $(C_5-C_{10})$heterocyclyl groups are unsubstituted or, if not stated otherwise, substituted one or more times, preferably one to three times, by suitable groups independently selected from halogen, OH, $NO_2$, $N_3$, CN, C(O)—$(C_1-C_6)$alkyl, C(O)—$(C_6-C_{10})$aryl, COOH, COO$(C_1-C_6)$alkyl, $CONH_2$, CONH$(C_1-C_6)$alkyl, CON[$(C_1-C_6)$alkyl]$_2$, $(C_3-C_8)$cycloalkyl, $(C_1-C_6)$alkyl, $(C_1-C_6)$alkylene-OH, $(C_1-C_6)$alkylene-$NH_2$, $(C_1-C_6)$alkylene-NH$(C_1-C_6)$alkyl, $(C_1-C_6)$alkylene-N[$(C_1-C_6)$alkyl]$_2$, $(C_2-C_6)$alkenyl, $(C_2-C_6)$alkynyl, O—$(C_1-C_6)$alkyl, O—C(O)—$(C_1-C_6)$alkyl, $PO_3H_2$, $SO_3H$, $SO_2$—$NH_2$, $SO_2NH(C_1-C_6)$alkyl, $SO_2N[(C_1-C_6)$alkyl]$_2$, S—$(C_1-C_6)$alkyl; SO—$(C_1-C_6)$alkyl, $SO_2$—$(C_1-C_6)$alkyl, $SO_2$—N=CH—N[$(C_1-C_6)$alkyl]$_2$, $C(NH)(NH_2)$, $NH_2$, NH—$(C_1-C_6)$alkyl, N[$(C_1-C_6)$alkyl]$_2$, NH—C(O)—$(C_1-C_6)$alkyl, NH—C(O)O—$(C_1-C_6)$alkyl, NH—$SO_2$—$(C_1-C_6)$alkyl, NH—$SO_2$—$(C_6-C_{10})$aryl, NH—$SO_2$—$(C_5-C_{10})$heterocyclyl, N$(C_1-C_6)$alkyl-C(O)—$(C_1-C_6)$alkyl, N$(C_1-C_6)$alkyl-C(O)O—$(C_1-C_6)$alkyl, N$(C_1-C_6)$alkyl-C(O)—NH—$(C_1-C_6)$alkyl], $(C_6-C_{10})$aryl, $(C_1-C_6)$alkylene-$(C_6-C_{10})$aryl, O—$(C_6-C_{10})$aryl, O—$(C_1-C_6)$alkylene-$(C_6-C_{10})$aryl, $(C_5-C_{10})$heterocyclyl, $(C_1-C_6)$alkylene-$(C_5-C_{10})$heterocyclyl, O—$(C_1-C_6)$alkylene-$(C_5-C_{10})$heterocyclyl, wherein the $(C_6-C_{10})$aryl or $(C_5-C_{10})$heterocyclyl may be substituted one to 3 times by a group independently selected from halogen, OH, $NO_2$, CN, O—$(C_1-C_6)$alkyl, $(C_1-C_6)$alkyl, $NH_2$, NH$(C_1-C_6)$alkyl, N[$(C_1-C_6)$alkyl]$_2$, $SO_2CH_3$, COOH, C(O)O—$(C_1-C_6)$alkyl, $CONH_2$, $(C_1-C_6)$alkylene-O—$(C_1-C_6)$alkyl, $(C_1-C_6)$alkylene-O—$(C_6-C_{10})$aryl, O—$(C_1-C_6)$alkylene-$(C_6-C_{10})$aryl; or wherein $(C_6-C_{10})$aryl is vicinally substituted by a O—$(C_1-C_4)$alkylene-O group whereby a 5-8-membered ring is formed together with the carbon atoms the oxygen atoms are attached to. Aryl or heterocyclyl substituents of $(C_6-C_{10})$aryl and $(C_5-C_{10})$heterocyclyl groups may not be further substituted by an aryl or heterocyclyl containing group.

Preferred substituents for $(C_6-C_{10})$aryl groups are $(C_1-C_4)$alkyl, O—$(C_1-C_4)$alkyl, O-phenyl, phenyl, C(O)O—$(C_1-C_6)$alkyl, C(O)OH, C(O)—$(C_1-C_4)$alkyl, halogen, $NO_2$, $SO_2NH_2$, CN, $SO_2$—$(C_1-C_4)$alkyl, $SO_2$—N=CH—N[$(C_1-C_6)$alkyl]$_2$, NH—$SO_2$—$(C_1-C_4)$alkyl, $NH_2$, NH—C(O)—$(C_1-C_4)$alkyl, $(C_3-C_8)$cycloalkyl, $(C_1-C_4)$alkyl-OH, C(O)N[$(C_1-C_4)$alkyl]$_2$, CONH$(C_1-C_6)$alkyl, C(O)$NH_2$, N[$(C_1-C_4)$alkyl]$_2$, $(C_1-C_4)$alkylene-$(C_6-C_{10})$aryl, wherein the $(C_6-C_{10})$aryl may be further substituted one to three times, preferably once, by $(C_1-C_4)$alkyl, $(C_1-C_4)$alkylene-O—$(C_1-C_6)$alkyl, $(C_6-C_{10})$aryl O—$(C_1-C_6)$alkyl-$(C_6-C_{10})$aryl, or may be vicinally substituted by a O—$(C_1-C_4)$alkylene-O group whereby a 5-8-membered ring is formed together with the carbon atoms the oxygen atoms are attached to. More preferred substituents for $(C_6-C_{10})$aryl are halogen, CN, phenyl, O-phenyl, NH—C(O)—$(C_1-C_4)$alkyl especially NH—C(O)—$CH_3$, C(O)—$(C_1-C_4)$alkyl especially C(O)—$CH_3$, C(O)—O$(C_1-C_4)$alkyl especially C(O)—$OCH_3$, $(C_1-C_4)$alkyl especially $CH_3$ or $CF_3$, O—$(C_1-C_4)$alkyl especially O—$CH_3$, $SO_2$—$NH_2$, $SO_2$—$(C_1-C_4)$alkyl especially $SO_2$—$CH_3$ or $SO_2$—$CF_3$; or $SO_2$—N=CH—N[$(C_1-C_4)$alkyl]$_2$ especially $SO_2$—N=CH—N[$(CH_3)_2$.

In monosubstituted phenyl groups the substituent can be located in the 2-position, the 3-position or the 4-position, with the 3-position and the 4-position being preferred. If a phenyl group carries two substituents, they can be located in 2,3-position, 2,4-position, 2,5-position, 2,6-position, 3,4-position or 3,5-position. In phenyl groups carrying three substituents the substituents can be located in 2,3,4-position, 2,3,5-position, 2,3,6-position, 2,4,5-position, 2,4,6-position, or 3,4,5-position.

The above statements relating to phenyl groups correspondingly apply to divalent groups derived from phenyl groups, i.e. phenylene which can be unsubstituted or substituted 1,2-phenylene, 1,3-phenylene or 1,4-phenylene. The above statements also correspondingly apply to the aryl subgroup in arylalkylene groups. Examples of arylalkylene groups which can also be unsubstituted or substituted in the aryl subgroup as well as in the alkylene subgroup, are benzyl, 1-phenylethylene, 2-phenylethylene, 3-phenylpropylene, 4-phenylbutylene, 1-methyl-3-phenyl-propylene.

Preferred substituents for $(C_5-C_{10})$heterocyclyl groups are $(C_1-C_4)$alkyl, O—$(C_1-C_4)$alkyl, $(C_1-C_4)$alkylene-phenyl, halogen, $(C_1-C_4)$alkylene-O—$(C_1-C_4)$alkyl, $(C_5-C_{10})$heterocyclyl, $(C_1-C_4)$alkylene-N[$(C_1-C_4)$alkyl]$_2$, or $(C_6-C_{10})$aryl, wherein the $(C_6-C_{10})$aryl may be further substituted by halogen, $(C_1-C_4)$alkyl, O—$(C_1-C_4)$alkyl, $(C_1-C_4)$alkylene-O—$(C_1-C_6)$alkyl, O—$(C_1-C_6)$alkyl-$(C_6-C_{10})$aryl, or may be vicinally substituted by a O—$(C_1-C_4)$alkylene-O group whereby a 5-8-membered ring is formed together with the carbon atoms the oxygen atoms are attached to. More preferred substituents for $(C_5-C_{10})$heterocyclyl groups are $(C_1-C_4)$alkyl, O—$(C_1-C_4)$alkyl, halogen or phenyl, wherein the phenyl may be further substituted one to three times, preferably once, by halogen, $(C_1-C_4)$alkyl or O—$(C_1-C_4)$alkyl.

The general and preferred substituents of $(C_6-C_{10})$aryl and $(C_5-C_{10})$heterocyclyl groups may be combined with the general and preferred definitions of $R_1$, $R_2$, $R_3$, $R_4$, $R_5$, $R_6$, $R_6'$, $R_7$, $R_8$, n, m and L as described above.

Embodiments

In one embodiment of the present invention $R_1$ is H and the compound is characterized by the formula (II)

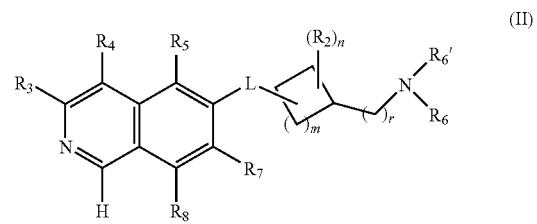

In another embodiment of the present invention $R_1$ is OH and the compound is characterized by the formula (III)

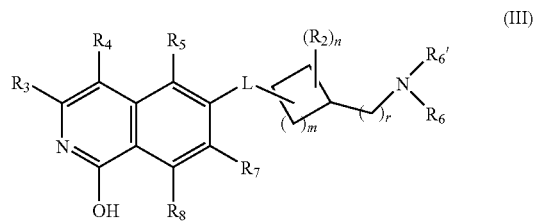

The isoquinoline derivative of formula (I), wherein $R_1$ is OH, include the corresponding tautomeric 1-isoquinolone derivative which is characterized by the formula (III')

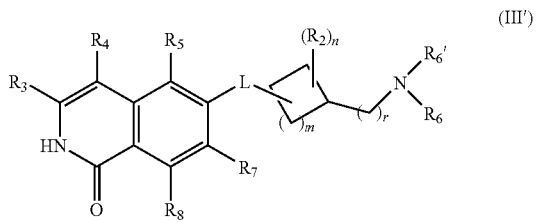

This tautomeric form is also an embodiment of the present invention.

In a further embodiment $R_1$ is $NH_2$ and the compound is characterized by the formula (IV)

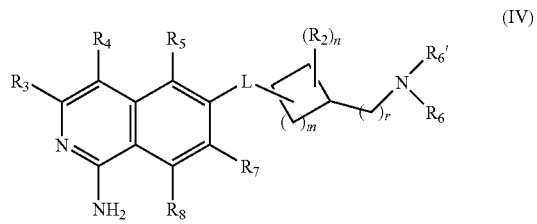

The following embodiments refer to the compounds of formula (I), (II), (III), (III') and (IV).

$R_1$ is preferably H or OH;

$R_3$ is preferably H, halogen, $(C_1-C_4)$alkylene-R', O—R" or NHR". More preferred, $R_3$ is H or NHR". Most preferred, $R_3$ is H, NH—$(C_5-C_6)$heterocyclyl or NH-phenyl, especially preferred are H, NH—$(C_5-C_6)$heteroaryl containing one or more N atoms or NH-phenyl. Most especially preferred, $R_3$ is H.

Examples of R₃ substituents are

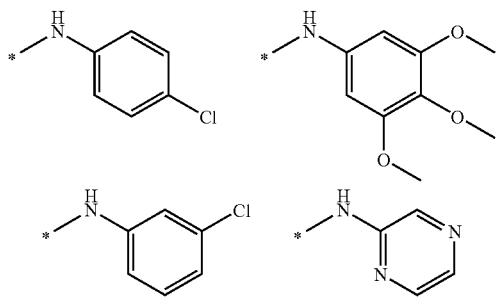

Preferably, $R_4$ is H, halogen or $(C_1-C_6)$alkyl. More preferred, $R_4$ is H, halogen or $(C_1-C_4)$alkyl. Most preferred, $R_4$ is H.

Preferably, $R_5$ is H, halogen, CN, $(C_1-C_6)$alkyl, $(C_2-C_6)$alkenyl, R', NH—$(C_6-C_{10})$aryl or $(C_1-C_6)$alkylene-R'. More preferably, $R_5$ is H, halogen, $(C_1-C_6)$alkyl, $(C_2-C_6)$alkenyl, R', NH—$(C_6-C_{10})$aryl or $(C_1-C_6)$alkylene-R'. Most preferably, $R_5$ is H, halogen, $(C_1-C_6)$alkyl, $(C_2-C_6)$alkenyl, $(C_6-C_{10})$aryl, NH—$(C_6-C_{10})$aryl, $(C_1-C_2)$alkyl-$(C_6-C_{10})$aryl or $(C_5-C_{10})$heteroaryl. Especially preferred, $R_5$ is H, halogen, phenyl, $(C_1-C_6)$alkyl, $(C_2-C_6)$alkenyl, $(C_6-C_{10})$aryl or $(C_5-C_6)$heteroaryl. Most especially preferred $R_5$ is H, halogen, methyl, ethyl, vinyl, phenyl, thienyl or pyridyl.

Examples of $R_5$ are hydrogen, fluoro, chloro, bromo, iodo, methyl, ethyl, vinyl, phenyl, thienyl or pyridyl, nitrile, nitro, (p-methoxy)-phenyl, N-aniline, benzyl, 2-propenyl, s-butenyl, cyclopropyl, tetrazol, amino, 4-methoxy-aniline or N-acetyl, preferably hydrogen, fluoro, chloro, bromo, iodo, methyl, ethyl, vinyl, phenyl, thienyl or pyridyl More preferred, $R_5$ is H, halogen, methyl, or ethyl, most preferred $R_5$ is H.

Preferably, $R_6$ and $R_6'$ are independently of each other H, $(C_1-C_6)$alkyl, R', $(C_1-C_4)$alkylene-$(C_3-C_8)$cycloalkyl, $(C_1-C_4)$alkylene-$(C_5-C_{10})$heterocyclyl, $(C_1-C_4)$alkylene-$(C_6-C_{10})$aryl, $(C_1-C_6)$alkylene-O—$(C_1-C_6)$alkyl, $(C_1-C_4)$alkylene-C(O)—$(C_5-C_{10})$heterocyclyl, $(C_1-C_4)$alkylene-C(O)—$(C_6-C_{10})$aryl, $(C_1-C_6)$alkylene-C(O)N[$(C_1-C_6)$alkyl]₂, $(C_1-C_6)$alkylene-C(O)NH—$(C_1-C_6)$alkyl, $(C_1-C_6)$alkylene-C(O)O—$(C_1-C_6)$alkyl, C(O)R'C(O)$(C_1-C_6)$alkyl, C(O)O—$(C_1-C_6)$alkyl, C(O)NH—$(C_1-C_6)$alkyl, C(O)N[$(C_1-C_6)$alkyl]₂, or C(O)$(C_1-C_6)$alkylene-R', or
$R_6$ and $R_6'$, together with the N-atom to which they are attached, form a $(C_5-C_{10})$heterocyclyl group.

In a further preferred embodiment, $R_6$ and $R_6'$ are independently of each other H, $(C_1-C_6)$alkyl, $(C_5-C_{10})$heterocyclyl, $(C_3-C_8)$cycloalkyl, $(C_6-C_{10})$aryl, $(C_1-C_4)$alkylene-$(C_3-C_8)$cycloalkyl, $(C_1-C_4)$alkylene-$(C_5-C_{10})$heterocyclyl, $(C_1-C_4)$alkylene-$(C_6-C_{10})$aryl, $(C_1-C_6)$alkylene-O—$(C_1-C_6)$alkyl, $(C_1-C_6)$alkylene-C(O)N[$(C_1-C_6)$alkyl]₂, $(C_1-C_6)$alkylene-C(O)NH—$(C_1-C_6)$alkyl, $(C_1-C_6)$alkylene-C(O)O—$(C_1-C_6)$alkyl, C(O)O—$(C_1-C_6)$alkyl, C(O)$(C_1-C_6)$alkyl, C(O)$(C_3-C_8)$cycloalkyl, C(O)NH—$(C_1-C_6)$alkyl, C(O)N[$(C_1-C_6)$alkyl]₂, C(O)$(C_1-C_6)$alkylene-$(C_3-C_8)$cycloalkyl, C(O)$(C_1-C_6)$alkylene-$(C_5-C_{10})$heterocyclyl, C(O)$(C_1-C_6)$alkylene-$(C_6-C_{10})$aryl, or $R_6$ and $R_6'$, together with the N-atom to which they are attached form a $(C_5-C_{10})$heterocyclyl group.

In a more preferred embodiment, $R_6$ is H, $(C_1-C_6)$alkyl, $(C_3-C_6)$cycloalkyl or $(C_1-C_4)$alkylene-$(C_3-C_6)$cycloalkyl, and
$R_6'$ is H, $(C_1-C_6)$alkyl, $(C_3-C_8)$cycloalkyl, $(C_5-C_{10})$heterocyclyl, $(C_6-C_{10})$aryl, $(C_1-C_4)$alkylene-$(C_3-C_8)$cycloalkyl, $(C_1-C_4)$alkylene-$(C_5-C_{10})$heterocyclyl, $(C_1-C_4)$alkylene-$(C_6-C_{10})$aryl, $(C_1-C_6)$alkylene-O—$(C_1-C_6)$alkyl, $(C_1-C_6)$alkylene-C(O)NH—$(C_1-C_6)$alkyl, $(C_1-C_6)$alkylene-C(O)N[$(C_1-C_6)$alkyl]₂, $(C_1-C_6)$alkylene-C(O)O—$(C_1-C_6)$alkyl, C(O)O—$(C_1-C_6)$alkyl, C(O)$(C_1-C_6)$alkyl, C(O)$(C_3-C_8)$cycloalkyl, C(O)NH—$(C_1-C_6)$alkyl, C(O)N[$(C_1-C_6)$alkyl]₂, C(O)$(C_1-C_6)$alkylene-$(C_3-C_8)$cycloalkyl, C(O)$(C_1-C_6)$alkylene-$(C_5-C_{10})$heterocyclyl, C(O)$(C_1-C_6)$alkylene-$(C_6-C_{10})$aryl, or
$R_6$ and $R_6'$, together with the N-atom to which they are attached, form a $(C_5-C_{10})$heterocyclyl group.

In a further more preferred embodiment, $R_6$ is H, $(C_1-C_6)$alkyl and $R_6'$ is H, $(C_1-C_6)$alkyl, $(C_3-C_8)$cycloalkyl, $(C_6-C_{10})$aryl, $(C_5-C_{10})$heterocyclyl, $(C_1-C_4)$alkylene-$(C_3-C_8)$cycloalkyl, $(C_1-C_4)$alkylene-$(C_5-C_{10})$heterocyclyl, $(C_1-C_6)$alkylene-$(C_6-C_{10})$aryl, $(C_1-C_4)$alkylene-O—$(C_1-C_4)$alkyl, $(C_1-C_4)$alkylene-C(O)N[$(C_1-C_4)$alkyl]₂, $(C_1-C_6)$alkylene-C(O)NH—$(C_1-C_6)$alkyl, C(O)$(C_1-C_6)$alkyl, C(O)$(C_1-C_6)$alkylene-$(C_5-C_{10})$heterocyclyl, or
$R_6$ and $R_6'$, together with the N-atom to which they are attached, form a $(C_5-C_{10})$heterocyclyl group.

In a further even more preferred embodiment, $R_6$ is H, $(C_1-C_6)$alkyl and $R_6'$ is
H,
$(C_1-C_6)$alkyl;
$(C_3-C_8)$cycloalkyl;
$(C_1-C_4)$alkylene-$(C_3-C_8)$cycloalkyl;
$(C_1-C_4)$alkylene-O—$(C_1-C_4)$alkyl;
$(C_1-C_4)$alkylene-C(O)N[$(C_1-C_4)$alkyl]₂;
$(C_1-C_4)$alkylene-$(C_5-C_{10})$heterocyclyl, or
$(C_1-C_4)$alkylene-$(C_6-C_{10})$aryl;
C(O)$(C_1-C_4)$alkyl;
C(O)$(C_1-C_4)$alkylene-$(C_5-C_{10})$heterocyclyl;
or $R_6$ and $R_6'$, together with the N-atom to which they are attached, form a $(C_5-C_6)$heterocyclyl group.

Preferably the formed heterocyclyl group is morpholino, piperidino, pyrrolidino or piperazino. More preferably the heterocyclyl group is morpholino or piperazino.

In a most preferred embodiment, $R_6$ is H, $(C_1-C_6)$alkyl and $R_6'$ is H, $(C_1-C_6)$alkyl or $(C_3-C_8)$cycloalkyl, In a further most preferred embodiment, $R_6$ is H and $R_6'$ is H, preferably unsubstituted $(C_1-C_6)$alkyl, or preferably unsubstituted $(C_3-C_8)$cycloalkyl. Especially preferred, $R_6$ and $R_6'$ are H.

As examples for these embodiments, $R_6$ or $R_6'$ are, independently from each other, hydrogen, methyl, ethyl, propyl, isopropyl, 3-methyl-butyl, 2-methyl-propyl, butyl, pentyl, 3,3,3-trifluoropropyl, 4,4,4-trifluorobutyl or a substituent selected from the group consisting of

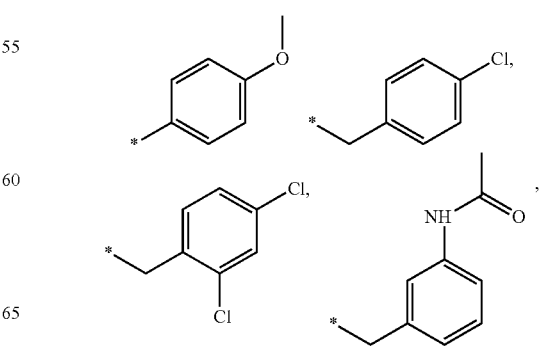

-continued

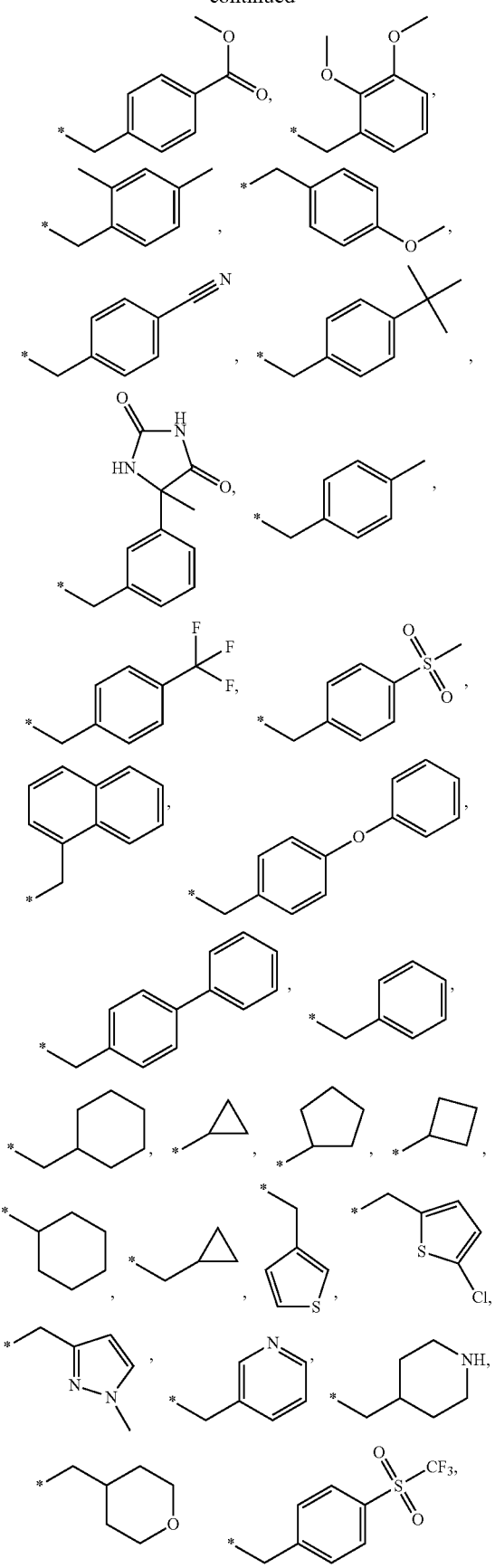

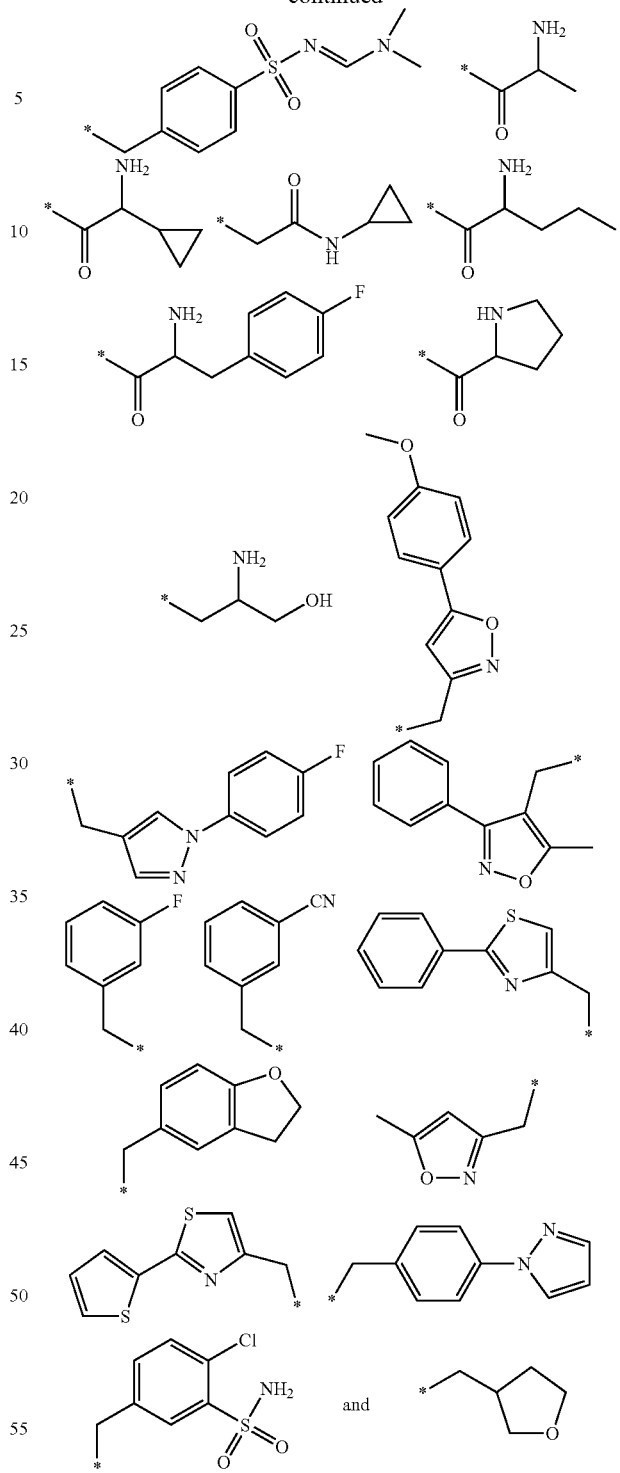

The asterisk (*) denotes where the bond is connected to the N-atom of the amine.

Preferably, $R_7$ is H, halogen, CN, $(C_1-C_6)$alkyl, O—$(C_1-C_6)$alkyl, $(C_2-C_6)$alkenyl, R' or $(C_1-C_6)$alkylene-$(C_3-C_8)$cycloalkyl. More preferred, $R_7$ is H, halogen, CN, $(C_1-C_4)$alkyl, O—$(C_1-C_4)$alkyl, $(C_2-C_4)$alkenyl, phenyl, cyclopropyl or $(C_5-C_6)$heteroaryl. Most preferably, $R_7$ is H, fluoro, chloro, bromo, methyl, ethyl, methoxy, phenyl, nitrile, cyclopropyl, thienyl or vinyl, most especially preferred $R_7$ is H, fluoro, chloro, methyl or methoxy. More particular preferred $R_7$ is H or chloro, most particular preferred $R_7$ is H.

$R_8$ is preferably H, halogen or $(C_1-C_4)$alkyl. More preferred, $R_8$ is H, Cl, F, methyl or ethyl. Most preferred $R_8$ is H.

Preferably, $R_2$ is
R',
$(C_7-C_8)$alkyl,
$(C_1-C_6)$alkylene-R',
$(C_2-C_6)$alkenyl,
$(C_1-C_6)$alkylene-C(O)NH$_2$,
$(C_1-C_6)$alkylene-C(O)NH—R',
$(C_1-C_6)$alkylene-C(O)NH—$(C_1-C_6)$alkyl,
$(C_1-C_6)$alkylene-C(O)N[$(C_1-C_6)$alkyl]$_2$,
$(C_1-C_6)$alkylene-C(O)N[R']$_2$;
$(C_1-C_6)$alkylene-C(O)O—$(C_1-C_6)$alkyl,
C(O)NH—$(C_1-C_6)$alkyl,
C(O)NHR',
C(O)—NH—$(C_2-C_6)$alkenyl,
C(O)—NH—$(C_2-C_6)$alkynyl,
C(O)—NH($C_1-C_6$)alkylene-R',
C(O)N[$(C_1-C_6)$alkyl]R'
C(O)N[$(C_1-C_6)$alkyl]$_2$,
C(O)—$(C_1-C_6)$alkylene-R', or
C(O)O($C_1-C_6$)alkylene-R'; or
$R_2$ is $(C_1-C_6)$alkyl, provided that in said alkyl residue at least one hydrogen is substituted by OH, OCH$_3$, COOH, COOCH$_3$, NH$_2$, NHCH$_3$, N(CH$_3$)$_2$, CONH$_2$, CONHCH$_3$ or CON(CH$_3$)$_2$; or
$R_2$ is a $(C_1-C_4)$alkylene bound to the cycloalkyl amine, in which the $(C_1-C_4)$ alkylene forms a second bond to a different carbon atom of the cycloalkyl amine ring and forms, together with carbon atoms of cycloalkyl amine, a second, 4-8 membered ring.

More preferably, $R_2$ is
R',
$(C_1-C_6)$alkylene-R',
$(C_2-C_6)$alkenyl,
$(C_1-C_6)$alkylene-C(O)NH$_2$,
$(C_1-C_6)$alkylene-C(O)NH—R',
$(C_1-C_6)$alkylene-C(O)NH—$(C_1-C_6)$alkyl,
C(O)NH—$(C_1-C_6)$alkyl,
C(O)NHR', or
C(O)—NH($C_1-C_6$)alkylene-R', or
$R_2$ is $(C_1-C_3)$alkyl, provided that in said alkyl residue at least one hydrogen is substituted by OH, OCH$_3$, COOH, COOCH$_3$, NH$_2$, NHCH$_3$, N(CH$_3$)$_2$, CONH$_2$, CONHCH$_3$ or CON(CH$_3$)$_2$; or
$R_2$ is a $(C_1-C_4)$alkylene bound to the cycloalkyl amine, in which the $(C_1-C_4)$ alkylene forms a second bond to a different carbon atom of the cycloalkyl amine ring and forms, together with carbon atoms of the cycloalkyl amine, a second, 4-8 membered ring.

Most preferably, $R_2$ is
R',
$(C_1-C_6)$alkylene-R',
$(C_2-C_6)$alkenyl,
$(C_1-C_6)$alkylene-C(O)NH—R',
$(C_1-C_6)$alkylene-C(O)NH—$(C_1-C_6)$alkyl,
C(O)NH—$(C_1-C_6)$alkyl,
C(O)NHR',
C(O)—NH—$(C_2-C_6)$alkenyl, or
C(O)—NH($C_1-C_6$)alkylene-R', or
$R_2$ is a $(C_1-C_4)$alkylene bound to the cycloalkyl amine, in which the $(C_1-C_4)$ alkylene forms a second bond to a different carbon atom of the cycloalkyl amine ring and forms, together with carbon atoms of the cycloalkyl amine, a second, 4-8 membered ring.

Even more preferred $R_2$ is phenyl, which is unsubstituted or substituted one or two times by halogen, OH, OMe or CF$_3$; $(C_3-C_8)$cycloalkyl, which is unsubstituted, or is $(C_2-C_6)$alkenyl, preferably allyl, or $R_2$ is a $(C_1-C_4)$alkylene bound to the cycloalkyl amine, in which the $(C_1-C_4)$ alkylene forms a second bond to a different carbon atom of the cycloalkyl amine ring and forms, together with a carbon atom of the cycloalkyl amine, a second, 4-8 membered ring.

$R_2$ may be bound to any carbon atom of the ring including the position where the linker group L is bound, preferably at the carbon atom where the —NR$_6$, R$_6$' group is bound.

As examples for these embodiments, $R_2$ is

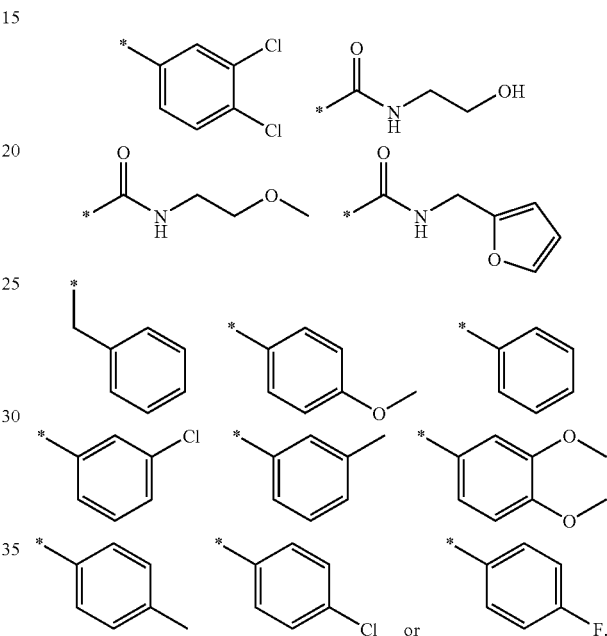

In other Examples R2 is

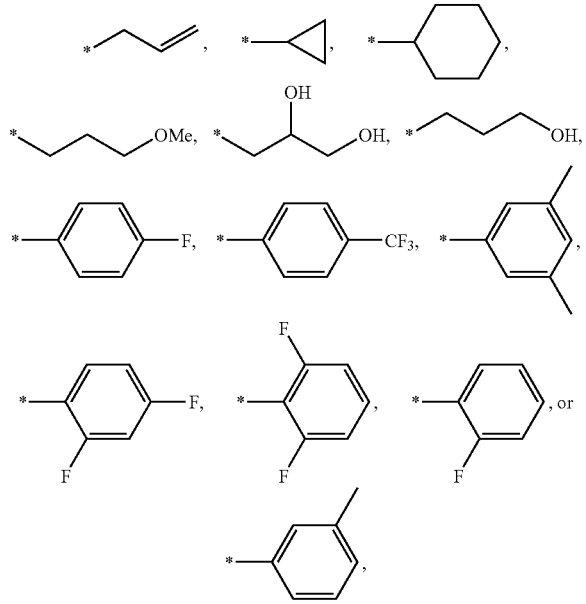

The asterisk (*) denotes where the bond is connected to the C-atom of the ring.

Examples for the embodiments wherein $R_2$ is a $C_1$-$C_4$ alkylene, which creates a second ring system with the cyclic amine, comprise

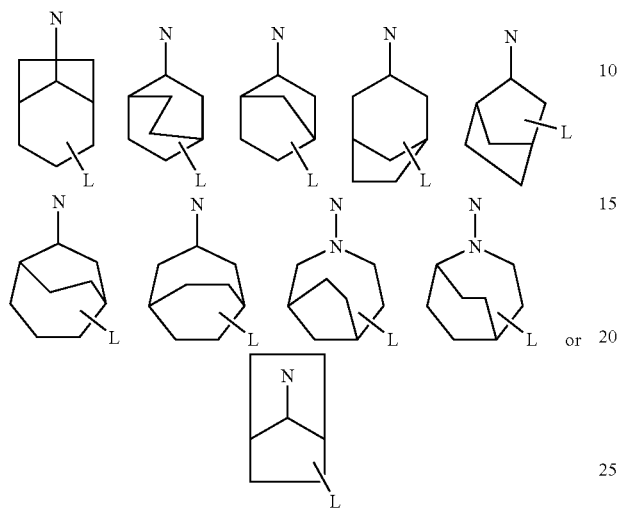

Other examples are

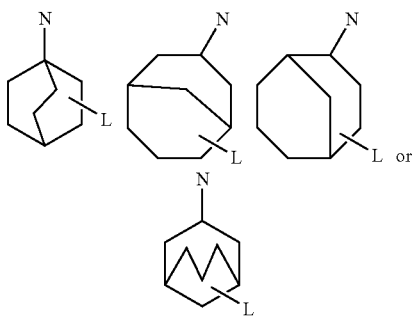

In a particular embodiment the created ring system is

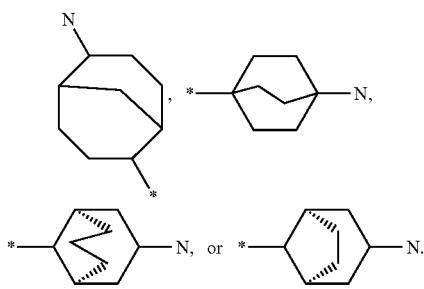

The asterisk (*) denotes the bond to L.

The amino group in the created bicyclic cycloalkylamine residue is substituted by R6 and R6' residues as defined above in the general formula (I).

Preferably, n is 1, 2 or 3. More preferred, n is 1 or 2. Most preferred n is 1.

Preferably m is 2, 3 or 4. More preferred m is 3. In a further embodiment m is 1, 2, 4 or 5.

Preferably r is 0 or 1, more preferred r is 0.

The linker group L may be bound to the ring in any position via a ring carbon atom. In a preferred embodiment, m is 3 and L is attached to the 4-position of the amino cyclohexane ring

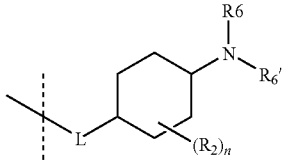

or L is attached to the 3-position of the amino cyclohexane ring

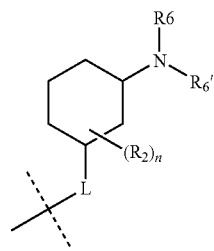

in all their stereochemical forms.

In an especially preferred embodiment, L is attached to the 4-position of the amino cyclohexane ring.

In another embodiment, L is O—$(CH_2)p$. In a further embodiment of L, L is $S(CH_2)p$, $S(O)(CH_2)p$ or $SO_2(CH_2)p$. In another embodiment L is $NH(CH_2)p$, $N(C_1$-$C_6)$alkyl-$(CH_2)p$, $N(C_3$-$C_6)$cycloalkyl-$(CH_2)p$, $N[CO(C_1$-$C_6)$alkyl]-$(CH_2)p$, $N[(C_1$-$C_3)$alkylene-aryl]-$(CH_2)p$ or $N[(C_1$-$C_3)$alkylene-$(C_5$-$C_6)$heterocyclyl]-$(CH_2)p$ with $NH(CH_2)p$, $N(C_1$-$C_6)$alkyl-$(CH_2)p$ being more preferred. A preferred $N(C_1$-$C_6)$ alkyl is $N(C_1$-$C_4)$alkyl, more preferably $NCH_3$ or $NCH_2CH_3$ with $NCH_3$ being more preferred. Even more preferred L is O—$(CH_2)p$, $S(CH_2)p$ or $NH(CH_2)p$. Most preferred L is O, S or NH with O being especially preferred.

Preferably p is 0, 1, 2, or 3, more preferred 0 or 1, with 0 being most preferred;

More preferably, m is 3 and L is O, S or NH and is attached to the 4-position of the amino cyclohexane ring.

In residues $R_2$ to $R_8$ an alkyl or alkylene can optionally be substituted one or more times by halogen. Preferably alkyl or alkylene is substituted one to three times by halogen selected from chloro or bromo but may be substituted by fluoro once or more, e.g. being perfluorinated. Preferably halogen is fluoro. More preferred an alkyl or alkylene is not halogenated.

In residues $R_2$, $R_4$, $R_5$, $R_6$, $R_6'$, $R_7$ and $R_8$ as alkyl, alkylene or cycloalkyl can optionally be substituted one or more times by a group selected independently from OH, $OCH_3$, COOH, $COOCH_3$, $NH_2$, $NHCH_3$, $N(CH_3)_2$, $CONH_2$, $CONHCH_3$ or $CON(CH_3)_2$.

If substituted, the number of substituents is preferably between 1, 2, 3 or 4, more preferably 1 or 2 with 1 being even more preferred. Preferably an alkylene or cycloalkyl is not substituted. More preferably an alkyl, alkylene or cycloalkyl is not substituted. Preferably alkyl, alkylene or cycloalkyl in $R_4$, $R_5$, $R_7$ and $R_8$ are not substituted. In a further embodiment alkyl, alkylene or cycloalkyl in $R_4$, $R_5$, $R_6$, $R_6'$, $R_7$ and $R_8$ are not substituted.

In preferred embodiments of the present invention one or more or all of the groups contained in the compounds of formula (I) can independently of each other have any of the preferred, more preferred or most preferred definitions of the groups specified above or any one or some of the specific denotations which are comprised by the definitions of the groups and specified above, all combinations of preferred definitions, more preferred or most preferred and/or specific denotations being a subject of the present invention. Also with respect to all preferred embodiments the invention includes the compounds of the formula (I) in all stereoisomeric forms and mixtures of stereoisomeric forms in all ratios, and their pharmaceutically acceptable salts.

The term "*-" in the exemplified substituents vide supra marks the point where the substituent is attached, which means, for example, for a $R_3$ substituent

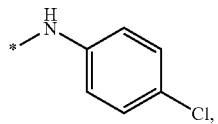

with r=0 and m is 3, a compound of the formula

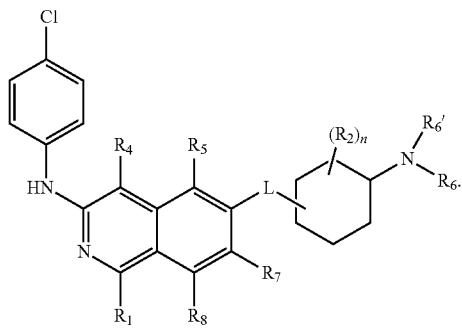

A preferred embodiment is a compound of the formula (I) wherein
$R_1$ is H or OH
$R_2$ is
R',
$(C_7-C_8)$alkyl,
$(C_1-C_6)$alkylene-R',
$(C_2-C_6)$alkenyl,
$(C_1-C_6)$alkylene-C(O)NH$_2$,
$(C_1-C_6)$alkylene-C(O)NH—R',
$(C_1-C_6)$alkylene-C(O)NH—$(C_1-C_6)$alkyl,
$(C_1-C_6)$alkylene-C(O)N[$(C_1-C_6)$alkyl]$_2$,
$(C_1-C_6)$alkylene-C(O)N[R']$_2$;
$(C_1-C_6)$alkylene-C(O)O—$(C_1-C_6)$alkyl,
C(O)NH—$(C_1-C_6)$alkyl,
C(O)NHR',
C(O)—NH—$(C_2-C_6)$alkenyl,
C(O)—NH—$(C_2-C_6)$alkynyl,
C(O)—NH$(C_1-C_6)$alkylene-R',
C(O)N[$(C_1-C_6)$alkyl]R'
C(O)N[$(C_1-C_6)$alkyl]$_2$,
C(O)—$(C_1-C_6)$alkylene-R', or
C(O)O$(C_1-C_6)$alkylene-R'; or
$R_2$ is $(C_1-C_6)$alkyl, provided that in said alkyl residue at least one hydrogen is substituted by OH, OCH$_3$, COOH, COOCH$_3$, NH$_2$, NHCH$_3$, N(CH$_3$)$_2$, CONH$_2$, CONHCH$_3$ or CON(CH$_3$)$_2$; or $R_2$ is a $(C_1-C_4)$alkylene bound to the cycloalkyl amine, in which the $(C_1-C_4)$ alkylene forms a second bond to a different carbon atom of the cycloalkyl amine ring and forms, together with carbon atoms of cycloalkyl amine, a second, 4-8 membered ring;
$R_3$ is H, halogen, $(C_1-C_4)$alkylene-R', O—R" or NHR";
$R_4$ is H, halogen or $(C_1-C_6)$alkyl;
$R_5$ is H, $(C_1-C_6)$alkyl, halogen, CN, $(C_2-C_6)$alkenyl, $(C_6-C_{10})$aryl, NH—$(C_6-C_{10})$aryl, $(C_1-C_6)$alkylene-$(C_6-C_{10})$aryl, $(C_5-C_{10})$heterocyclyl or $(C_1-C_6)$alkylene-$(C_5-C_{10})$heterocyclyl;
$R_6$ and $R_6$' are independently of each other H, R', $(C_1-C_8)$alkyl, $(C_1-C_6)$alkylene-R', $(C_1-C_6)$alkylene-O—$(C_1-C_6)$alkyl, $(C_1-C_6)$alkylene-O—R', $(C_1-C_6)$alkylene-CH[R']$_2$, $(C_1-C_6)$alkylene-C(O)NH$_2$, $(C_1-C_6)$alkylene-C(O)NH—R', $(C_1-C_6)$alkylene-C(O)N[$(C_1-C_4)$alkyl]$_2$, $(C_1-C_6)$alkylene-C(O)N[R']$_2$, C(O)O—$(C_1-C_6)$alkyl, C(O)$(C_1-C_6)$alkyl, C(O)$(C_3-C_8)$cycloalkyl, C(O)$(C_5-C_{10})$heterocyclyl, C(O)NH—$(C_1-C_6)$alkyl, C(O)N[$(C_1-C_6)$alkyl]$_2$, C(O)—$(C_1-C_6)$alkylene-$C_3-C_8$)cycloalkyl, C(O)$(C_1-C_6)$alkylene-$(C_5-C_{10})$heterocyclyl, C(O)$(C_1-C_6)$alkylene-$(C_6-C_{10})$aryl,
or $R_6$ and $R_6$', together with the N-atom to which they are attached, form a $(C_5-C_6)$heterocyclyl group.
$R_7$ is H, halogen, CN, $(C_1-C_6)$alkyl, O—$(C_1-C_6)$alkyl, $(C_2-C_6)$alkenyl or R';
$R_8$ is H, halogen or $(C_1-C_6)$alkyl;
m is 2, 3 or 4
n is 1, 2 or 3, and
r is 0, 1 or 2
L is O—(CH$_2$)p, S(CH$_2$)p, NH(CH$_2$)p or N(C$_1$-C$_6$)alkyl-(CH$_2$)p; and
p is 0, 1 or 2; or
stereoisomeric form thereof and/or tautomeric form thereof and/or pharmaceutically acceptable salt thereof.

A further preferred embodiment is a compound of the formula (I) wherein
$R_1$ is H or OH;
$R_2$ is
R',
$(C_1-C_6)$alkylene-R',
$(C_2-C_6)$alkenyl,
$(C_1-C_6)$alkylene-C(O)NH$_2$,
$(C_1-C_6)$alkylene-C(O)NH—R',
$(C_1-C_6)$alkylene-C(O)NH—$(C_1-C_6)$alkyl,
C(O)NH—$(C_1-C_6)$alkyl,
C(O)NHR',
C(O)—NH—$(C_2-C_6)$alkynyl, or
C(O)—NH$(C_1-C_6)$alkylene-R', or
$R_2$ is $(C_1-C_3)$alkyl, provided that in said alkyl residue at least one hydrogen is substituted by OH, OCH$_3$, COOH, COOCH$_3$, NH$_2$, NHCH$_3$, N(CH$_3$)$_2$, CONH$_2$, CONHCH$_3$ or CON(CH$_3$)$_2$; or
$R_2$ is a $(C_1-C_4)$alkylene bound to the cycloalkyl amine, in which the $(C_1-C_4)$ alkylene forms a second bond to a different carbon atom of the cycloalkyl amine ring and forms, together with carbon atoms of cycloalkyl amine, a second, 4-8 membered ring;
$R_3$ is H, halogen or NHR", wherein R" is defined as above;
$R_4$ is H, halogen or $(C_1-C_4)$alkyl;
$R_5$ is H, $(C_1-C_6)$alkyl, halogen, $(C_2-C_4)$alkenyl, $(C_6-C_{10})$aryl, $(C_1-C_6)$alkylene-$(C_6-C_{10})$aryl or $(C_5-C_{10})$heterocyclyl;
$R_6$ and $R_6$' are independently of each other H, $(C_3-C_8)$cycloalkyl, $(C_1-C_8)$alkyl, $(C_1-C_6)$alkylene-O—$(C_1-C_6)$alkyl, $(C_1-C_3)$alkylene-R'; C(O)$(C_1-C_6)$alkyl, C(O)$(C_3-C_8)$cycloalkyl, C(O)$(C_5-C_{10})$heterocyclyl, C(O)$(C_1-C_6)$alkylene-$C_3-C_8$)cycloalkyl, C(O)$(C_1-C_6)$alkylene-$(C_5-C_{10})$heterocyclyl or C(O)$(C_1-C_6)$alkylene-$(C_6-C_{10})$aryl;

R₇ is H, halogen, CN, (C₁-C₆)alkyl, O—(C₁-C₆)alkyl, (C₂-C₆)alkenyl or R';
R₈ is H, halogen or (C₁-C₆)alkyl;
m is 2, 3 or 4
n is 1, 2 or 3;
r is 0, 1 or 2; and
L is O—(CH₂)p, S(CH₂)p or NH(CH₂)p,
p is 0 or 1; or
stereoisomeric form thereof and/or tautomeric form thereof and/or pharmaceutically acceptable salt thereof.

An especially preferred embodiment is a compound of the formula (I) wherein
R₁ is H or OH;
R₂ is
C₁-C₆)alkylene-R',
(C₂-C₆)alkenyl,
(C₁-C₆)alkylene-C(O)NH—R',
(C₁-C₆)alkylene-C(O)NH—(C₁-C₆)alkyl,
C(O)NH—(C₁-C₆)alkyl,
C(O)NHR',
C(O)—NH—(C₂-C₆)alkynyl, or
C(O)—NH(C₁-C₆)alkylene-R', or
R₂ is a (C₁-C₄)alkylene bound to the cycloalkyl amine, in which the (C₁-C₄) alkylene forms a second bond to a different carbon atom of the cycloalkyl amine ring and forms, together with carbon atoms of cycloalkyl amine, a second, 4-8 membered ring;
R₃ is H, NH—(C₅-C₆)heteroaryl or NH-phenyl;
R₄ is H, halogen or (C₁-C₄)alkyl;
R₅ is H, (C₁-C₄)alkyl, halogen, (C₂-C₄)alkenyl, (C₆-C₁₀)aryl, (C₁-C₂)alkyl-(C₆-C₁₀)aryl or (C₅-C₆)heteroaryl;
R₆ is H, (C₃-C₆)cycloalkyl or (C₁-C₄)alkyl;
R₆' is H, (C₃-C₈)cycloalkyl, (C₁-C₈)alkyl, (C₁-C₃)alkylene-R', C(O)O—(C₁-C₆)alkyl, C(O)(C₁-C₆)alkyl, C(O)(C₃-C₆)cycloalkyl, C(O)(C₅-C₆)heterocyclyl, C(O)(C₁-C₃)alkylene-(C₃-C₆)cycloalkyl, C(O)(C₁-C₃)alkylene-(C₅-C₆)heterocyclyl, or C(O)(C₁-C₃)alkylene-phenyl;
R₇ is H, halogen, CN, (C₁-C₄)alkyl, O—(C₁-C₄)alkyl, (C₂-C₄)alkenyl, phenyl, cyclopropyl, (C₅-C₆)heteroaryl;
R₈ is H, halogen or (C₁-C₄)alkyl;
m is 3
n is 1;
r is 0 or 1
and
L is O, S or NH; or
stereoisomeric form thereof and/or tautomeric form thereof and/or pharmaceutically acceptable salt thereof.

In an embodiment the present invention relates to a compound of formula (I) selected from the group consisting of
6-(4-Allyl-4-amino-cyclohexyloxy)-7-chloro-2H-isoquinolin-1-one (20),
6-(4-Allyl-4-amino-cyclohexyloxy)-2H-isoquinolin-1-one (21)
6-(4-amino-4-benzyl-cyclohexyloxy)-7-chloro-2H-isoquinolin-1-one (69)
6-(4-Amino-4-phenyl-cyclohexyloxy)-7-chloro-2H-isoquinolin-1-one (71)
6-(4-Aminomethyl-4-phenyl-cyclohexyloxy)-7-chloro-2H-isoquinolin-1-one (108)
6-[4-Aminomethyl-4-(4-chloro-phenyl)-cyclohexyloxy]-7-chloro-2H-isoquinolin-1-one (109)
6-[4-Aminomethyl-4-(3-chloro-phenyl)-cyclohexyloxy]-7-chloro-2H-isoquinolin-1-one (110)
6-[4-Aminomethyl-4-(3-methyl-phenyl)-cyclohexyloxy]-7-chloro-2H-isoquinolin-1-one (111)
6-[4-Aminomethyl-4-(3,4-dimethoxy-phenyl)-cyclohexyloxy]-7-chloro-2H-isoquinolin-1-one (112)
6-[4-Aminomethyl-4-(4-fluoro-phenyl)-cyclohexyloxy]-7-chloro-2H-isoquinolin-1-one (113)
6-[4-Aminomethyl-4-(4-methoxy-phenyl)-cyclohexyloxy]-7-chloro-2H-isoquinolin-1-one (114)
6-[4-Aminomethyl-4-(4-methyl-phenyl)-cyclohexyloxy]-7-chloro-2H-isoquinolin-1-one (115)
6-[4-Aminomethyl-4-(3,4-chloro-phenyl)-cyclohexyloxy]-7-chloro-2H-isoquinolin-1-one (116) and
C-[4-(7-Chloro-isoquinolin-6-yloxy)-1-phenyl-cyclohexyl]-methylamine (120),
stereoisomeric form thereof and/or tautomeric form thereof and/or pharmaceutically acceptable salt thereof.

In an embodiment the present invention relates to a compound of formula (I) selected from the group consisting of
6-(4-Allyl-4-amino-cyclohexyloxy)-4,7-dimethyl-2H-isoquinolin-1-one (22),
6-(cis-4-Allyl-4-amino-cyclohexyloxy)-7-methyl-2H-isoquinolin-1-one (24),
6-(cis-4-Amino-4-cyclopropyl-cyclohexyloxy)-7-chloro-2H-isoquinolin-1-one (41),
6-(trans-4-amino-4-cyclopropyl-cyclohexyloxy)-7-chloro-2H-isoquinolin-1-one (42),
6-(trans-4-amino-4-cyclopropyl-cyclohexyloxy)-7-methyl-2H-isoquinolin-1-one (43),
6-(cis-1-amino-bicyclohexyl-4-yloxy)-7-chloro-2H-isoquinolin-1-one (44),
6-(trans-1-amino-bicyclohexyl-4-yloxy)-7-chloro-2H-isoquinolin-1-one (45),
6-(5-allyl-5-amino-cyclooctyloxy)-7-chloro-2H-isoquinolin-1-one (46),
6-[cis-4-amino-4-(3-methoxy-propyl)-cyclohexyloxy]-7-chloro-2H-isoquinolin-1-one (47),
6-[trans-4-amino-4-(3-methoxy-propyl)-cyclohexyloxy]-7-chloro-2H-isoquinolin-1-one (48),
6-(trans-4-Benzylamino-4-cyclopropyl-cyclohexyloxy)-7-chloro-2H-isoquinolin-1-one (49),
7-chloro-6-(trans-4-cyclopropyl-4-isopropylamino-cyclohexyloxy)-2H-isoquinolin-1-one (50),
7-chloro-6-(4-cyclopropyl-4-ethylamino-cyclohexyloxy)-2H-isoquinolin-1-one (51),
6-[cis-4-Amino-4-(3-hydroxy-propyl)-cyclohexyloxy]-7-chloro-2H-isoquinolin-1-one (54),
6-[trans-4-amino-4-(3-hydroxy-propyl)-cyclohexyloxy]-7-chloro-2H-isoquinolin-1-one (55),
6-[4-amino-4-(2,3-dihydroxy-propyl)-cyclohexyloxy]-7-chloro-2H-isoquinolin-1-one (57),
6-[5-Amino-5-(3-hydroxy-propyl)-cyclooctyloxy]-7-chloro-2H-isoquinolin-1-one (60),
6-[5-Amino-5-(3-methoxy-propyl)-cyclooctyloxy]-7-chloro-2H-isoquinolin-1-one (62),
6-[5-Amino-5-(2,3-dihydroxy-propyl)-cyclooctyloxy]-7-chloro-2H-isoquinolin-1-one (64),
6-[cis-4-Amino-4-(4-fluoro-phenyl)-cyclohexyloxy]-7-chloro-2H-isoquinolin-1-one (81),
6-(cis-4-Amino-4-phenyl-cyclohexyloxy)-7-chloro-2H-isoquinolin-1-one (82),
6-(trans-4-Amino-4-phenyl-cyclohexyloxy)-7-chloro-2H-isoquinolin-1-one (83),
6-[cis-4-Amino-4-(4-trifluoromethyl-phenyl)-cyclohexyloxy]-7-chloro-2H-isoquinolin-1-one (84),
6-[cis-4-Amino-4-(4-fluoro-phenyl)-cyclohxyloxy]-4-benzyl-7-methyl-2H-isoquinolin-1-one (85),
6-[cis-4-Amino-4-(3,5-dimethyl-phenyl)-cyclohexyloxy]-7-chloro-2H-isoquinolin-1-one (86),
6-[cis-4-Amino-4-(3,5-dimethyl-phenyl)-cyclohexyloxy]-7-methyl-2H-isoquinolin-1-one (87), 6-[cis-4-Amino-4-(2,4-difluoro-phenyl)-cyclohexyloxy]-7-chloro-2H-isoquinolin-1-one (88),
6-[cis-4-Amino-4-(2,6-difluoro-phenyl)-cyclohexyloxy]-7-chloro-2H-isoquinolin-1-one (89),
6-[cis-4-Amino-4-(2,6-difluoro-phenyl)-cyclohexyloxy]-7-methyl-2H-isoquinolin-1-one (90),
6-[cis-4-Amino-4-(4-fluoro-phenyl)-cyclohexyloxy]-7-methyl-2H-isoquinolin-1-one (91),
6-[cis-4-Amino-4-(2,6-difluoro-phenyl)-cyclohexyloxy]-4-benzyl-7-methyl-2H-isoquinolin-1-one (92),
6-[cis-4-Amino-4-(2,4-difluoro-phenyl)-cyclohexyloxy]-7-methyl-2H-isoquinolin-1-one (93),
6-[cis-4-Amino-4-(2-fluoro-phenyl)-cyclohexyloxy]-7-chloro-2H-isoquinolin-1-one (94),
6-[cis-4-Amino-4-(2-fluoro-phenyl)-cyclohexyloxy]-7-methyl-2H-isoquinolin-1-one (95),
6-[cis-4-Amino-4-(3,5-dimethyl-phenyl)-cyclohexyloxy]-7-chloro-2H-isoquinolin-1-one (96),
6-((1R,5R)-6-Amino-bicyclo[3.3.1]non-2-yloxy)-7-chloro-2H-isoquinolin-1-one (103),
6-((1R,5R)-6-Amino-bicyclo[3.3.1]non-2-yloxy)-7-methyl-2H-isoquinolin-1-one (104),
6-((1R,5R)-6-Amino-bicyclo[3.3.1]non-2-yloxy)-4-benzyl-7-methyl-2H-isoquinolin-1-one (105),
6-(4-Amino-bicyclo[2.2.2]oct-1-yloxy)-7-chloro-2H-isoquinolin-1-one (106),
6-{[(3-endo)-3-aminobicyclo[3.3.1]non-9-yl]oxy}-7-chloroisoquinolin-1(2H)-one (126),
6-{[(3-Exo)-3-aminobicyclo[3.3.1]non-9-yl]oxy}-7-chloroisoquinolin-1(2H)-one (131),
6-{[(3-Endo,8-syn)-3-aminobicyclo[3.2.1]oct-8-yl]oxy}-7-chloroisoquinolin-1(2H)-one (133), and
6-{[(3-endo,8-anti)-3-aminobicyclo[3.2.1]oct-8-yl]oxy}-7-chloroisoquinolin-1(2H)-one (134), or
stereoisomeric form thereof and/or tautomeric form thereof and/or pharmaceutically acceptable salt thereof.

As in any embodiment of the invention, in the preceding embodiments which contain preferred, more preferred, most preferred or exemplary definitions of compounds according to the invention, one or more or all of the groups can have any of its preferred, more preferred, most preferred definitions specified above or any one or some of the specific denotations which are comprised by its definitions and are specified above.

Isoquinoline substitution pattern is numbered according to IUPAC rules:

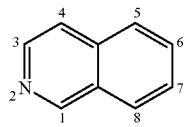

All references to "compound(s) of formula (I)" hereinafter refer to compound(s) of the formula (I), (II) (III), (III') and (IV) as described above, and their pharmaceutically acceptable salts, and/or to their stereoisomeric forms, polymorphs and solvates. Physiologically functional derivatives as described herein are also included.

Pharmaceutically acceptable salts of compounds of the formula (I) mean both their organic and inorganic salts as described in Remington's Pharmaceutical Sciences (17th edition, page 1418 (1985)). Because of the physical and chemical stability and the solubility, preference is given for acidic groups inter alia to sodium, potassium, calcium and ammonium salts; preference is given for basic groups inter alia to salts of maleic acid, fumaric acid, succinic acid, malic acid, tartaric acid, methylsulfonic acid, hydrochloric acid, sulfuric acid, phosphoric acid or of carboxylic acids or sulfonic acids, for example as hydrochlorides, hydrobromides, phosphates, sulfates, methanesulfonates, acetates, lactates, maleates, fumarates, malates, gluconates, and salts of amino acids, of natural bases or carboxylic acids. The preparation of pharmaceutically acceptable salts from compounds of the formula (I) which are capable of salt formation, including their stereoisomeric forms, takes place in a manner known per se. The compounds of the formula (I) form stable alkali metal, alkaline earth metal or optionally substituted ammonium salts with basic reagents such as hydroxides, carbonates, bicarbonates, alcoholates and ammonia or organic bases, for example trimethyl- or triethylamine, ethanolamine, diethanolamine or triethanolamine, trometamol or else basic amino acids, for example lysine, ornithine or arginine. Where the compounds of the formula (I) have basic groups, stable acid addition salts can also be prepared with strong acids. Suitable pharmaceutically acceptable acid addition salts of the compounds of the invention are salts of inorganic acids such as hydrochloric acid, hydrobromic, phosphoric, metaphosphoric, nitric and sulfuric acid, and of organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic and tartaric acid. The hydrochloride salt is a preferred salt.

Salts with a pharmaceutically unacceptable anion such as, for example, trifluoroacetate likewise belong within the framework of the invention as useful intermediates for the preparation or purification of pharmaceutically acceptable salts and/or for use in nontherapeutic, for example in vitro, applications.

The term "physiologically functional derivative" used herein refers to any physiologically tolerated derivative of a compound of the formula (I) of the invention, for example an N-oxide, which on administration to a mammal such as, for example, a human is able to form (directly or indirectly) a compound of the formula (I) or an active metabolite thereof.

Physiologically functional derivatives include prodrugs of the compounds of the invention, as described, for example, in H. Okada et al., Chem. Pharm. Bull. 1994, 42, 57-61. Such prodrugs can be metabolized in vivo to a compound of the invention. These prodrugs may themselves be active or not.

The invention relates to compounds of the formula (I) in the form of their stereoisomeric forms, which include racemates, racemic mixtures, pure enantiomers and diastereomers and mixtures thereof.

The compounds of the invention may also exist in various polymorphous forms, for example as amorphous and crystalline polymorphous forms. All polymorphous forms of the compounds of the invention belong within the framework of the invention and are a further aspect of the invention.

If radicals or substituents may occur more than once in the compounds of the formula (I), they may all, independently of one another, have the stated meaning and be identical or different.

The present invention therefore also relates to the compounds of the formula (I) and/or their pharmaceutically acceptable salts and/or their prodrugs for use as pharmaceuticals (or medicaments), to the use of the compounds of the formula (I) and/or their pharmaceutically acceptable salts and/or their prodrugs for the production of pharmaceuticals for the treatment and/or prevention of diseases associated with Rho-kinase and/or Rho-kinase mediated phosphorylation of myosin light chain phosphatase, i.e. for the treatment and/or prevention of hypertension, pulmonary hypertension, ocular hypertension, retinopathy, and glaucoma, peripheral circulatory disorder, peripheral occlusive arterial disease (PAOD), coronary heart disease, angina pectoris, heart hypertrophy, heart failure, ischemic diseases, ischemic organ failure (end organ damage), fibroid lung, fibroid liver, liver failure, nephropathy, including hypertension-induced, non-hypertension-induced, and diabetic nephropathies, renal failure, fibroid kidney, renal glomerulosclerosis, organ hypertrophy, asthma, chronic obstructive pulmonary disease (COPD), adult respiratory distress syndrome, thrombotic disorders, stroke, cerebral vasospasm, cerebral ischemia, pain, e.g. neuropathic pain, neuronal degeneration, spinal cord injury, Alzheimer's disease, premature birth, erectile dysfunction, endocrine dysfunctions, arteriosclerosis, prostatic hypertrophy, diabetes and complications of diabetes, metabolic syndrome, blood vessel restenosis, atherosclerosis, inflammation, autoimmune diseases, AIDS, osteopathy such as osteoporosis, infection of digestive tracts with bacteria, sepsis, cancer development and progression, e.g. cancers of the breast, colon, prostate, ovaries, brain and lung and their metastases.

The present invention furthermore relates to pharmaceutical preparations (or pharmaceutical compositions) which contain an effective amount of at least one compound of the formula (I) and/or its pharmaceutically acceptable salts and a pharmaceutically acceptable carrier, i.e. one or more pharmaceutically acceptable carrier substances (or vehicles) and/or additives (or excipients).

The pharmaceuticals can be administered orally, for example in the form of pills, tablets, lacquered tablets, coated tablets, granules, hard and soft gelatin capsules, solutions, syrups, emulsions, suspensions or aerosol mixtures. Administration, however, can also be carried out rectally, for example in the form of suppositories, or parenterally, for example intravenously, intramuscularly or subcutaneously, in the form of injection solutions or infusion solutions, microcapsules, implants or rods, or percutaneously or topically, for example in the form of ointments, solutions or tinctures, or in other ways, for example in the form of aerosols or nasal sprays.

The pharmaceutical preparations according to the invention are prepared in a manner known per se and familiar to one skilled in the art, pharmaceutically acceptable inert inorganic and/or organic carrier substances and/or additives being used in addition to the compound(s) of the formula (I) and/or its (their) pharmaceutically acceptable salts and/or its (their) prodrugs. For the production of pills, tablets, coated tablets and hard gelatin capsules it is possible to use, for example, lactose, corn starch or derivatives thereof, talc, stearic acid or its salts, etc. Carrier substances for soft gelatin capsules and suppositories are, for example, fats, waxes, semisolid and liquid polyols, natural or hardened oils, etc. Suitable carrier substances for the production of solutions, for example injection solutions, or of emulsions or syrups are, for example, water, saline, alcohols, glycerol, polyols, sucrose, invert sugar, glucose, vegetable oils, etc. Suitable carrier substances for microcapsules, implants or rods are, for example, copolymers of glycolic acid and lactic acid. The pharmaceutical preparations normally contain about 0.5 to about 90% by weight of the compounds of the formula (I) and/or their pharmaceutically acceptable salts and/or their prodrugs. The amount of the active ingredient of the formula (I) and/or its pharmaceutically acceptable salts and/or its prodrugs in the pharmaceutical preparations normally is from about 0.5 to about 1000 mg, preferably from about 1 to about 500 mg.

In addition to the active ingredients of the formula (I) and/or their pharmaceutically acceptable salts and to carrier substances, the pharmaceutical preparations can contain one or more additives such as, for example, fillers, disintegrants, binders, lubricants, wetting agents, stabilizers, emulsifiers, preservatives, sweeteners, colorants, flavorings, aromatizers, thickeners, diluents, buffer substances, solvents, solubilizers, agents for achieving a depot effect, salts for altering the osmotic pressure, coating agents or antioxidants. They can also contain two or more compounds of the formula (I) and/or their pharmaceutically acceptable salts. In case a pharmaceutical preparation contains two or more compounds of the formula (I) the selection of the individual compounds can aim at a specific overall pharmacological profile of the pharmaceutical preparation. For example, a highly potent compound with a shorter duration of action may be combined with a long-acting compound of lower potency. The flexibility permitted with respect to the choice of substituents in the compounds of the formula (I) allows a great deal of control over the biological and physico-chemical properties of the compounds and thus allows the selection of such desired compounds. Furthermore, in addition to at least one compound of the formula (I) and/or its pharmaceutically acceptable salts, the pharmaceutical preparations can also contain one or more other therapeutically or prophylactically active ingredients.

When using the compounds of the formula (I) the dose can vary within wide limits and, as is customary and is known to the physician, is to be suited to the individual conditions in each individual case. It depends, for example, on the specific compound employed, on the nature and severity of the disease to be treated, on the mode and the schedule of administration, or on whether an acute or chronic condition is treated or whether prophylaxis is carried out. An appropriate dosage can be established using clinical approaches well known in the medical art. In general, the daily dose for achieving the desired results in an adult weighing about 75 kg is from about 0.01 to about 100 mg/kg, preferably from about 0.1 to about 50 mg/kg, in particular from about 0.1 to about 10 mg/kg, (in each case in mg per kg of body weight). The daily dose can be divided, in particular in the case of the administration of relatively large amounts, into several, for example 2, 3 or 4, part administrations. As usual, depending on individual behavior it may be necessary to deviate upwards or downwards from the daily dose indicated.

Furthermore, the compounds of the formula (I) can be used as synthesis intermediates for the preparation of other compounds, in particular of other pharmaceutical active ingredients, which are obtainable from the compounds of the formula I, for example by introduction of substituents or modification of functional groups.

In general, protective groups that may still be present in the products obtained in the coupling reaction are then removed by standard procedures. For example, tert-butyl protecting groups, in particular a tert-butoxycarbonyl group which is a protection form of an amino group, can be deprotected, i.e. converted into the amino group, by treatment with trifluoroacetic acid. As already explained, after the coupling reaction also functional groups can be generated from suitable precursor groups. In addition, a conversion into a pharmaceutically acceptable salt or a prodrug of a compound of the formulae (I) can then be carried out by known processes.

In general, a reaction mixture containing a final compound of the formula (I) or (I') or an intermediate is worked up and, if desired, the product is then purified by customary processes known to those skilled in the art. For example, a synthesized compound can be purified using well known methods such as crystallization, chromatography or reverse phase-high performance liquid chromatography (RP-HPLC) or other methods of separation based, for example, on the size, charge or hydrophobicity of the compound. Similarly, well known methods such as amino acid sequence analysis, NMR, IR and mass spectrometry (MS) can be used for characterizing a compound of the invention.

(2,2-Dimethoxy-ethyl)-(4-fluoro-benzyl)-amine (1)

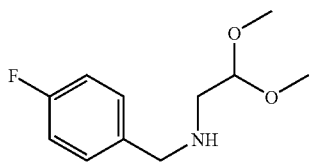

12.4 g of 4-fluorobenzaldehyde were dissolved in 100 mL of toluene and reacted with 10.5 g of 2-aminoacetaldehyde dimethylacetal and 1.90 g of p-toluenesulfonic acid monohydrate for two hours in a Dean Stark apparatus. The solution was allowed to cool to room temperature, extracted with saturated sodium bicarbonate solution, water and brine, dried over magnesium sulfate and evaporated to dryness. The crude product was dissolved in 100 mL of ethanol. 1.89 g of sodium borohydride were added portionwise. Stirring was continued overnight. For workup, acetic acid was added until no gas evolution could be observed. Then the solution was evaporated to dryness, taken up in dichloromethane and washed twice with water. The organic layer was extracted with brine, dried over magnesium sulfate and evaporated to dryness. The obtained crude product (20 g) was used for further reactions without purification. $R_t$=0.86 min (Method B). Detected mass: 182.1 (M-OMe$^-$), 214.2 (M+H$^+$).

N-(2,2-Dimethoxy-ethyl)-N-(4-fluoro-benzyl)-4-methyl-benzene-sulfonamide (2)

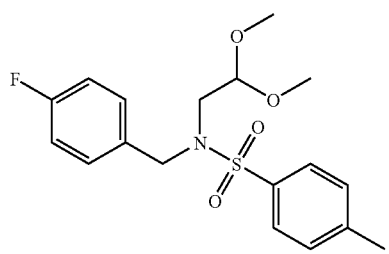 [SMILES: COC(CN(Cc1ccc(F)cc1)S(=O)(=O)c1ccc(C)cc1)OC]

20 g of (2,2-dimethoxy-ethyl)-(4-fluoro-benzyl)-amine (crude 1) were dissolved in 120 ml of dichloromethane. 20 mL of pyridine were added. At 0° C. a solution of 23.8 g p-toluenesulfonic acid chloride in dichloromethane was added dropwise. The reaction was allowed to warm to room temperature and stirring was continued until conversion was completed. For workup, the reaction mixture was washed twice with 2M hydrochloric acid, twice with sodium bicarbonate solution and once with brine. The organic layer was dried over magnesium sulfate, evaporated to dryness and the obtained crude product was purified by silica gel chromatography to yield 22.95 g of compound 2 as an orange oil. $R_t$=1.71 min (Method C). Detected mass: 336.1 (M-OMe$^-$).

6-Fluoro-isoquinoline (3)

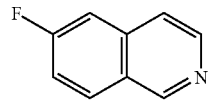 [SMILES: Fc1ccc2cnccc2c1]

41.6 g of AlCl$_3$ were suspended in 400 mL of dichloromethane. At room temperature, a solution of 22.95 g N-(2,2-dimethoxy-ethyl)-N-(4-fluoro-benzyl)-4-methyl-benzene-sulfonamide (2) in 150 ml of dichloromethane was added. Stirring was continued at room temperature overnight, the solution was poured on ice, the layers were separated, the aqueous phase was extracted twice with dichloromethane and the combined organic layers were then washed twice with sodium bicarbonate solution. The organic layer was dried over magnesium sulfate, evaporated to dryness and the obtained crude product (8.75 g) was purified by silica gel chromatography to yield 2.74 g of compound 3. $R_t$=0.30 min (Method C). Detected mass: 148.1 (M+H$^+$).

7-Chloro-6-fluoro-isoquinoline (4)

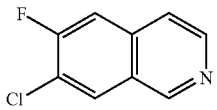

Starting from 3-chloro-4-fluoro-benzaldehyde, the title compound was prepared by the same reaction sequence as used for the synthesis of 6-fluoro-isoquinoline (3). $R_t$=0.77 min (Method A). Detected mass: 182.1 (M+H$^+$).

7-Chloro-6-fluoro-isoquinoline 2-oxide (5)

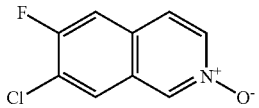 [SMILES: [O-][n+]1ccc2cc(F)c(Cl)cc2c1]

25.0 g of 7-chloro-6-fluoro-isoquinoline (4) were dissolved in 500 ml of dichloromethane. At room temperature, 50.9 g of m-chloro perbenzoic acid (70%) were added and the mixture was stirred at room temperature until complete conversion was achieved. For workup, the precipitate was filtered off and washed with dichloromethane. The filtrate was washed twice with sodium bicarbonate solution. The layers were separated and the aqueous phase was extracted twice with dichloromethane. The organic phases were dried with magnesium sulfate and evaporated. The so obtained solid material (18.4 g) was used without further purification. $R_t$=0.87 min (Method C). Detected mass: 198.1 (M+H$^+$).

1,7-Dichloro-6-fluoro-isoquinoline (6)

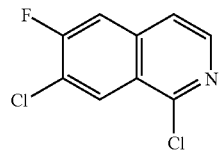 [SMILES: Fc1cc2ccnc(Cl)c2cc1Cl]

2.6 g of 7-chloro-6-fluoro-isoquinoline 2-oxide (5) were heated in 40 ml of POCl$_3$ at reflux for 4 h. After the mixture has cooled down to room temperature, it was poured on ice. The aqueous solution was extracted three times with dichloromethane. The combined organic layers were dried with magnesium sulfate and evaporated to yield 2.91 g of the title compound 6, which was used without further purification. $R_t$=2.34 min (Method A). Detected mass: 216.0 (M+H$^+$).

7-Chloro-6-fluoro-2H-isoquinolin-1-one (7)

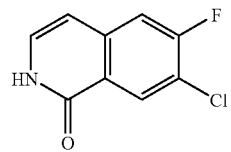 [SMILES: O=c1[nH]ccc2cc(F)c(Cl)cc12]

41.13 g of 1,7-dichloro-6-fluoro-isoquinoline (6) were dissolved in 670 ml of acetic acid. After addition of 148.8 g of ammonium acetate, the solution was stirred at 100° C. After 3 h, the solvent was removed under reduced pressure and the residue was poured onto water. The aqueous phase was extracted three times with dichloromethane, the combined organic layer was washed with saturated sodium bicarbonate solution and brine, dried over sodium sulfate and evaporated to dryness. The crude product was crystallized from ethyl acetate:heptane to yield 14.85 g of the desired product. Another 4.5 g could be obtained upon evaporation and silica gel chromatography of the mother liquor.

The precipitate was filtered and dried to yield 9.91 g of the title compound. $R_t$=1.33 min (Method B). Detected mass: 198.0 (M+H$^+$).

6-Fluoro-isoquinolinone (8)

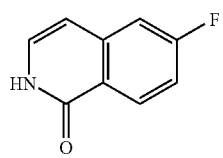

4.8 mL of thionyl chloride was added portionwise to a solution of 10 g of 3-fluoro cinnamic acid in 44 ml of chloroform and 1 ml of DMF. The reaction was heated to reflux for 2.5 h. Then the solvents were distilled to yield 11.4 g of the raw acid chloride, which was used without further purification.

The acid chloride was dissolved in 45 mL of acetone. At 0° C. 8.03 g of NaN$_3$ were added portionwise. Then 41 mL of water were added while the temperature was kept below 5° C. The reaction was stirred for another 1.5 h. Then 55 ml of chloroform were added. The mixture was extracted with 80 mL of water followed by 40 mL of brine. After drying over Na$_2$SO$_4$ and filtration, 14 mL of diphenyl ether were added and most of the chloroform was removed in vacuo (without heating). A total removal of the chloroform should be avoided.

The solution containing the azide, diphenyl ether and the remaining chloroform was added dropwise at 260° C. within 15 minutes to a solution of 10 mL of tributyl amine in 97 ml of diphenyl ether. A vigorous reaction could be observed during the addition. The reaction was stirred for another 20 minutes at 260° C. After cooling to room temperature 270 mL of n-heptane were added. The precipitated product was filtered off and washed with ether to yield 5.65 g of the title compound. MS (DCI) Detected mass: 164.0 (M+H$^+$).

6-Fluoro-2-(4-methoxy-benzyl)-2H-isoquinolin-1-one (9)

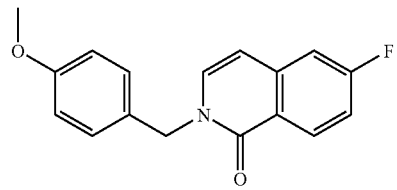 [SMILES: COc1ccc(Cn2ccc3cc(F)ccc3c2=O)cc1]

169 µL of p-methoxybenzylchloride were added to a suspension of 200 mg of 6-fluoro-isoquinolinone (8) and 368 mg (1.36 mmol, 1.2 eq) of Cs$_2$CO$_3$ in 3 mL of DMF. The mixture was stirred for 2 h and then poured on ice. The precipitate was filtered, washed with water and dried to yield 300 mg of the title compound. $R_t$=1.76 min (Method B). Detected mass: 284.14 (M+H$^+$).

7-Chloro-6-fluoro-2-(4-methoxy-benzyl)-2H-isoquinolin-1-one (10)

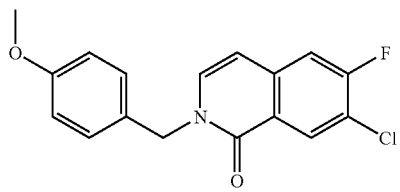 [SMILES: COc1ccc(Cn2ccc3cc(F)c(Cl)cc3c2=O)cc1]

Starting from 7-chloro-6-fluoro-2H-isoquinolin-1-one (7) the title compound was prepared following the protocol described for 6-fluoro-2-(4-methoxy-benzyl)-2H-isoquinolin-1-one (9). $R_t$=1.66 min (Method C). Detected mass: 318.3 (M+H$^+$).

1-Benzyloxy-7-chloro-6-fluoro-isoquinoline (11)

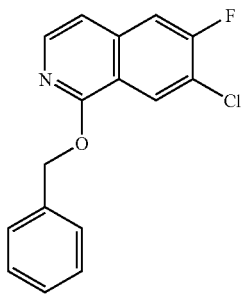 [SMILES: Fc1cc2ccnc(OCc3ccccc3)c2cc1Cl]

14.7 g of 7-chloro-6-fluoro-2H-isoquinolin-1-one (7) were dissolved in 150 ml of toluene. After addition of 30.9 g of silver carbonate and 15.3 g of benzyl bromide, the mixture was stirred at 80° C. for 3 h. After cooling down to room temperature, the reaction mixture was filtered and the filtrate was evaporated. The residue was dissolved in dichloromethane and washed with water, dried with magnesium sulfate and evaporated. Final purification by preparative HPLC gave 11.6 g of the title compound. $R_t$=2.51 min (Method B). Detected mass: 288.1/290.1 (M+H$^+$).

6-Fluoro-7-methyl-2H-isoquinolin-1-one (12)

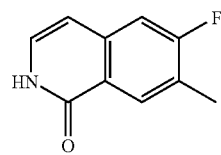

To a solution of 10.0 g of 3-fluoro-4-methyl-cinnamic acid in 80 ml acetone were subsequently added at 0° C. 6.74 g triethylamine in 10 ml acetone followed by 7.83 g ethyl chloroformate. After stirring for 2 h at 0 to 5° C. a solution of 4.0 g sodium azide in 9.5 ml water was added. After stirring for 1 additional h the reaction mixture was poured onto 200 ml ice water and extracted twice with chloroform. The organic phase was dried over magnesium sulfate, 40 ml diphenylether were added and the chloroform was cautiously removed in vacuo. The residue was then added dropwise into 50 ml of diphenylether which had been preheated to 245° C. After complete addition it was stirred for 1 further h at 230-250° C. After cooling down to 150° C. the reaction mixture was poured into 270 ml heptane and after further cooling in an ice bath the precipitated product was filtered by suction and 4.1 g 6-fluoro-7-methyl-2H-isoquinolin-1-one (12) were obtained. $R_t$=1.25 min (Method B). Detected mass: 178.1 (M+H$^+$).

6-Fluoro-2-(4-methoxy-benzyl)-7-methyl-2H-isoquinolin-1-one (13)

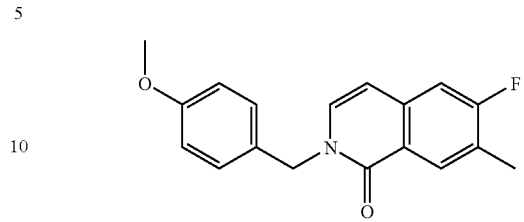

To a solution of 9.17 g of 6-fluoro-7-methyl-2H-isoquinolin-1-one (12) in 80 ml DMF were added 20.2 g caesium carbonate and then 8.92 g 4-methoxybenzyl-chloride. After stirring at room temperature for 90 minutes the reaction mixture was poured into 600 ml water, stirred for 1 h, and then the precipitated product was filtrated by suction. From the mother liquor additional producted was isolated by chromatography with heptane/ethyl acetate (80:20). The combined products were recrystallized from ethyl acetate and 8.39 g 6-fluoro-2-(4-methoxy-benzyl)-7-methyl-2H-isoquinolin-1-one (13) were received. $R_t$=1.83 min (Method B). Detected mass: 298.1 (M+H$^+$).

1-Benzyloxy-6-fluoro-7-methyl isoquinoline (14) and 4-Benzyl-1-benzyloxy-6-fluoro-7-methyl-isoquinoline (15)

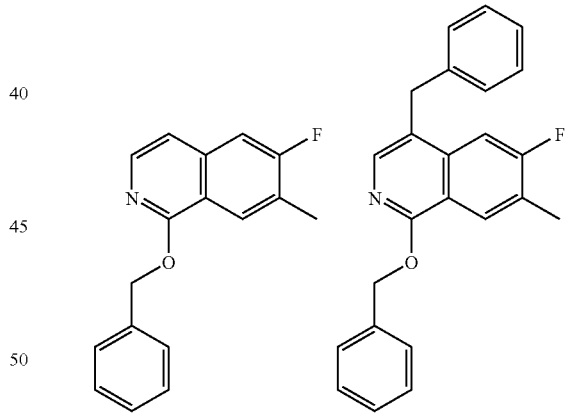

13.23 g of 6-fluoro-7-methyl-2H-isoquinolin-1-one (12) were dissolved in 175 ml of THF. After addition of 41.17 g of silver carbonate, 15.3 g of benzyl bromide were added dropwise. The mixture was stirred overnight. The mixture was heated to 70° C. and another 3 mL of benzyl bromide were added. Heating was continued until no further conversion was observed. The mixture was taken up in a big amount of ethyl acetate, filtered over celite, evaporated and the residue was taken up in little ethyl acetate. The formed precipitate was filtered off to give 3.0 g of 14. The mother liquor was concentrated and chromatographed on silica gel to yield another 8.6 g of 14. 15, which is formed as a by-product in the reaction, could be isolated by another silica gel chromatography. 14: R$_t$=4.00 min (Method H). Detected mass: 268.1 (M+H$^+$); 15: R$_t$=4.00 min (Method H). Detected mass: 358.1 (M+H$^+$)

4-Allyl-4-amino-cyclohexanol (16)

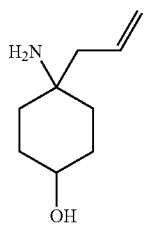

a) 1-Allyl-4-(tert-butyl-dimethyl-silanyloxy)-cyclohexylamine

To a solution of 1.0 g (4.38 mmol) of 4-(tert-butyldimethylsilyloxy)cyclohexanone in 6.2 mL (43.8 mmol) of 7N ammonia in methanol, previously stirred for 15 min at room temperature, were added dropwise 3.5 mL (7.0 mmol) of a 2M solution of 2-allyl-4,4,5,5-tetramethyl-1,3,2-dioxa-borolane in methanol. The reaction mixture was stirred for 16 h at room temperature. The volatiles were removed in vacuo and the residue could be purified by silica gel chromatography using dichloromethane/methanol/NH$_3$ aq. as eluent. R$_t$=1.19 min (Method C). Detected mass: 270.3 (M+H$^+$).

b) 4-Allyl-4-amino-cyclohexanol (16)

The crude 1-allyl-4-(tert-butyl-dimethyl-silanyloxy)-cyclohexylamine (16, step a) was dissolved in 100 mL of diethyl ether. Then, 100 mL of 1N aqueous HCl were added dropwise and the resultant biphasic mixture was stirred for 30 min. The layers were separated, the aqueous layer was washed with diethyl ether and the pH adjusted to pH8 by the addition of solid sodium hydroxide. The suspension was then extracted with a 3:1 mixture of dichloromethane and 2-propanol and the combined organic extracts were concentrated in vacuo to afford 0.54 g of the title compound as mixture of diastereomers (1.5:1). R$_t$=0.15 min, 0.27 min (Method C). Detected mass: 156.2 (M+H$^+$).

6-(4-Allyl-4-amino-cyclohexyl oxy)-7-chloro-2-(4-methoxy-benzyl)-2H-isoquinolin-1-one (17)

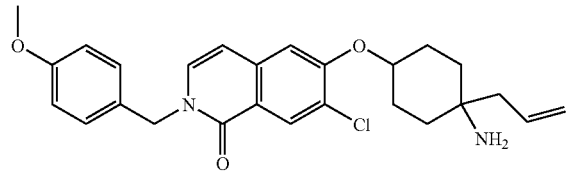 [SMILES: C=CCC1(N)CCC(Oc2cc3ccn(Cc4ccc(OC)cc4)c(=O)c3cc2Cl)CC1]

155 mg (3.86 mmol) of sodium hydride (60%) were suspended in 3 mL of dimethyl acetamide and 220 mg (1.42 mmol) of 4-allyl-4-amino-cyclohexanol (16), dissolved in 1 mL of dimethyl acetamide, were added dropwise. After 1 h, 409 mg (1.29 mmol) of 2-(4-methoxy-benzyl)-6-fluoro-7-chloro-2H-isoquinolin-1-one (10), dissolved in another 2 mL of dimethyl acetamide, were added. The reaction mixture was stirred at room temperature until the reaction was complete. The mixture was quenched by dropwise addition of water, extracted with a mixture of dichloromethane and 2-propanol (3:1) and the combined organic layers were evaporated. Water was added and the crude product was subjected to lyophilization to remove remainders of dimethyl acetamide. The obtained crude product was purified by silica gel chromatography to yield 148 mg of the title compound (17) as diastereomeric mixture. R$_t$=1.35 min, 1.40 min (Method B). Detected mass: 453.3 (M+H$^+$).

6-(4-Allyl-4-amino-cyclohexyloxy)-2-(4-methoxy-benzyl)-2H-isoquinolin-1-one (18)

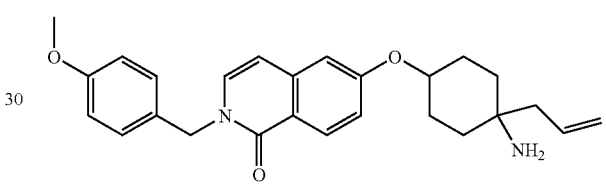

422 mg of 6-(4-allyl-4-amino-cyclohexyloxy)-2-(4-methoxy-benzyl)-2H-isoquinolin-1-one (18) were synthesized as diastereomeric mixture starting from 641 mg (2.26 mmol) of 2-(4-methoxy-benzyl)-6-fluoro-2H-isoquinolin-1-one (9) and 370 mg (2.38 mmol) of 4-allyl-4-amino-cyclohexanol (16), following the protocol described for 6-(4-allyl-4-amino-cyclohexyloxy)-7-chloro-2-(4-methoxy-benzyl)-2H-isoquinolin-1-one (17). R$_t$=1.07 min, 1.10 min (Method C). Detected mass: 419.2 (M+H$^+$).

6-(cis-4-Allyl-4-amino-cyclohexyloxy)-7-methyl-2-(4-methoxy-benzyl)-2H-isoquinolin-1-one (19)

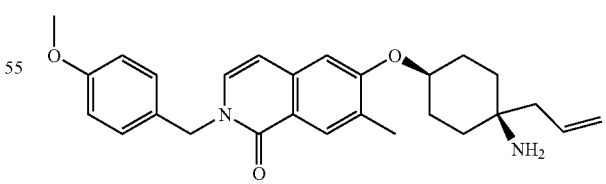

957 mg of 6-(cis-4-allyl-4-amino-cyclohexyloxy)-7-methyl-2-(4-methoxy-benzyl)-2H-isoquinolin-1-one (19) were synthesized starting from 2.49 g (8.37 mmol) of 6-fluoro-2-(4-methoxy-benzyl)-7-methyl-2H-isoquinolin-1-one (13) and 1.30 g (8.37 mmol) of 4-allyl-4-amino-cyclohexanol (16), following the protocol described for 6-(4-allyl-4- amino-cyclohexyloxy)-7-chloro-2-(4-methoxy-benzyl)-2H-isoquinolin-1-one (17). $R_t$=1.14 min (Method C). Detected mass: 433.3 (M+H$^+$).

6-(4-Allyl-4-amino-cyclohexyloxy)-7-chloro-2H-isoquinolin-1-one (20)

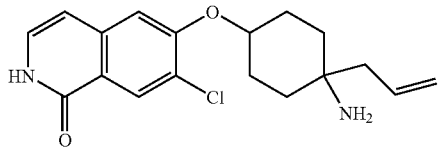 [SMILES: C=CCC1(N)CCC(Oc2cc3cc[nH]c(=O)c3cc2Cl)CC1]

138 mg (0.30 mmol) of 6-(4-allyl-4-amino-cyclohexyloxy)-7-chloro-2-(4-methoxy-benzyl)-2H-isoquinolin-1-one (17) were dissolved in 2 mL of TFA and heated in a microwave oven at 150° C. for 2 h. Methanol was added and the reaction mixture was evaporated. The crude product was separated via preparative HPLC to give the desired product as the trifluoroacetate. To obtain the hydrochloride salt, the resultant trifluoroacetates were taken up in 1N HCl and lyophilized two times. The respective residue was redissolved in water and lyophilized again to yield 42 mg of a diastereomeric mixture of 6-(4-allyl-4-amino-cyclohexyloxy)-7-chloro-2H-isoquinolin-1-one (20) as hydrochloride. $R_t$=1.02 min, 1.08 min (Method B). Detected mass: 333.2 (M+H$^+$).

6-(4-Allyl-4-amino-cyclohexyloxy)-2H-isoquinolin-1-one (21)

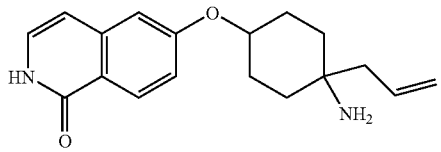 [SMILES: C=CCC1(N)CCC(Oc2ccc3c(=O)[nH]ccc3c2)CC1]

30 mg of 6-(4-allyl-4-amino-cyclohexyloxy)-2H-isoquinolin-1-one (21) as diastereomeric mixture, obtained as the hydrochloride, were synthesized from 114 mg (0.27 mmol) of 6-(4-allyl-4-amino-cyclohexyloxy)-2-(4-methoxy-benzyl)-2H-isoquinolin-1-one (18) following the procedure of 6-(4-allyl-4-amino-cyclohexyloxy)-7-chloro-2H-isoquinolin-1-one (20). $R_t$=0.93 min, 0.98 min (Method B). Detected mass: 299.2 (M+H$^+$).

6-(4-Allyl-4-amino-cyclohexyloxy)-4,7-dimethyl-2H-isoquinolin-1-one (22)

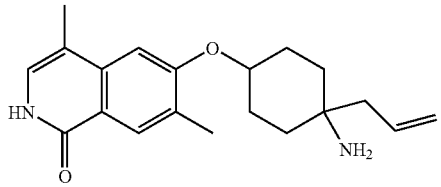 [SMILES: C=CCC1(N)CCC(Oc2cc3c(C)c[nH]c(=O)c3cc2C)CC1]

6-(4-Allyl-4-amino-cyclohexyloxy)-4,7-dimethyl-2H-isoquinolin-1-one (22) as diastereomeric mixture, obtained as the hydrochloride, was synthesized in a similar fashion as described for the synthesis of (20), using 2-(4-methoxy-benzyl)-4,7-dimethyl-2H-isoquinolin-1-one (which could be prepared from 3-(3-fluoro-4-methyl-phenyl)-but-2-enoic acid following the procedure described for the synthesis of 12 and 13). $R_t$=2.11 min, 2.18 min (Method H). Detected mass: 327.2 (M+H$^+$).

6-(cis-4-Allyl-4-amino-cyclohexyloxy)-2H-isoquinolin-1-one (23)

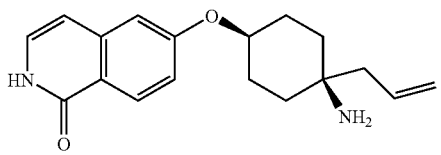 [SMILES: C=CC[C@]1(N)CC[C@@H](Oc2ccc3c(=O)[nH]ccc3c2)CC1]

The pure compound 23 was obtained by separation of a diastereomeric mixture of compound 21 via preparative HPLC and lyophilization of the residue from 2N HCl and water, respectively to give the hydrochloride. $R_t$=1.01 min (Method B). Detected mass: 299.2 (M+H$^+$).

6-(cis-4-Allyl-4-amino-cyclohexyloxy)-7-methyl-2H-isoquinolin-1-one (24)

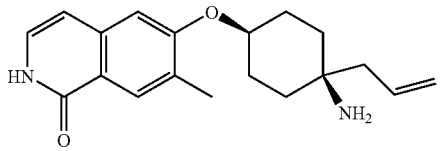 [SMILES: C=CC[C@]1(N)CC[C@@H](Oc2cc3cc[nH]c(=O)c3cc2C)CC1]

11 mg of 6-(cis-4-allyl-4-amino-cyclohexyloxy)-7-methyl-2H-isoquinolin-1-one (24, hydrochloride salt) were synthesized from 100 mg (0.23 mmol) of 6-(cis-4-allyl-4-amino-cyclohexyloxy)-7-methyl-2-(4-methoxy-benzyl)-2H-isoquinolin-1-one (19) following the procedure of 6-(4-allyl-4-amino-cyclohexyloxy)-7-chloro-2H-isoquinolin-1-one (20). $R_t$=1.01 min (Method F). Detected mass: 313.2 (M+H$^+$).

2-Methyl-propane-2-sulfinic acid [4-(tert-butyl-dimethyl-silanyloxy)-cyclohexylidene]-amide (25)

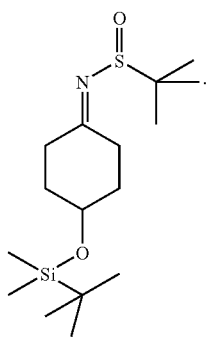 [SMILES: CC(C)(C)S(=O)N=C1CCC(O[Si](C)(C)C(C)(C)C)CC1]

To a solution of 5.00 g (21.9 mmol) of 4-(tert-butyl-dimethyl-silanyloxy)-cyclohexanone in 100 mL THF was added 9.18 mL (43.8 mmol) of Ti(OEt)$_4$ and 2.78 g (23.0 mmol) of 2-methyl-2-propanesulfinamide. The resulting mixture was stirred under reflux for 12 h, before being poured into an equal volume of saturated aqueous NaHCO$_3$ with rapid stirring and filtered through celite. The filter cake was washed with ethyl acetate, the aqueous layer was separated and extracted twice with ethyl acetate. The combined organic layers were dried over MgSO$_4$, filtered, and concentrated under vacuum. The crude product was purified by silica gel chromatography to yield 5.12 g of the title compound (25) as diastereomeric mixture. $R_t$=1.87 min, 1.92 min (Method C). Detected mass: 332.3 (M+H$^+$).

2-Methyl-propane-2-sulfinic acid [4-(tert-butyl-dimethyl-silanyloxy)-1-cyclopropyl-cyclohexyl]-amide (26)

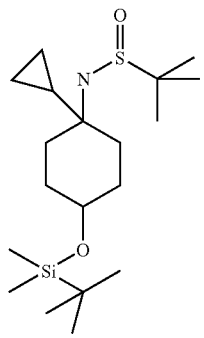 [SMILES: CC(C)(C)S(=O)NC1(C2CC2)CCC(O[Si](C)(C)C(C)(C)C)CC1]

A solution of 3.00 g (9.05 mmol) of 2-methyl-propane-2-sulfinic acid [4-(tert-butyl-dimethyl-silanyloxy)-cyclohexylidene]-amide (25) in 15 mL of diethyl ether was added dropwise to 54.3 mL (27.1 mmol) of a 0.5 M solution of cyclopropylmagnesium bromide in diethyl ether precooled to −78° C. The reaction solution was stirred at −78° C. for 1 h and was allowed to warm to room temperature overnight. The reaction was quenched by dropwise addition of saturated aqueous Na$_2$SO$_4$, dried over MgSO$_4$, filtered, and concentrated under vacuum. The crude product was purified by silica gel chromatography to yield 800 mg of the title compound (26) as diastereomeric mixture. $R_t$=2.22 min, 2.25 min (Method C). Detected mass: 374.3 (M+H$^+$).

2-Methyl-propane-2-sulfinic acid [4-(tert-butyl-dimethyl-silanyloxy)-bicyclohexyl-1-yl]-amide (27)

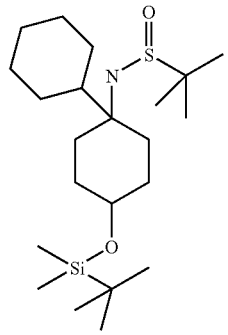 [SMILES: CC(C)(C)S(=O)NC1(C2CCCCC2)CCC(O[Si](C)(C)C(C)(C)C)CC1]

1.13 g of 2-methyl-propane-2-sulfinic acid [4-(tert-butyl-dimethyl-silanyloxy)-bicyclohexyl-1-yl]-amide (27) as diastereomeric mixture were synthesized from 2.00 g (6.03 mmol) of 2-methyl-propane-2-sulfinic acid [4-(tert-butyl-dimethyl-silanyloxy)-cyclohexylidene]-amide (25) and 15 mL (30.2 mmol) of a 2M solution of cyclohexylmagnesium chloride in THF following the procedure for 2-methyl-propane-2-sulfinic acid [4-(tert-butyl-dimethyl-silanyloxy)-1-cyclopropyl-cyclohexyl]-amide (26). $R_t$=1.90 min, 2.00 min (Method I). Detected mass: 416.3 (M+H$^+$).

4-Amino-4-cyclopropyl-cyclohexanol (28)

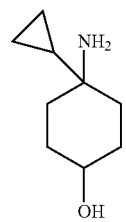 [SMILES: NC1(C2CC2)CCC(O)CC1]

To a solution of 1.00 g (2.68 mmol) of 2-methyl-propane-2-sulfinic acid [4-(tert-butyl-dimethyl-silanyloxy)-1-cyclopropyl-cyclohexyl]-amide (26) in 6 mL of 2-propanol were added 2 mL of 2N hydrochloric acid and the mixture was stirred at room temperature until complete conversion was achieved. The reaction mixture was washed with diethyl ether, the aqueous phase was concentrated in vacuo and lyophilized to yield a diastereomeric mixture of 4-amino-4-cyclopropyl-cyclohexanol (28) as hydrochloride which was used crude in the next step. $R_t$=0.21 min (Method C). Detected mass: 156.2 (M+H$^+$).

1-Amino-bicyclohexyl-4-ol (29)

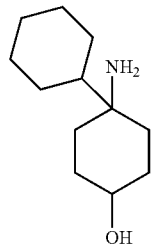 [SMILES: NC1(C2CCCCC2)CCC(O)CC1]

425 mg of diastereomeric 1-amino-bicyclohexyl-4-ol (29) was synthesized as hydrochloride from 1.13 g (2.72 mmol) of 2-methyl-propane-2-sulfinic acid [4-(tert-butyl-dimethyl-silanyloxy)-bicyclohexyl-1-yl]-amide (27) following the procedure for 4-amino-4-cyclopropyl-cyclohexanol (28). $R_t$=0.61 min, 0.76 min (Method C). Detected mass: 198.3 (M+H$^+$), 163.0 (M-NH$_3$+H$^+$).

5-Allyl-5-amino-cyclooctanol (30)

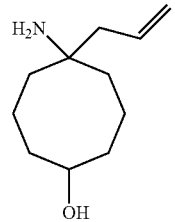

0.89 g of 5-Allyl-5-amino-cyclooctanol (30) were synthesized as a diastereomeric mixture starting from 1.50 g (5.85 mmol) of 5-(tert-butyldimethylsilyloxy)cyclooctanone, 8.4 mL (58.5 mmol) of 7N ammonia in methanol, and 1.7 mL (9.36 mmol) of 2-allyl-4,4,5,5-tetramethyl-1,3,2-dioxaborolane, following the protocol described for 4-allyl-4-aminocyclohexanol (16). $R_t$=0.44 min, 0.49 min (Method C). Detected mass: 184.3 (M+H$^+$).

[1-Allyl-4-(tert-butyl-dimethyl-silanyloxy)-cyclohexyl]-carbamic acid tert-butyl ester (31)

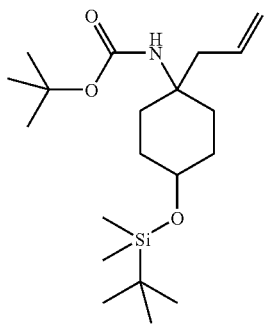 [SMILES: C=CCC1(NC(=O)OC(C)(C)C)CCC(O[Si](C)(C)C(C)(C)C)CC1]

To a solution of 3.00 g (11.1 mmol) of 1-allyl-4-(tert-butyl-dimethyl-silanyloxy)-cyclohexylamine (16, step a) in 150 mL of dichloromethane at 0° C. were added 2.92 g (13.4 mmol) of di-tert-butyl dicarbonate and 1.5 mL (10.7 mmol) of triethylamine. The reaction mixture was stirred for 14 h at room temperature, before being washed with water twice, dried over magnesium sulfate and concentrated. 3.24 g of the title compound could be isolated in a purity sufficient for further conversion. $R_t$=1.85 min (Method I). Detected mass: 270.2 (M-Boc+H$^+$).

[4-(tert-Butyl-dimethyl-silanyloxy)-1-(3-hydroxy-propyl)-cyclohexyl]-carbamic acid tert-butyl ester (32)

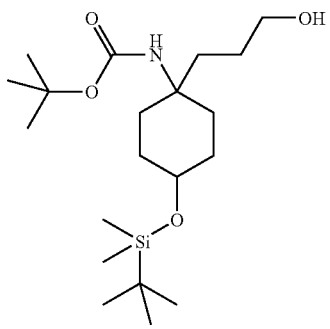 [SMILES: CC(C)(C)OC(=O)NC1(CCCO)CCC(O[Si](C)(C)C(C)(C)C)CC1]

16.2 mL (8.12 mmol) of a 0.5M solution of 9-BBN in THF were added to a solution of 1.00 g (2.71 mmol) of [1-allyl-4-(tert-butyl-dimethyl-silanyloxy)-cyclohexyl]-carbamic acid tert-butyl ester (31) in 5 mL THF at 0° C. The reaction mixture was allowed to warm to room temperature over night, before being cooled to 0° C. Then, 20 mL of 3M aqueous sodium hydroxide and 20 mL of 30% aqueous hydrogen peroxide were added slowly, and the mixture was stirred for 12 h. The mixture was extracted twice with ethyl acetate, washed with water and saturated sodium chloride solution, dried over magnesium sulfate and concentrated in vacuo. 0.85 g of the title compound 32 could be isolated as mixture of diastereoisomers in a purity sufficient for further conversion. $R_t$=2.03 min, 2.10 min (Method C). Detected mass: 388.3 (M+H$^+$).

4-Amino-4-(3-methoxy-propyl)-cyclohexanol (33)

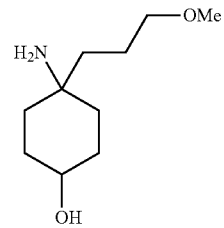 [SMILES: COCCCC1(N)CCC(O)CC1]

a) [4-(tert-Butyl-dimethyl-silanyloxy)-1-(3-methoxy-propyl)-cyclohexyl]-carbamic acid tert-butyl ester A solution of 250 mg (0.65 mmol) of [4-(tert-butyl-dimethyl-silanyloxy)-1-(3-hydroxy-propyl)-cyclohexyl]-carbamic acid tert-butyl ester (32) in 3 mL of THF was dropped into a suspension of 28.3 mg (0.71 mmol) of sodium hydride (60%) in 8 mL THF at 0° C. 120 µL (1.94 mmol) of iodomethane were added, and after stirring for 1 h at room temperature another 120 µL (1.94 mmol) of iodomethane were added. The reaction mixture was stirred for 14 h at room temperature, then 5 mL of methanol were added and the volatiles were removed in vacuo. $R_t$=2.32 min, 2.37 min (Method C). Detected mass: 402.3 (M+H$^+$), 302.3 (M-Boc+H$^+$).

b) 4-Amino-4-(3-methoxy-propyl)-cyclohexanol (33)

200 mg of the crude [4-(tert-butyl-dimethyl-silanyloxy)-1-(3-methoxy-propyl)-cyclohexyl]-carbamic acid tert-butyl ester (33, step a) were dissolved in 10 mL of dichloromethane and treated with 370 µL of trifluoroacetic acid. After stirring at room temperature until complete conversion was achieved, 2M aqueous hydrochloric acid was added, the mixture stirred for further 60 min and the aqueous phase evaporated. The crude aminoalcohol was lyophilized from water and used crude as hydrochloride in the next reaction. $R_t$=0.18 min, 0.37 min (Method C). Detected mass: 188.3 (M+H$^+$).

cis-4-(1-Benzyloxy-7-chloro-isoquinolin-6-yloxy)-1-cyclopropyl-cyclohexylamine (34) and trans-4-(1-benzyloxy-7-chloro-isoquinolin-6-yloxy)-1-cyclopropyl-cyclohexylamine (35)

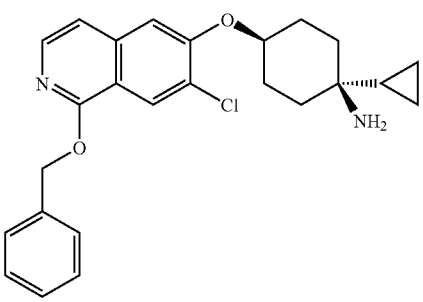

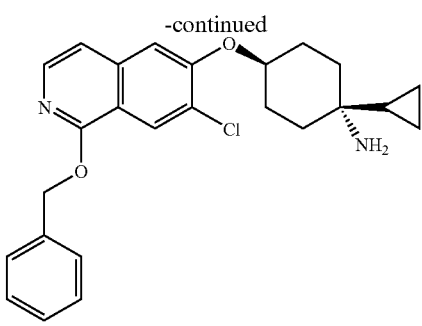

To a suspension of 312 mg (7.80 mmol) of sodium hydride (60%) in 12 mL of dimethyl acetamide was added a solution of 404 mg (2.60 mmol) of 4-amino-4-cyclopropyl-cyclohexanol (28) in 6 ml of dimethyl acetamide. After stirring for 60 min at room temperature a solution of 823 mg (2.86 mmol) of 1-benzyloxy-7-chloro-6-fluoro-isoquinoline (11) in 12 ml of dimethyl acetamide was added and stirring was continued first at room temperature, then at 50° C. until the reaction went to completion. The reaction was quenched by addition of 30 mL of water and the reaction mixture was extracted three times with a mixture of dichloromethane and 2-propanol (3:1). The combined organic layers were evaporated, water was added and the crude product was subjected to lyophilization to remove remainders of dimethyl acetamide. The obtained crude product was purified by silica gel chromatography to yield 63 mg of the cis-isomer 34, 78 mg of the trans-isomer 35 and 148 mg of the title compound as diastereomeric mixture. $R_t$=1.30 min (34), 1.35 min (35) (Method C). Detected mass: 423.2 (M+H$^+$).

The following products were obtained by the same procedure described for the synthesis of 34/35 using 1-benzyloxy-7-chloro-6-fluoro-isoquinoline (11) or 1-benzyloxy-7-methyl-6-fluoro-isoquinoline (13) and the corresponding aminoalcohols.

TABLE 1

| Example | Iso-quinoline | Amino-alcohol | Product | Chemical Name | [M + H$^+$] | $R_t$ [min] | Method |
|---|---|---|---|---|---|---|---|
| 36 | 13 | 28 | | 4-(1-benzyloxy-7-methyl-isoquinolin-6-yloxy)-1-cyclopropyl-cyclohexylamine | 403.3 | 1.27 | C |
| 37 | 11 | 29 | | 4-(1-benzyloxy-7-chloro-isoquinolin-6-yloxy)-bicyclohexyl-1-ylamine | 465.3 | 1.06 | G |
| 38 | 11 | 16 | | 1-allyl-4-(1-benzyloxy-7-chloro-isoquinolin-6-yloxy)-cyclohexylamine | 423.2 | 1.37, 1.43 | C |
| 39 | 11 | 30 | | 1-allyl-5-(1-benzyloxy-7-chloro-isoquinolin-6-yloxy)-cyclooctylamine | 451.2 | 1.44, 1.50 | C |
| 40 | 11 | 33 | | 4-(1-benzyloxy-7-chloro-isoquinolin-6-yloxy)-1-(3-methoxy-propyl)-cyclohexylamine | 455.3 | 1.31, 1.39 | C |

6-(cis-4-Amino-4-cyclopropyl-cyclohexyloxy)-7-chloro-2H-isoquinolin-1-one (41)

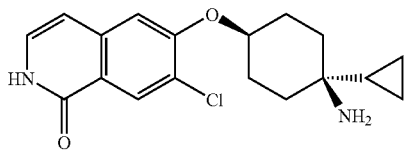 [SMILES: N[C@]1(C2CC2)CC[C@H](Oc2cc3cc[nH]c(=O)c3cc2Cl)CC1]

A solution of 63 mg (0.15 mmol) of cis-4-(1-benzyloxy-7-chloro-isoquinolin-6-yloxy)-1-cyclopropyl-cyclohexylamine (34) in 9 mL of 2-propanol was treated with 3 mL of 2N aqueous hydrochloric acid and stirred at room temperature until complete conversion was observed. The reaction mixture was evaporated, twice lyophilized from water and recrystallized from 2-propanol. 30 mg of the title compound could be isolated as its hydrochloride. $R_t$=0.99 min (Method B). Detected mass: 333.2 (M+H$^+$).

The following products were synthesized as hydrochlorides using the standard deprotection procedure described for the synthesis of 6-(cis-4-amino-4-cyclopropyl-cyclohexyloxy)-7-chloro-2H-isoquinolin-1-one (41). If the diastereoisomers could not be separated previously, the deprotected products were purified by preparative HPLC and lyophilized from 1N HCl and water.

TABLE 2

| Example | Starting compound | Product | Chemical Name | [M + H$^+$] | $R_t$ [min] | Method |
|---|---|---|---|---|---|---|
| 42 | 35 | | 6-(trans-4-amino-4-cyclopropyl-cyclohexyloxy)-7-chloro-2H-isoquinolin-1-one | 333.1 | 1.13 | B |
| 43 | 36 | | 6-(trans-4-amino-4-cyclopropyl-cyclohexyloxy)-7-methyl-2H-isoquinolin-1-one | 313.2 | 2.24 | F |
| 44 | 37 | | 6-(cis-1-amino-bicyclohexyl-4-yloxy)-7-chloro-2H-isoquinolin-1-one | 375.3 | 2.35 | H |
| 45 | 37 | | 6-(trans-1-amino-bicyclohexyl-4-yloxy)-7-chloro-2H-isoquinolin-1-one | 358.2 (M−NH$_3$+H$^+$) | 2.60 | F |
| 46 | 39 | | 6-(5-allyl-5-amino-cyclooctyloxy)-7-chloro-2H-isoquinolin-1-one | 361.2 | 1.70, 1.77 | E |
| 47 | 40 | | 6-[cis-4-amino-4-(3-methoxy-propyl)-cyclohexyloxy]-7-chloro-2H-isoquinolin-1-one | 365.2 | 2.28 | F |
| 48 | 40 | | 6-[trans-4-amino-4-(3-methoxy-propyl)-cyclohexyloxy]-7-chloro-2H-isoquinolin-1-one | 365.3 | 2.46 | J |

6-(trans-4-Benzylamino-4-cyclopropyl-cyclohexyloxy)-7-chloro-2H-isoquinolin-1-one (49)

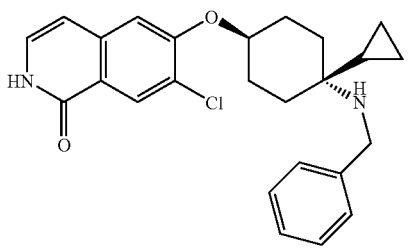 [SMILES: O=c1[nH]ccc2cc(O[C@H]3CC[C@@](NCc4ccccc4)(C4CC4)CC3)c(Cl)cc12]

55.0 mg (0.17 mmol) of 6-(trans-4-amino-4-cyclopropyl-cyclohexyloxy)-7-chloro-2H-isoquinolin-1-one (42) were dissolved in 1.0 mL of methanol and molecular sieves 4 Å were added. Then, 45.8 μL (0.34 mmol) of triethyl amine, 94.5 μL (1.65 mmol) of acetic acid and 52.6 mg (0.49 mmol) of benzaldehyde were added. After stirring for 60 min, a solution of 31.2 mg (0.49 mmol) of sodium cyano borohydride in 0.5 mL of methanol was added dropwise and the mixture was stirred first at room temperature, the at 70° C. until complete conversion was achieved. The solution was filtered and the solvent was removed under reduced pressure. The residue was dissolved in dichloromethane and washed with saturated aqueous sodium bicarbonate solution. The aqueous phase was the reextracted three times with dichloromethane, the organic phases combined, dried over magnesium sulfate and evaporated. The residue was triturated with 2-propanol, filtered, and the precipitate was lyophilized from water. 24 mg of the title compound could be isolated as its hydrochloride. $R_f$=2.50 min (Method H). Detected mass: 423.3 (M+H$^+$).

The following two products were obtained as hydrochlorides by the general procedure for the reductive amination reaction described for the synthesis of 6-(trans-4-benzylamino-4-cyclopropyl-cyclohexyloxy)-7-chloro-2H-isoquinolin-1-one (49) using 6-(4-amino-4-cyclopropyl-cyclohexyloxy)-7-chloro-2H-isoquinolin-1-one as diastereomeric mixture (34 and 35) or as pure trans-isomer (35) and the corresponding aldehydes or ketones. The monoalkylated products were purified by preparative HPLC and lyophilized from 1N HCl and water.

[1-Allyl-4-(1-benzyloxy-7-chloro-isoquinolin-6-yloxy)-cyclohexyl]-carbamic acid tert-butyl ester (52)

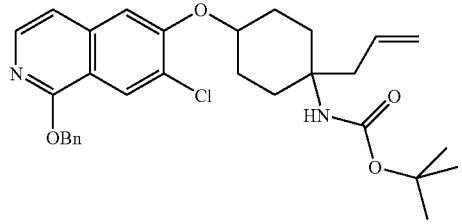 [SMILES: C=CCC1(NC(=O)OC(C)(C)C)CCC(Oc2cc3ccnc(OCc4ccccc4)c3cc2Cl)CC1]

To a solution of 1.21 g (2.87 mmol) of 1-allyl-4-(1-benzyloxy-7-chloro-isoquinolin-6-yloxy)-cyclohexylamine (38) in 50 mL of dichloromethane at 0° C. were added 938 mg (4.30 mmol) of di-tert-butyl dicarbonate and 0.60 mL (4.30 mmol) of triethylamine. The reaction mixture was stirred for 14 h at room temperature, before being concentrated in vacuo. The residue was dissolved in diethyl ether, filtered over celite and evaporated. 1.14 g of the title compound could be isolated as mixture of stereoisomers in a purity sufficient for further conversion. $R_f$=1.83 min, 1.88 min (Method I). Detected mass: 523.2 (M+H$^+$).

[4-(1-Benzyloxy-7-chloro-isoquinolin-6-yloxy)-1-(3-hydroxy-propyl)-cyclohexyl]-carbamic acid tert-butyl ester (53)

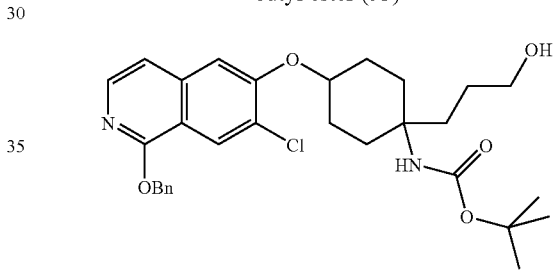

2.87 mL (1.43 mmol) of a 0.5M solution of 9-BBN in THF were added to a solution of 250 mg (0.48 mmol) of [1-allyl-4-(1-benzyloxy-7-chloro-isoquinolin-6-yloxy)-cyclohexyl]-

TABLE 3

| Example | Starting compound I | Starting compound II | Product | Chemical Name | [M + H$^+$] | $R_f$ [min] | Method |
|---|---|---|---|---|---|---|---|
| 50 | 35 | acetone | | 7-chloro-6-(trans-4-cyclopropyl-4-isopropylamino-cyclohexyloxy)-2H-isoquinolin-1-one | 375.2 | 2.49 | F |
| 51 | Mixture 34/35 | acetaldehyde | | 7-chloro-6-(4-cyclopropyl-4-ethylamino-cyclohexyloxy)-2H-isoquinolin-1-one | 361.2 | 0.90, 0.95 | C | carbamic acid tert-butyl ester (52) in 5 mL THF at 0° C. The reaction mixture was allowed to warm to room temperature over night, before being cooled to 0° C. Then, 5 mL of 3M aqueous sodium hydroxide and 5 mL of 30% aqueous hydrogen peroxide were added slowly, and the mixture was stirred for 5 h. The mixture was extracted twice with ethyl acetate, washed with water and saturated sodium chloride solution, dried over magnesium sulfate and concentrated in vacuo. 196 mg of the title compound 53 could be isolated as mixture of diastereoisomers in a purity sufficient for further conversion. $R_t$=2.05 min (Method C). Detected mass: 541.3 (M+H$^+$).

6-[cis-4-Amino-4-(3-hydroxy-propyl)-cyclohexyloxy]-7-chloro-2H-isoquinolin-1-one (54) and 6-[trans-4-amino-4-(3-hydroxy-propyl)-cyclohexyloxy]-7-chloro-2H-isoquinolin-1-one (55)

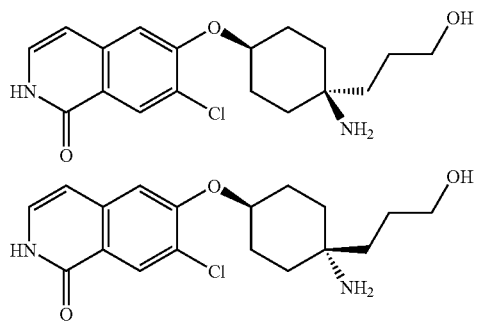

13.2 mg of 6-[cis-4-amino-4-(3-hydroxy-propyl)-cyclohexyloxy]-7-chloro-2H-isoquinolin-1-one (54) and 19.6 mg of 6-[trans-4-amino-4-(3-hydroxy-propyl)-cyclohexyloxy]-7-chloro-2H-isoquinolin-1-one (55) were synthesized as hydrochlorides from 184 mg (0.34 mmol) of [4-(1-benzyloxy-7-chloro-isoquinolin-6-yloxy)-1-(3-hydroxy-propyl)-cyclohexyl]-carbamic acid tert-butyl ester (53) using the standard deprotection procedure described for the synthesis of 6-(cis-4-amino-4-cyclopropyl-cyclohexyloxy)-7-chloro-2H-isoquinolin-1-one (41). The diastereoisomers were separated by preparative HPLC and lyophilized from 1N HCl and water. $R_t$=1.93 min (54), 2.01 min (55) (Method H). Detected mass: 351.2 (M+H$^+$).

[4-(1-Benzyloxy-7-chloro-isoquinolin-6-yloxy)-1-(2,3-dihydroxy-propyl)-cyclohexyl]-carbamic acid tert-butyl ester (56)

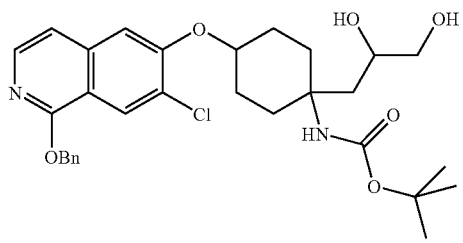 [SMILES: CC(C)(C)OC(=O)NC1(CC(O)CO)CCC(Oc2cc3ccnc(OCc4ccccc4)c3cc2Cl)CC1]

A solution of 100 mg (0.19 mmol) of [1-allyl-4-(1-benzyloxy-7-chloro-isoquinolin-6-yloxy)-cyclohexyl]-carbamic acid tert-butyl ester (52) in a mixture of 250 μL of water and 500 μL of acetone was treated with 36.2 mg (0.27 mmol) N-methylmorpholine oxide monohydrate and 24.0 μL (1.91 μmol) of a 2.5% solution of osmium tetroxide in tert-butanol. The mixture was stirred at room temperature until complete conversion was indicated by LCMS. The reaction was then quenched by addition of saturated aqueous sodium bisulfite, extracted with ethyl acetate, dried over magnesium sulfate and concentrated. 68 mg of crude [4-(1-benzyloxy-7-chloro-isoquinolin-6-yloxy)-1-(2,3-dihydroxy-propyl)-cyclohexyl]-carbamic acid tert-butyl ester (56) could be isolated as mixture of stereoisomers. $R_t$=1.92 min (Method C). Detected mass: 557.3 (M+H$^+$).

6-[4-amino-4-(2,3-dihydroxy-propyl)-cyclohexyloxy]-7-chloro-2H-isoquinolin-1-one (57)

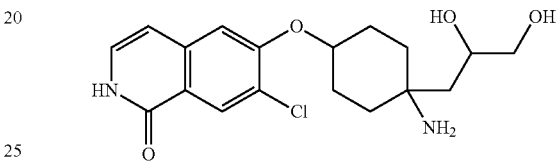

16.4 mg of 6-[4-amino-4-(2,3-dihydroxy-propyl)-cyclohexyloxy]-7-chloro-2H-isoquinolin-1-one (57) could be isolated as the hydrochloride of a mixture of stereoisomers according to the standard deprotection procedure described for the synthesis of 6-(cis-4-amino-4-cyclopropyl-cyclohexyloxy)-7-chloro-2H-isoquinolin-1-one (41) starting from 60 mg (0.11 mmol) of [4-(1-benzyloxy-7-chloro-isoquinolin-6-yloxy)-1-(2,3-dihydroxy-propyl)-cyclohexyl]-carbamic acid tert-butyl ester (56). $R_t$=0.80 min, 0.85 min (Method C). Detected mass: 367.2 (M+H$^+$).

[1-Allyl-5-(1-benzyloxy-7-chloro-isoquinolin-6-yloxy)-cyclooctyl]-carbamic acid tert-butyl ester (58)

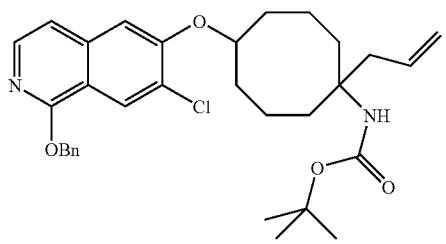 [SMILES: C=CCC1(NC(=O)OC(C)(C)C)CCCC(Oc2cc3ccnc(OCc4ccccc4)c3cc2Cl)CCC1]

Following the procedure described for the synthesis of [1-allyl-4-(1-benzyloxy-7-chloro-isoquinolin-6-yloxy)-cyclohexyl]-carbamic acid tert-butyl ester (52), 2.34 g of [1-allyl-5-(1-benzyloxy-7-chloro-isoquinolin-6-yloxy)-cyclooctyl]-carbamic acid tert-butyl ester (58) were synthesized as a mixture of diastereomers from 4.00 g (8.87 mmol) of 1-allyl-5-(1-benzyloxy-7-chloro-isoquinolin-6-yloxy)-cyclooctylamine (39), 2.90 g (13.3 mmol) of di-tert-butyl dicarbonate and 1.86 mL (13.3 mmol) of triethylamine. The title compound 58 was purified by silica gel chromatography. $R_f$=1.97 min (Method I). Detected mass: 551.0 (M+H$^+$).

[5-(1-Benzyloxy-7-chloro-isoquinolin-6-yloxy)-1-(3-hydroxy-propyl)-cyclooctyl]-carbamic acid tert-butyl ester (59)

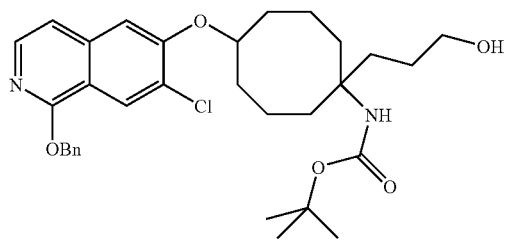 [SMILES: CC(C)(C)OC(=O)NC1(CCCO)CCCC(Oc2cc3ccnc(OCc4ccccc4)c3cc2Cl)CCC1]

1.14 g of [5-(1-benzyloxy-7-chloro-isoquinolin-6-yloxy)-1-(3-hydroxy-propyl)-cyclooctyl]-carbamic acid tert-butyl ester (59) were synthesized using the procedure described for the synthesis of [4-(1-benzyloxy-7-chloro-isoquinolin-6-yloxy)-1-(3-hydroxy-propyl)-cyclohexyl]-carbamic acid tert-butyl ester (53) starting from 1.17 g (2.12 mmol) of [1-allyl-5-(1-benzyloxy-7-chloro-isoquinolin-6-yloxy)-cyclooctyl]-carbamic acid tert-butyl ester (58) and 12.7 mL (6.37 mmol) of 9-BBN (0.5M solution in THF). $R_f$=1.71 min (Method I). Detected mass: 569.3 (M+H$^+$).

6-[5-Amino-5-(3-hydroxy-propyl)-cyclooctyloxy]-7-chloro-2H-isoquinolin-1-one (60)

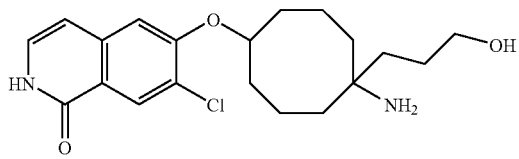 [SMILES: NC1(CCCO)CCCC(Oc2cc3cc[nH]c(=O)c3cc2Cl)CCC1]

168 mg of 6-[5-amino-5-(3-hydroxy-propyl)-cyclooctyloxy]-7-chloro-2H-isoquinolin-1-one (60) were synthesized as diastereomeric mixture as hydrochloride from 300 mg (0.53 mmol) of [5-(1-benzyloxy-7-chloro-isoquinolin-6-yloxy)-1-(3-hydroxy-propyl)-cyclooctyl]-carbamic acid tert-butyl ester (59) using the standard deprotection procedure described for the synthesis of 6-(cis-4-amino-4-cyclopropyl-cyclohexyloxy)-7-chloro-2H-isoquinolin-1-one (41). $R_f$=2.07 min, 2.12 min (Method H). Detected mass: 379.2 (M+H$^+$).

[5-(1-Benzyloxy-7-chloro-isoquinolin-6-yloxy)-1-(3-methoxy-propyl)-cyclooctyl]-carbamic acid tert-butyl ester (61)

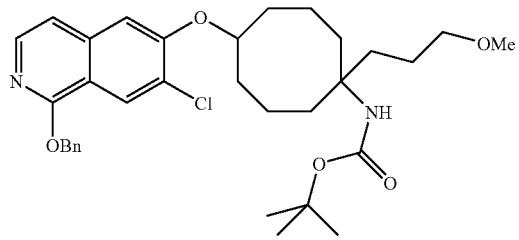 [SMILES: COCCCC1(NC(=O)OC(C)(C)C)CCCC(Oc2cc3ccnc(OCc4ccccc4)c3cc2Cl)CCC1]

A solution of 405 mg (0.71 mmol) of [5-(1-benzyloxy-7-chloro-isoquinolin-6-yloxy)-1-(3-hydroxy-propyl)-cyclooctyl]-carbamic acid tert-butyl ester (59) in 5 mL of THF was dropped into a suspension of 31.3 mg (0.78 mmol) of sodium hydride (60%) in 5 mL THF at 0° C. 88.6 µL (1.42 mmol) of iodomethane were added, and after stirring for 1 h at room temperature another 88.6 µL (1.42 mmol). The reaction mixture was stirred at room temperature until LCMS indicated complete conversion, then 5 mL of methanol were added and the volatiles removed in vacuo. The crude material was purified by silica gel chromatography. 196 mg of [5-(1-benzyloxy-7-chloro-isoquinolin-6-yloxy)-1-(3-methoxy-propyl)-cyclooctyl]-carbamic acid tert-butyl ester (61) as diastereomeric mixture could be isolated. $R_f$=1.89 min, 2.02 min (Method I). Detected mass: 583.3 (M+H$^+$).

6-[5-Amino-5-(3-methoxy-propyl)-cyclooctyloxy]-7-chloro-2H-isoquinolin-1-one (62)

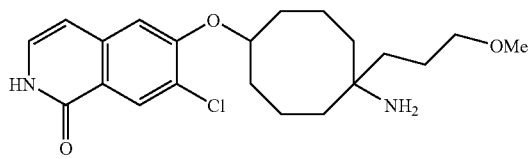 [SMILES: COCCCC1(N)CCCC(Oc2cc3cc[nH]c(=O)c3cc2Cl)CCC1]

Starting from 94 mg (0.16 mmol) of [5-(1-benzyloxy-7-chloro-isoquinolin-6-yloxy)-1-(3-methoxy-propyl)-cyclooctyl]-carbamic acid tert-butyl ester (61), 48 mg of a diastereomeric mixture of 6-[5-amino-5-(3-methoxy-propyl)-cyclooctyloxy]-7-chloro-2H-isoquinolin-1-one (62) were prepared as the hydrochloride following the standard deprotection procedure described for the synthesis of 6-(cis-4-amino-4-cyclopropyl-cyclohexyloxy)-7-chloro-2H-isoquinolin-1-one (41). $R_f$=2.38 min, 2.46 min (Method H). Detected mass: 393.2 (M+H$^+$).

[5-(1-Benzyloxy-7-chloro-isoquinolin-6-yloxy)-1-(2,3-dihydroxy-propyl)-cyclooctyl]-carbamic acid tert-butyl ester (63)

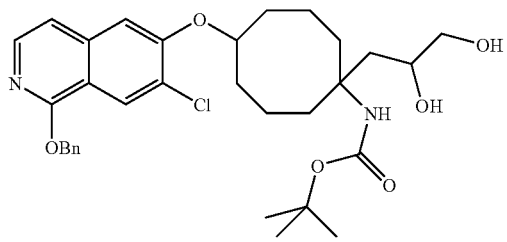 [SMILES: CC(C)(C)OC(=O)NC1(CC(O)CO)CCCC(Oc2cc3ccnc(OCc4ccccc4)c3cc2Cl)CCC1]

58 mg of [5-(1-benzyloxy-7-chloro-isoquinolin-6-yloxy)-1-(2,3-dihydroxy-propyl)-cyclooctyl]-carbamic acid tert-butyl ester (63) were synthesized using the procedure described for the synthesis of [4-(1-benzyloxy-7-chloro-isoquinolin-6-yloxy)-1-(2,3-dihydroxy-propyl)-cyclohexyl]-carbamic acid tert-butyl ester (56) starting from 90.0 mg (0.16 mmol) of [1-allyl-5-(1-benzyloxy-7-chloro-isoquinolin-6-yloxy)-cyclooctyl]-carbamic acid tert-butyl ester (58), 30.9 mg (0.23 mmol) N-methylmorpholine oxide monohydrate and 16.6 µL (1.63 μmol) of a 2.5% solution of osmium tetroxide in tert-butanol. $R_t$=1.58 min (Method I). Detected mass: 585.3 (M+H$^+$).

6-[5-Amino-5-(2,3-dihydroxy-propyl)-cyclooctyloxy]-7-chloro-2H-isoquinolin-1-one (64)

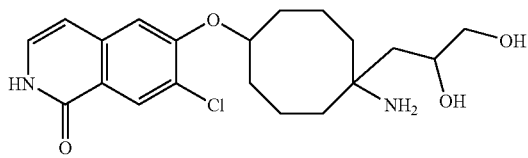 [SMILES: NC1(CC(O)CO)CCCC(Oc2cc3cc[nH]c(=O)c3cc2Cl)CCC1]

Starting from 50 mg (0.09 mmol) of [5-(1-benzyloxy-7-chloro-isoquinolin-6-yloxy)-1-(2,3-dihydroxy-propyl)-cyclooctyl]-carbamic acid tert-butyl ester (63) were prepared 12 mg of 6-[5-amino-5-(2,3-dihydroxy-propyl)-cyclooctyloxy]-7-chloro-2H-isoquinolin-1-one (64) as diastereomeric mixture as the hydrochloride following the standard deprotection procedure described for the synthesis of 6-(cis-4-amino-4-cyclopropyl-cyclohexyloxy)-7-chloro-2H-isoquinolin-1-one (41). $R_t$=0.82 min, 0.84 min (Method C). Detected mass: 395.2 (M+H$^+$).

7-Chloro-6-(1,4-dioxa-spiro[4.5]dec-8-yloxy)-2-(4-methoxy-benzyl)-2H-isoquinolin-1-one (65)

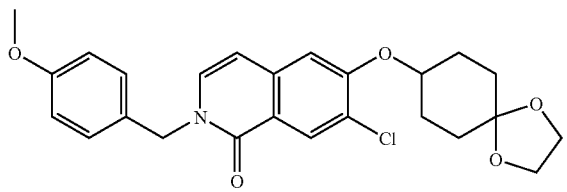 [SMILES: COc1ccc(Cn2ccc3cc(OC4CCC5(CC4)OCCO5)c(Cl)cc3c2=O)cc1]

1.49 g (9.44 mmol) of dioxa-spiro[4.5]decan-8-ol were dissolved in 30 ml of dimethyl acetamide and 283 mg (11.8 mmol) of sodium hydride (60%) were added. After stirring for 30 min at room temperature a solution of 2.50 g (7.87 mmol) of 7-chloro-6-fluoro-2-(4-methoxy-benzyl)-2H-isoquinolin-1-one (10) in 20 ml of dimethyl acetamide was added and stirring was continued at room temperature. After the reaction went to completion the solvent was removed under reduced pressure. The residue was dissolved in dichloromethane and washed with water. The organic layer was dried with magnesium sulfate and evaporated. Purification by silica gel chromatography yielded 1.84 g of the title compound. $R_t$=2.00 min (Method B). Detected mass: 456.1 (M+H$^+$).

7-Chloro-2-(4-methoxy-benzyl)-6-(4-oxo-cyclohexyloxy)-2H-isoquinolin-1-one (66)

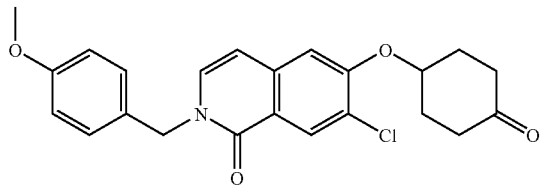 [SMILES: COc1ccc(Cn2ccc3cc(OC4CCC(=O)CC4)c(Cl)cc3c2=O)cc1]

1.00 g (2.19 mmol) of 7-chloro-6-(1,4-dioxa-spiro[4.5]dec-8-yloxy)-2-(4-methoxy-benzyl)-2H-isoquinolin-1-one (65) were stirred in 9 ml of 6 N HCl/acetone (1:2) at room temperature. After 2 h the reaction mixture was poured on saturated sodium bicarbonate solution and extracted with dichloromethane. The organic layer was dried with magnesium sulfate and evaporated. The crude product was purified by silica gel chromatography to give 630 mg of the title compound. $R_t$=1.81 min (Method B). Detected mass: 412.2 (M+H$^+$).

7-Chloro-6-(4-oxo-cyclohexyloxy)-2H-isoquinolin-1-one (67)

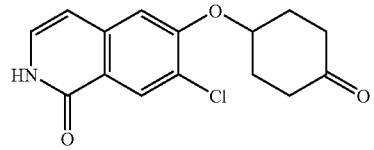 [SMILES: O=C1CCC(Oc2cc3cc[nH]c(=O)c3cc2Cl)CC1]

800 mg (1.94 mmol) of 7-chloro-6-(1,4-dioxa-spiro[4.5]dec-8-yloxy)-2-(4-methoxy-benzyl)-2H-isoquinolin-1-one (65) were dissolved in 3 mL of TFA and heated in a microwave oven at 150° C. for 3 h. Methanol was added and the reaction mixture was evaporated. The crude product was purified by silica gel chromatography to yield 230 mg of 7-chloro-6-(4-oxo-cyclohexyloxy)-2H-isoquinolin-1-one (67). $R_t$=1.02 min (Method C). Detected mass: 292.1 (M+H$^+$).

2-Methyl-propane-2-sulfinic acid {1-benzyl-4-[7-chloro-2-(4-methoxy-benzyl)-1-oxo-1,2-dihydro-isoquinolin-6-yloxy]-cyclohexyl}-amide (68)

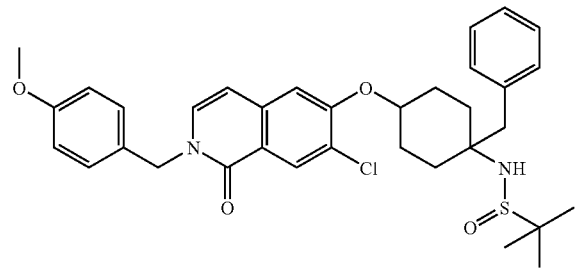 [SMILES: COc1ccc(Cn2ccc3cc(OC4CCC(Cc5ccccc5)(NS(=O)C(C)(C)C)CC4)c(Cl)cc3c2=O)cc1]

To a solution of 200 mg (0.49 mmol) of 7-chloro-2-(4-methoxy-benzyl)-6-(4-oxo-cyclohexyloxy)-2H-isoquinolin-1-one (66) in 6 mL of THF were added 61.9 mg (0.51 mmol) of 2-methyl-2-propanesulfineamide and 204 μL (0.97 mmol) of titanium(IV) ethoxide and the mixture was stirred at reflux overnight. The reaction mixture was cooled to 0° C. and 1.22 mL (2.43 mmol) of a 2 M solution of benzylmagnesium chloride in THF were added dropwise. The reaction mixture was stirred at room temperature until complete conversion was achieved. The reaction was poured onto water and the resulting suspension filtered through celite. The mixture was extracted with dichloromethane and the combined organic phases were concentrated in vacuo. The title compound was isolated as a mixture of diastereomers in a purity sufficient for further conversion. $R_t$=1.89 min, 1.93 min (Method C). Detected mass: 607.2 (M+H$^+$).

6-(4-amino-4-benzyl-cyclohexyloxy)-7-chloro-2H-isoquinolin-1-one (69)

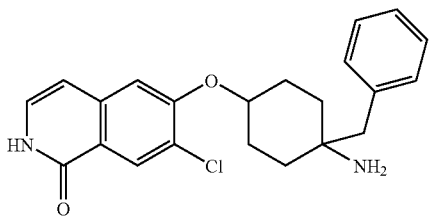 [SMILES: NC1(Cc2ccccc2)CCC(Oc2cc3cc[nH]c(=O)c3cc2Cl)CC1]

50 mg (0.08 mmol) of 2-methyl-propane-2-sulfinic acid {1-benzyl-4-[7-chloro-2-(4-methoxy-benzyl)-1-oxo-1,2-dihydro-isoquinolin-6-yloxy]-cyclohexyl}-amide (crude, 68) were dissolved in 1 mL of trifluoroacetic acid containing 200 µL of water and heated in a microwave oven at 150° C. for 1 h. Methanol was added and the reaction mixture was evaporated. The crude product was separated via preparative HPLC. The resultant trifluoroacetates were taken up in 1N HCl twice and lyophilized. The respective residues were redissolved in water and lyophilized again to yield 3 mg and 2 mg, respectively, of the separated diastereoisomers of 6-(4-amino-4-benzyl-cyclohexyloxy)-7-chloro-2H-isoquinolin-1-one (69) as hydrochlorides. $R_t$=1.14 min, 1.21 min (Method B). Detected mass: 383.2 (M+H$^+$).

2-Methyl-propane-2-sulfinic acid [4-(7-chloro-1-oxo-1,2-dihydro-isoquinolin-6-yloxy)-1-phenyl-cyclohexyl]-amide (70)

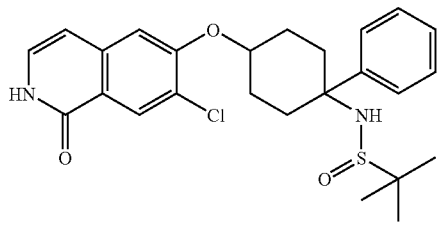 [SMILES: CC(C)(C)S(=O)NC1(c2ccccc2)CCC(Oc2cc3cc[nH]c(=O)c3cc2Cl)CC1]

To a solution of 100 mg (0.34 mmol) of 7-chloro-6-(4-oxo-cyclohexyloxy)-2H-isoquinolin-1-one (67) in 3 mL of THF were added 44 mg (0.36 mmol) of 2-methyl-2-propane-sulfineamide and 144 µL (0.69 mmol) of titanium(IV) ethoxide and the mixture was stirred overnight at reflux. The reaction mixture was cooled to 0° C. and 0.86 mL (1.72 mmol) of a 2M solution of phenylmagnesium chloride in THF were added dropwise. The reaction mixture was stirred at room temperature until complete conversion was achieved. The reaction was poured onto water and the resulting suspension was filtered through celite. The mixture was extracted with dichloromethane/2-propanol (3:1) and the combined organic phases were concentrated in vacuo. The title compound was isolated as an inseparable mixture of diastereomers in a purity sufficient for further conversion. $R_t$=1.38 min (Method C). Detected mass: 473.2 (M+H$^+$).

6-(4-Amino-4-phenyl-cyclohexyloxy)-7-chloro-2H-isoquinolin-1-one (71)

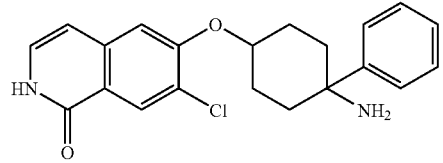 [SMILES: NC1(c2ccccc2)CCC(Oc2cc3cc[nH]c(=O)c3cc2Cl)CC1]

4.5 mg of the title compound 71 were prepared as diastereomeric mixture from 190 mg (0.40 mmol) of 2-methyl-propane-2-sulfinic acid [4-(7-chloro-1-oxo-1,2-dihydro-isoquinolin-6-yloxy)-1-phenyl-cyclohexyl]-amide (crude, 70) by stirring in a mixture of 2-propanol/0.5N aqueous HCl (2:1) until complete conversion. The reaction mixture was concentrated and purified by preparative HPLC. The resultant trifluoroacetate was taken up in 1N HCl twice and lyophilized. The respective residue was redissolved in water and lyophilized again to give the hydrochloride. $R_t$=0.91 min, 0.94 min (Method C). Detected mass: 369.2 (M+H$^+$).

5-Cyano-5-(4-fluoro-phenyl)-2-oxo-cyclohexanecarboxylic acid methyl ester (72)

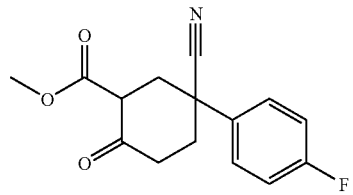 [SMILES: COC(=O)C1CC(C#N)(c2ccc(F)cc2)CCC1=O]

70 mL of methyl acrylate and 44.4 mL of 4-fluorophenylacetonitrile were dissolved in 200 mL of THF and 50 mL of methanol. 150 mL of a 30% solution of sodium methylate in methanol were added slowly. The mixture was stirred at room temperature for 15 h and for 4 h at 50° C. The mixture was cooled to room temperature and poured onto cooled 2N HCl. The aqueous layer was washed with ethyl acetate three times, the combined organic layers were extracted with water and brine, dried over sodium sulfate and evaporated to dryness to give 101.5 g of crude product, that was sufficiently pure for further conversion. $R_t$=1.60 min (Method C). Detected mass: 276.2 (M+H$^+$).

1-(4-Fluoro-phenyl)-4-oxo-cyclohexanecarbonitrile (73)

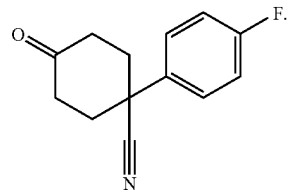 [SMILES: N#CC1(c2ccc(F)cc2)CCC(=O)CC1]

102.5 g of crude 5-Cyano-5-(4-fluoro-phenyl)-2-oxo-cyclohexanecarboxylic acid methyl ester (72) were dissolved in 680 mL of ethanol. 170 mL of conc. hydrochloric acid were added and the reaction mixture was refluxed for 40 h. The mixture was evaporated to dryness, the residue was taken up in water and extracted with dichloromethane. The combined organic layers were extracted with brine, dried over sodium sulfate and evaporated to dryness. The crude product was purified by silica gel chromatography to give 50.4 g of the desired product. $R_t$=1.26 min (Method C). Detected mass: 218.2 (M+H$^+$).

8-(4-Fluoro-phenyl)-1,4-dioxa-spiro[4.5]decane-8-carbonitrile (74)

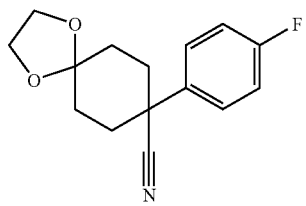 [SMILES: N#CC1(c2ccc(F)cc2)CCC2(CC1)OCCO2]

25 g of 1-(4-Fluoro-phenyl)-4-oxo-cyclohexanecarbonitrile (73) were dissolved in 850 mL of toluene. 9 mL of ethylene glycol and 1.5 g of p-toluene sulfonic acid were added and the mixture was refluxed at a Dean-Stark apparatus for 6 h. The mixture was allowed to cool down to room temperature and extracted twice with saturated sodium bicarbonate solution and once with brine. The organic layer was dried over sodium sulfate and evaporated to dryness to give 30.15 g of crude product, that was sufficiently pure for further conversion. $R_t$=1.47 min (Method C). Detected mass: 262.2 (M+H$^+$).

8-(4-Fluoro-phenyl)-1,4-dioxa-spiro[4.5]decane-8-carboxylic acid (75)

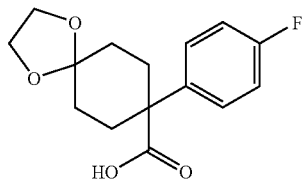 [SMILES: O=C(O)C1(c2ccc(F)cc2)CCC2(CC1)OCCO2]

30.1 g of 8-(4-Fluoro-phenyl)-1,4-dioxa-spiro[4.5]decane-8-carbonitrile (74) were dissolved in 91 mL of ethylene glycol. 19.4 g of powdered potassium hydroxide were added and the mixture was heated to reflux until conversion was complete. The mixture was allowed to cool down to room temperature and poured into 300 mL of water. The pH was adjusted to 4 by addition of 2N HCl and the aqueous layer was extracted With ethyl acetate. The organic layer was extracted with brine, dried over magnesium sulfate and evaporated to dryness to give 29.85 g of the desired product. $R_t$=1.81 min (Method B). Detected mass: 281.2 (M+H$^+$).

[8-(4-Fluoro-phenyl)-1,4-dioxa-spiro[4.5]dec-8-yl]-carbamic acid benzyl ester (76)

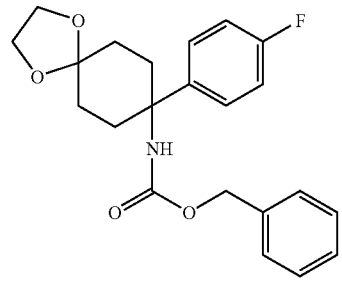 [SMILES: O=C(NC1(c2ccc(F)cc2)CCC2(CC1)OCCO2)OCc1ccccc1]

3 g of 8-(4-Fluoro-phenyl)-1,4-dioxa-spiro[4.5]decane-8-carboxylic acid (75) and 3.3 mL of triethyl amine were dissolved in 50 mL of dry toluene. At 0° C. 2.83 mL of diphenyl phosphoryl azide was added dropwise. The mixture was stirred at room temperature until conversion was complete, then the solution was heated to 90° C. until gas evolution stopped. 3.4 mL of benzyl alcohol were added and stirring at 90° C. was continued for another 18 h. The mixture was allowed to cool down to room temperature and 500 mL of ethyl acetate were added. The organic layer was extracted two times with 1N HCl and once with brine, dried over magnesium sulfate and evaporated to dryness. The crude product was purified by silica gel chromatography to give 2.85 g of the desired product. $R_t$=2.52 min (Method E). Detected mass: 386.2 (M+1H$^+$).

[1-(4-Fluoro-phenyl)-4-oxo-cyclohexyl]-carbamic acid benzyl ester (77)

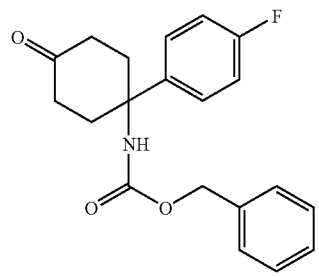 [SMILES: O=C1CCC(NC(=O)OCc2ccccc2)(c2ccc(F)cc2)CC1]

2.75 g of [8-(4-Fluoro-phenyl)-1,4-dioxa-spiro[4.5]dec-8-yl]-carbamic acid benzyl ester (76) were dissolved in 30 mL of acetone and 15 mL of 5N HCl. When conversion was complete, the mixture was carefully poured into sat. sodium bicarbonate solution. The aqueous layer was extracted twice with dichloromethane, The combined organic layer was extracted with brine, dried over magnesium sulfate and evaporated to dryness to give 2.36 g of the desired product. $R_t$=2.35 min (Method E). Detected mass: 324.2.2 (M+H—H$_2$O$^+$).

[1-(4-Fluoro-phenyl)-4-hydroxy-cyclohexyl]-carbamic acid benzyl ester (78)

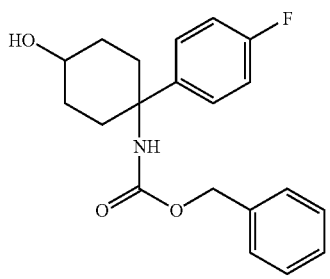 [SMILES: O=C(NC1(c2ccc(F)cc2)CCC(O)CC1)OCc1ccccc1]

1.5 g of [1-(4-Fluoro-phenyl)-4-oxo-cyclohexyl]-carbamic acid benzyl ester (77) were dissolved in 30 mL of dry THF and 182 mg of sodium borohydride were added. When conversion was complete, the mixture was poured into 15 mL of water. pH was adjusted to 2 by addition of 2N HCl and the aqueous layer was extracted with ethyl acetate. The combined organic layer was extracted with brine, dried over magnesium sulfate and evaporated to dryness to give 1.38 g of the desired product as a mixture of cis and trans isomers, the cis isomer (referring to the position of alcohol and Z-amine) being the major one. $R_t$=2.20 min (Method E). Detected mass: 344.2 (M+H$^+$).

4-Amino-4-(4-fluoro-phenyl)-cyclohexanol (79)

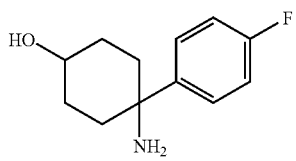 [SMILES: NC1(c2ccc(F)cc2)CCC(O)CC1]

0.5 g of [1-(4-Fluoro-phenyl)-4-hydroxy-cyclohexyl]-carbamic acid benzyl ester (78) were dissolved in 50 mL of methanol and 57 mg of palladium on charcoal (10%) were added. The mixture was stirred under a hydrogen atmosphere until conversion was complete. The catalyst was filtered off and the organic layer was evaporated to dryness to give 290 mg of the desired product. $R_t$=0.73 min (Method E). Detected mass: 175.2 (M+H—H$_2$O—NH$_3^+$).

Cis-4-(1-Benzyloxy-7-chloro-isoquinolin-6-yloxy)-1-(4-fluoro-phenyl)-cyclohexylamine (80)

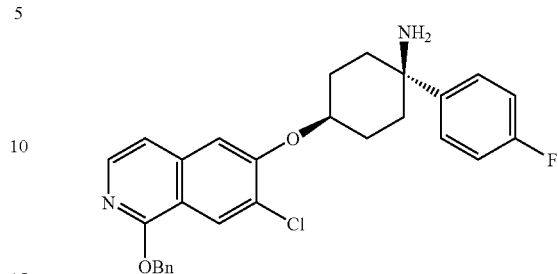

285 mg of 4-Amino-4-(4-fluoro-phenyl)-cyclohexanol (79) was codistilled with toluene twice and dissolved in 8 mL of dry dimethyl acetamide under argon. 98 mg of sodium hydride (95%) and 431 mg of 1-benzyloxy-7-chloro-6-fluoro-isoquinoline (11) were added and stirring was continued overnight. Water (ca. 10 mL) was added carefully and the mixture was extracted with dichloromethane:isopropanol (3:1). The combined organic layer was extracted twice with water and once with brine, dried over magnesium sulfate and evaporated to dryness. The crude material was taken up in water and lyophilized to remove remaining DMA, the remainder was taken up in a small amount of methanol. The remaining precipitate was filtered off to yield 337 mg of the desired product as the hydrochloride of the cis isomer (referring to the position of alcohol and amine). $R_t$=2.35 min (Method E). Detected mass: 477.2 (M+H$^+$). Additional material could, if wanted, be isolated from silica gel chromatography of the remainder resulting from evaporation of the mother liquor.

6-[cis-4-Amino-4-(4-fluoro-phenyl)-cyclohexyloxy]-7-chloro-2H-isoquinolin-1-one (81)

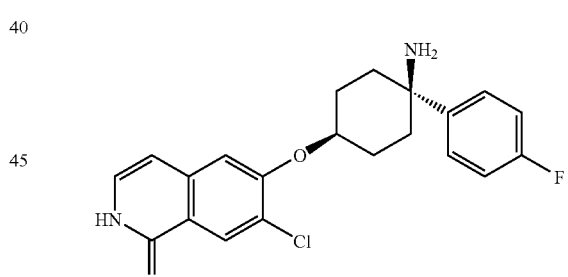

316 mg of (cis-4-(1-Benzyloxy-7-chloro-isoquinolin-6-yloxy)-1-(4-fluoro-phenyl)-cyclohexylamine (80) were suspended in 3.5 mL of isopropanol and 3.5 mL of 1N HCl were added. The mixture was stirred overnight and evaporated to dryness. Water was added and the mixture was lyophilized. Purification could be achieved by HPLC separation or tituration of the crude product with small amounts of isopropanol. In this case, tituration led to isolation of 254 mg of the desired product as the hydrochloride. $R_t$=1.72 min (Method E). Detected mass: 387.2 (M+H$^+$).

Sometimes, small amounts of the corresponding trans isomer could be isolated by HPLC purification of the evaporated mother liquor The following examples were prepared as the hydrochlorides following a similar sequence as described for example 81, starting from the designated starting materials.

TABLE 4

| Example | Iso-quinoline | Benzyl nitrile | Product | Chemical Name | [M + H+] | Rtl [min] | Method |
|---|---|---|---|---|---|---|---|
| 82 | 11 | benzyl-nitrile | | 6-(cis-4-Amino-4-phenyl-cyclohexyl)-7-chloro-2H-isoquinolin-1-one | 369.2 | 0.91 | C |
| 83 | 11 | benzyl-nitrile | | 6-(trans-4-Amino-4-phenyl-cyclohexyloxy)-7-chloro-2H-isoquinolin-1-one | 352.1 (M + H − NH3+) | 0.98 | C |
| 84 | 11 | 4-(tri-fluoro-methyl)-benzyl-nitrile | ClH | 6-[cis-4-Amino-4-(4-trifluoromethyl-phenyl)-cyclohexyloxy]-7-chloro-2H-isoquinolin-1-one | 436.1 | 1.89 | E |
| 85 | 15 | 4-fluoro-benzyl-nitrile | | 6-[cis-4-Amino-4-(4-fluoro-phenyl)-cyclohexyloxy]-4-benzyl-7-methyl-2H-isoquinolin-1-one | 457.3 | 3.43 | J |
| 86 | 11 | 3,5-dimethyl-benzyl-nitrile | | 6-[4-Amino-4-(3,5-dimethyl-phenyl)-cyclohexyloxy]-7-chloro-2H-isoquinolin-1-one | 397.2 | 2.60 | F |

TABLE 4-continued

| Example | Iso-quinoline | Benzyl nitrile | Product | Chemical Name | [M + H⁺] | $R_t$ [min] | Method |
|---|---|---|---|---|---|---|---|
| 87 | 14 | 3,5-dimethyl-benzyl-nitrile | | 6-[4-Amino-4-(3,5-dimethyl-phenyl)-cyclohexyloxy]-7-methyl-2H-isoquinolin-1-one | 377.4 | 1.03 | C |
| 88 | 11 | 2,4-difluoro benzyl-nitrile | | 6-[cis-4-Amino-4-(2,4-difluoro-phenyl)-cyclohexyloxy]-7-chloro-2H-isoquinolin-1-one | 404.1 | 2.42 | F |
| 89 | 11 | 2,6-difluoro-benzyl-nitrile | | 6-[4-Amino-4-(2,6-difluoro-phenyl)-cyclohexyloxy]-7-chloro-2H-isoquinolin-1-one | 404.1 | 2.56 | J |
| 90 | 14 | 2,6-difluoro-benzyl-nitrile | | 6-[4-Amino-4-(2,6-difluoro-phenyl)-cyclohexyloxy]-7-methyl-2H-isoquinolin-1-one | 384.2 | 2.69 | E |
| 91 | 14 | 4F-benzyl-nitrile | | 6-[4-Amino-4-(4-fluoro-phenyl)-cyclohexyloxy]-7-methyl-2H-isoquinolin-1-one | 368.2 | 0.94 | C |
| 92 | 15 | 2,6-difluoro-benzyl-nitrile | | 6-[4-Amino-4-(2,6-difluoro-phenyl)-cyclohexyloxy]-4-benzyl-7-methyl-2H-isoquinolin-1-one | 475.3 | 1.32 | C |

TABLE 4-continued

| Example | Iso-quinoline | Benzyl nitrile | Product | Chemical Name | [M + H⁺] | $R_t$ [min] | Method |
|---|---|---|---|---|---|---|---|
| 93 | 14 | 2,4-difluoro-benzyl-nitrile | | 6-[4-Amino-4-(2,4-difluoro-phenyl)-cyclohexyloxy]-7-methyl-2H-isoquinolin-1-one | 484.2 | 2.47 | J |
| 94 | 11 | 2-F-benzyl-nitrile | | 6-[4-Amino-4-(2-fluoro-phenyl)-cyclohexyloxy]-7-chloro-2H-isoquinolin-1-one | 387.3 | 2.70 | J |
| 95 | 14 | 2-F-benzyl-nitrile | | 6-[4-Amino-4-(2-fluoro-phenyl)-cyclohexyloxy]-7-methyl-2H-isoquinolin-1-one | 367.3 | 2.71 | J |
| 96 | 11 | 3-methyl-benzyl-nitrile | | 6-(4-Amino-4-m-tolyl-cyclohexyloxy)-7-chloro-2H-isoquinolin-1-one | 366 (M + H⁺ − NH₃) | 1.05 | C |

Bicyclo[3.3.1]nonan-2,6-dione-monoethylene ketal (97)

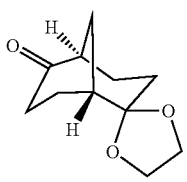 [SMILES: O=C1CC[C@@H]2C[C@H]1CCC21OCCO1]

5 g of bicyclo[3.3.1]nonane-2,6-dione were suspended in 27 mL of dry ethylene glycol and 283 mg of p toluene sulfonic acid were added. After 2 h all starting material was converted. 80 mL of water were added and the aqueous layer was extracted with ethyl acetate. The combined organic layer was washed with water and sat. sodium bicarbonate, dried over sodium sulfate and evaporated to dryness. The crude product was purified by silica gel chromatography to give 0.5 g of the desired product along with 6.75 g of the diketal. The diketal was dissolved in 135 mL of acetone and 13.5 mL of 2M HCl were added. The mixture was allowed to stir at room temperature for 1 h. The mixture was neutralized by addition of 2 N NaOH, the acetone was removed in vacuo and the remaining aqueous layer was extracted with ethyl acetate and dichloromethane. The organic layer was dried over sodium sulfate and evaporated to dryness. The crude product was purified by chromatography to give another 4.38 g of the desired product. $R_t$=0.84 min (Method C). Detected mass: 197.2 (M+H⁺).

6-Amino-bicyclo[3.3.1]nonan-2-one ethylene ketal (98)

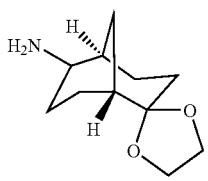 [SMILES: NC1CC[C@@H]2C[C@H]1CCC21OCCO1]

4.2 g of bicyclo[3.3.1]nonan-2,6-dione-monoethylene ketal (97) were dissolved in 54 mL of 2M ammonia in ethanol and 12.6 mL of titanium(IV) isopropoxide were added. The mixture is stirred at 60° C. overnight. Heating was continued until no further conversion was observed, another 22 mL of ammonia in ethanol was added portionwise over the course of the reaction. The mixture was cooled to room temperature and 1.21 g of sodium borohydride were added portionwise. The mixture was stirred for 2 h and then poured into 100 mL of 2M aqueous ammonia. The formed precipitate was filtered over celite and washed with ethyl acetate. The aqueous layer was extracted with ethyl acetate, the combined organic layer was dried over sodium sulfate and evaporated to dryness. The crude product was taken up in water and lyophilized to give 1.97 g of the desired product. $R_t$=0.52 min (Method C). Detected mass: 198.3 (M+H$^+$).

6-Benzyloxycarbonylamino-bicyclo[3.3.1]nonan-2-one ethylene ketal (99)

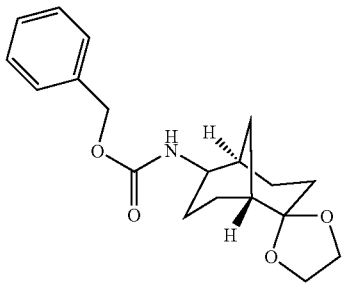 [SMILES: O=C(NC1CC[C@@H]2C[C@H]1CCC21OCCO1)OCc1ccccc1]

1.97 g of 6-Amino-bicyclo[3.3.1]nonan-2-one ethylene ketal (98) were dissolved in 30 mL of dry dichloromethane and 1.52 mL of dry triethylamine and 1.42 mL of benzylchloroformate were added. The mixture was stirred overnight, taken up in water and extracted three times with ethyl acetate. The combined organic layer was dried over sodium sulfate and evaporated to dryness. The crude product was purified by chromatography to give 0.92 g of the desired product. $R_t$=3.18 min (Method E). Detected mass: 332.2 (M+H$^+$).

(6-Oxo-bicyclo[3.3.1]non-2-yl)-carbamic acid benzyl ester (100)

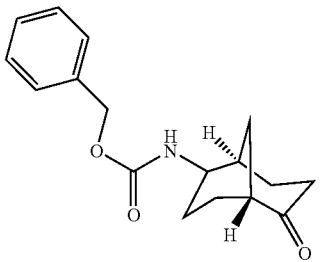 [SMILES: O=C(NC1CC[C@@H]2C[C@H]1CCC2=O)OCc1ccccc1]

915 mg of 6-Benzyloxycarbonylamino-bicyclo[3.3.1]nonan-2-one ethylene ketal (99) were suspended in 7.6 mL of acetone and 2.9 mL of 5N HCl were added. The mixture was stirred for 2 h, the acetone was evaporated and the remaining liquid was slowly added to sat. NaHCO$_3$. The aqueous layer was extracted with dichloromethane three times. The combined organic layer was dried over sodium sulfate and evaporated to dryness to give 0.79 g of the desired product. $R_t$=2.87 min (Method E). Detected mass: 288.2 (M+H$^+$).

(6-Hydroxy-bicyclo[3.3.1]non-2-yl)-carbamic acid benzyl ester (101)

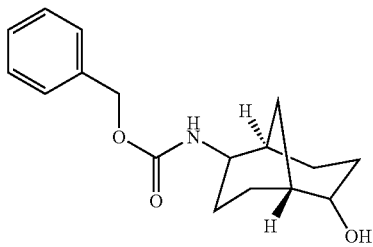 [SMILES: O=C(NC1CC[C@@H]2C[C@H]1CCC2O)OCc1ccccc1]

780 mg of (6-Oxo-bicyclo[3.3.1]non-2-yl)-carbamic acid benzyl ester (100) were dissolved in 14 mL of THF under argon, cooled to 0° C. and 113 mg of sodium borohydride were added. The mixture was stirred for 2 h at 0° C., water was added and the pH of solution was adjusted to 2 by addition of 2M HCl. The aqueous layer was extracted with ethyl acetate three times. The combined organic layer was dried over sodium sulfate and evaporated to dryness to give 0.72 g of the desired product. $R_t$=1.23 min (Method C). Detected mass: 290.3 (M+H$^+$).

6-Amino-bicyclo[3.3.1]nonan-2-ol (102)

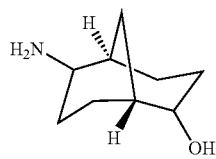

0.72 g of (6-Hydroxy-bicyclo[3.3.1]non-2-yl)-carbamic acid benzyl ester (101) were dissolved in 50 mL of methanol and 97 mg of palladium on charcoal (10%) were added. The mixture was stirred under a hydrogen atmosphere until conversion was complete. The catalyst was filtered off and the organic layer was evaporated to dryness to give 407 mg of the desired product. $R_t$=0.17 min (Method C). Detected mass: 156.2 (M+H$^+$).

The following examples were prepared using the designated isoquinolines and amino alcohols, following a similar procedure as described for the synthesis of 80 and 81.

TABLE 5

| Example | Amino-alcohol | isoquinoline | Product | Chemical Name | [M + H$^+$] | $R_t$ [min] | Method |
|---|---|---|---|---|---|---|---|
| 103 | 102 | 11 | | 6-((1R,5R)-6-Amino-bicyclo[3.3.1]non-2-yloxy)-7-chloro-2H-isoquinolin-1-one | 33.12 | 2.06 | E |

TABLE 5-continued

| Example | Amino-alcohol | isoquinoline | Product | Chemical Name | [M + H⁺] | $R_t$, [min] | Method |
|---|---|---|---|---|---|---|---|
| 104 | 102 | 14 | | 6-((1R,5R)-6-Amino-bicyclo[3.3.1]non-2-yloxy)-7-methyl-2H-isoquinolin-1-one | 312.18 | 2.03 | E |
| 105 | 102 | 15 | | 6-((1R,5R)-6-Amino-bicyclo[3.3.1]non-2-yloxy)-4-benzyl-7-methyl-2H-isoquinolin-1-one | 402.23 | 2.91 | J |
| 106 | 4-Amino-bicyclo[2.2.2]octan-1-ol | 11 | | 6-(4-Amino-bicyclo[2.2.2]oct-1-yloxy)-7-chloro-2H-isoquinolin-1-one | 319.0 | 1.49 | E |

6-(4-Aminomethyl-4-phenyl-cyclohexyloxy)-7-chloro-2H-isoquinolin-1-one (108)

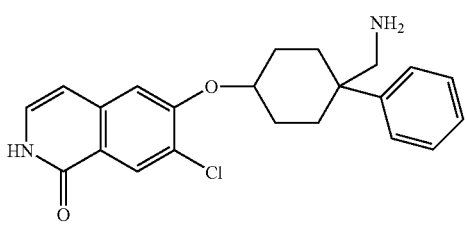 [SMILES: NCC1(c2ccccc2)CCC(Oc2cc3cc[nH]c(=O)c3cc2Cl)CC1]

110 mg of 4-aminomethyl-4-phenyl-cyclohexanol were dissolved in 4 mL of dry DMF and 60 mg of sodium hydride were added. The mixture was allowed to stir for 20 minutes, then 143 mg of 1-Benzyloxy-7-chloro-6-fluoro-isoquinoline (11) were added. Stirring at room temperature was continued until conversion was complete. Ethyl acetate and saturated sodium chloride solution were added. The phases were separated and the aqueous phase was extracted with ethyl acetate. The combined organic phases were dried over sodium sulfate, concentrated and the resultant residue was purified via preparative HPLC. The coupling product was dissolved in 5 mL of trifluoroacetic acid and allowed to stand overnight.

The obtained TFA salt was dissolved in 2 N HCl and evaporated. After dissolving the residue in water and lyophilization, 78 mg of the title compound was isolated as the hydrochloride. $R_t$=1.17 min (Method B). Detected mass: 383.2 (M+H⁺).

6-[4-Aminomethyl-4-(4-chloro-phenyl)-cyclohexyloxy]-7-chloro-2H-isoquinolin-1-one (109)

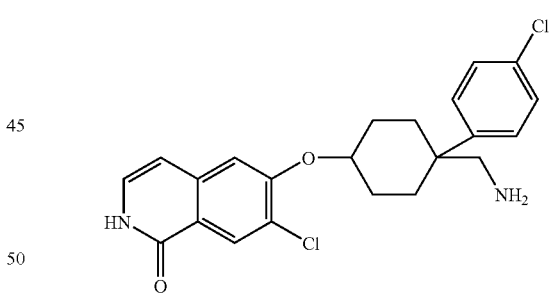

110 mg of 4-aminomethyl-4-(4-chloro-phenyl)-cyclohexanol were dissolved in 3 mL of dry DMF and 40 mg of sodium hydride were added. The mixture was allowed to stir for 20 minutes, then 127 mg of 7-chloro-6-fluoro-2-(4-methoxy-benzyl)-2H-isoquinolin-1-one (10) were added. Stirring at room temperature was continued until conversion was complete. Ethyl acetate and saturated sodium chloride solution were added. The phases were separated and the aqueous phase was extracted with ethyl acetate. The combined organic phases were dried over sodium sulfate, concentrated and the resultant residue was purified via preparative HPLC to give 121 mg of the coupling product, which was dissolved in 2 mL of trifluoroacetic acid and heated in a microwave oven at 150° C. until complete conversion was observed. The mixture was distributed between 1N HCl and dichloromethane. The product containing layer, which in this case was the organic layer, was concentrated (otherwise lyophilized) and the crude material was purified by HPLC to give 8 mg of the desired product as the trifluoroacetate. $R_t$=1.25 min (Method B). Detected mass: 417.1 (M+H$^+$).

6-[4-Aminomethyl-4-(3-chloro-phenyl)-cyclohexyloxy]-7-chloro-2H-isoquinolin-1-one (110)

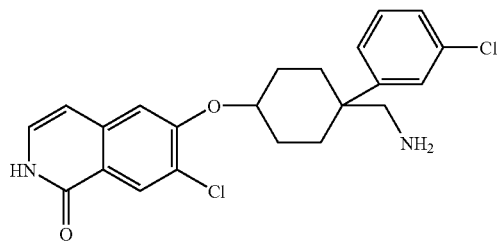 [SMILES: NCC1(c2cccc(Cl)c2)CCC(Oc2cc3cc[nH]c(=O)c3cc2Cl)CC1]

Starting from 7-chloro-6-fluoro-2-(4-methoxy-benzyl)-2H-isoquinolin-1-one (10) and 4-aminomethyl-4-(3-chloro-phenyl)-cyclohexanol, 6-[4-aminomethyl-4-(3-chloro-phenyl)-cyclohexyloxy]-7-chloro-2H-isoquinolin-1-one (110) could be obtained as the trifluoroacetate as described for compound 109. $R_t$=1.24 min (Method B). Detected mass: 417.1 (M+H$^+$).

6-[4-Aminomethyl-4-(3-methyl-phenyl)-cyclohexyloxy]-7-chloro-2H-isoquinolin-1-one (111)

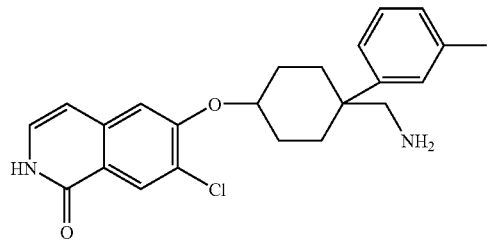 [SMILES: Cc1cccc(C2(CN)CCC(Oc3cc4cc[nH]c(=O)c4cc3Cl)CC2)c1]

Starting from 7-chloro-6-fluoro-2-(4-methoxy-benzyl)-2H-isoquinolin-1-one (10) and 4-aminomethyl-4-(3-methyl-phenyl)-cyclohexanol, 6-[4-aminomethyl-4-(3-methyl-phenyl)-cyclohexyloxy]-7-chloro-2H-isoquinolin-1-one (111) could be obtained as hydrochloride as described for compound 109. $R_t$=1.22 min (Method B). Detected mass: 397.2 (M+H$^+$).

6-[4-Aminomethyl-4-(3,4-dimethoxy-phenyl)-cyclohexyloxy]-7-chloro-2H-isoquinolin-1-one (112)

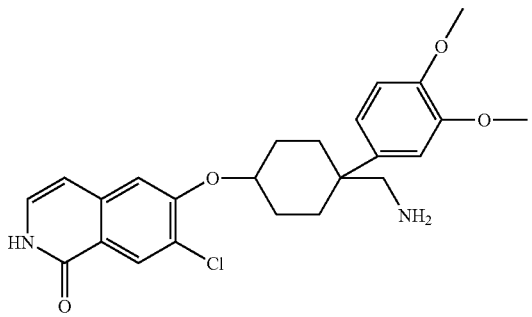 [SMILES: COc1ccc(C2(CN)CCC(Oc3cc4cc[nH]c(=O)c4cc3Cl)CC2)cc1OC]

Starting from 7-chloro-6-fluoro-2-(4-methoxy-benzyl)-2H-isoquinolin-1-one (10) and 4-aminomethyl-4-(3,4-dimethoxy-phenyl)-cyclohexanol, 6-[4-aminomethyl-4-(3,4-dimethoxy-phenyl)-cyclohexyloxy]-7-chloro-2H-isoquinolin-1-one (112) could be obtained as hydrochloride as described for compound 109. $R_t$=1.13 min (Method B). Detected mass: 443.2 (M+H$^+$).

6-[4-Aminomethyl-4-(4-fluoro-phenyl)-cyclohexyloxy]-7-chloro-2H-isoquinolin-1-one (113)

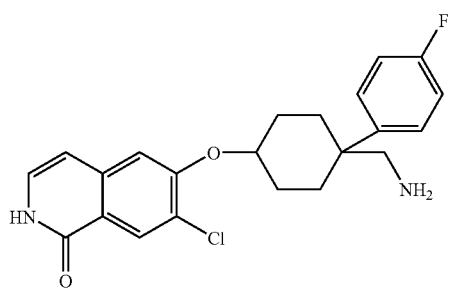 [SMILES: NCC1(c2ccc(F)cc2)CCC(Oc2cc3cc[nH]c(=O)c3cc2Cl)CC1]

Starting from 7-chloro-6-fluoro-2-(4-methoxy-benzyl)-2H-isoquinolin-1-one (10) and 4-aminomethyl-4-(4-fluoro-phenyl)-cyclohexanol, 6-[4-aminomethyl-4-(4-fluoro-phenyl)-cyclohexyloxy]-7-chloro-2H-isoquinolin-1-one (113) could be obtained as the hydrochloride as described for compound 109. $R_t$=1.23 min (Method B). Detected mass: 401.1 (M+H$^+$).

6-[4-Aminomethyl-4-(4-methoxy-phenyl)-cyclohexyloxy]-7-chloro-2H-isoquinolin-1-one (114)

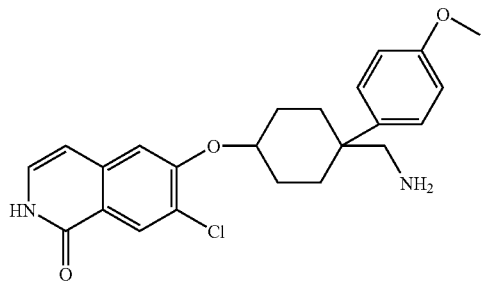 [SMILES: COc1ccc(C2(CN)CCC(Oc3cc4cc[nH]c(=O)c4cc3Cl)CC2)cc1]

Starting from 7-chloro-6-fluoro-2-(4-methoxy-benzyl)-2H-isoquinolin-1-one (10) and 4-aminomethyl-4-(4-methoxy-phenyl)-cyclohexanol, 6-[4-aminomethyl-4-(4-methoxy-phenyl)-cyclohexyloxy]-7-chloro-2H-isoquinolin-1-one (114) could be obtained as the trifluoroacetate as described for compound 109. $R_t$=1.24 min (Method B). Detected mass: 413.2 (M+H$^+$).

6-[4-Aminomethyl-4-(4-methyl-phenyl)-cyclohexyloxy]-7-chloro-2H-isoquinolin-1-one (115)

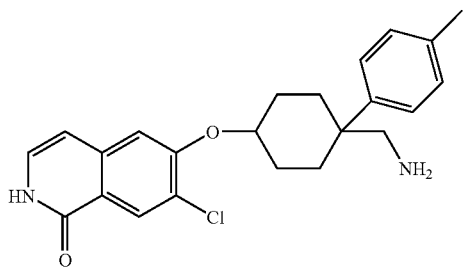 [SMILES: Cc1ccc(C2(CN)CCC(Oc3cc4cc[nH]c(=O)c4cc3Cl)CC2)cc1]

Starting from 7-chloro-6-fluoro-2-(4-methoxy-benzyl)-2H-isoquinolin-1-one (10) and 4-Aminomethyl-4-(4-methyl-phenyl)-cyclohexanol, 6-[4-aminomethyl-4-(4-methyl-phenyl)-cyclohexyloxy]-7-chloro-2H-isoquinolin-1-one (115) could be obtained as the trifluoroacetate as described for compound 109. $R_t$=1.24 min (Method B). Detected mass: 397.2 (M+H$^+$).

6-[4-Aminomethyl-4-(3,4-dichloro-phenyl)-cyclohexyloxy]-7-chloro-2H-isoquinolin-1-one (116)

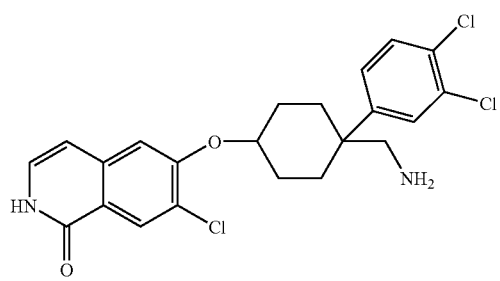 [SMILES: NCC1(c2ccc(Cl)c(Cl)c2)CCC(Oc2cc3cc[nH]c(=O)c3cc2Cl)CC1]

Starting from 7-chloro-6-fluoro-2-(4-methoxy-benzyl)-2H-isoquinolin-1-one (10) and 4-aminomethyl-4-(3,4-dichloro-phenyl)-cyclohexanol, 6-[4-aminomethyl-4-(3,4-dichloro-phenyl)-cyclohexyloxy]-7-chloro-2H-isoquinolin-1-one (116) could be obtained as the trifluoroacetate as described for compound 109. $R_t$=1.35 min (Method B). Detected mass: 451.1 (M+H$^+$).

7-Bromo-6-fluoro-isoquinoline (117)

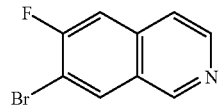

Starting from 3-bromo-4-fluoro-benzaldehyde, the title compound was prepared by the same reaction sequence as used for the synthesis of 6-fluoro-isoquinoline (3). $R_t$=0.91 min (Method B). Detected mass: 226.0 (M+H$^+$).

C-[4-(7-Chloro-isoquinolin-6-yloxy)-1-phenyl-cyclohexyl]-methylamine (120)

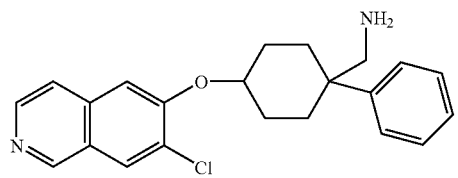 [SMILES: NCC1(c2ccccc2)CCC(Oc2cc3ccncc3cc2Cl)CC1]

123.3 mg of 4-aminomethyl-4-phenyl)-cyclohexanol were dissolved in 4 mL of dry DMF and 60 mg of sodium hydride were added. The mixture was allowed to stir for 20 minutes, then 91 mg of 7-Chloro-6-fluoro-isoquinoline (4) were added. Stirring at room temperature was continued until conversion was complete. Ethyl acetate and saturated sodium chloride solution were added. The phases were separated and the aqueous phase was extracted with ethyl acetate. The combined organic phases were dried over sodium sulfate, concentrated and the resultant residue was purified via preparative HPLC. The obtained TFA salt was dissolved in 2 N HCl and evaporated. After dissolving the residue in water and lyophilization, the title compound was isolated as the hydrochloride. $R_t$=0.97 min (Method B). Detected mass: 367.2 (M+H$^+$).

Methyl (3-endo)-9-oxobicyclo[3.3.1]nonane-3-carboxylate (121)

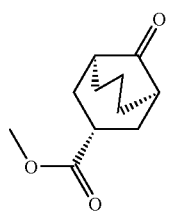

Following a published procedure (Tetrahedron 1974, 633-640) commercial 3-bromo-2-bromomethyl-propionic acid methyl ester (24.5 g, 94.21 mmol) was added dropwise to a stirred solution of 1-cyclohex-1-enyl-pyrrolidine (15.96 mL, 99.17 mmol) and triethylamine (13.13 mL, 94.21 mmol) in dry acetonitrile (180 mL). After the addition, the mixture was heated at 90° C. and stirred for 2 hours before aqueous 5% acetic acid (10 mL) was added and heating was continued for another 1 hour. The solvent was evaporated and the residue was partitioned between ether and water. The organic phase was washed with saturated NaHCO$_3$ solution and brine. It was then dried over sodium sulfate, filtered and evaporated to afford crude methyl (3-endo)-9-oxobicyclo[3.3.1]nonane-3-carboxylate (17.7 g) which was used without any further purification.

Benzyl [(3-endo)-9-oxobicyclo[3.3.1]non-3-yl]carbamate (122)

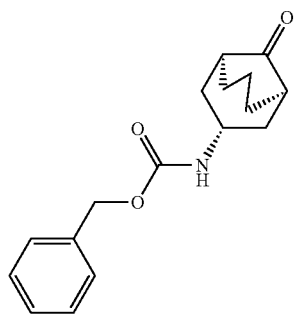 [SMILES: O=C(N[C@H]1C[C@H]2CCC[C@@H](C1)C2=O)OCc1ccccc1]

A stirred solution of crude methyl (3-endo)-9-oxobicyclo[3.3.1]nonane-3-carboxylate (121, 5 g, 25.48 mmol) in absolute ethanol (150 mL) was treated with aqueous 1N NaOH (127 mL) and the mixture was heated at 50° C. for 1 hour. Ethanol was evaporated and the mixture was acidified by adding slowly aqueous 1N HCl. The resulting aqueous phase was extracted with diethyl ether. The organic phase was dried over sodium sulfate, filtered and evaporated to yield crude (3-endo)-9-oxobicyclo[3.3.1]nonane-3-carboxylic acid (4.45 g) which was used without any further purification.

Crude (3-endo)-9-oxobicyclo[3.3.1]nonane-3-carboxylic acid (3 g, 16.46 mmol) was suspended in dry toluene (30 mL) followed by subsequent addition of diphenylphosphoryl azide (3.9 mL, 18.11 mmol) and triethylamine (2.52 mL, 18.11 mmol). The mixture was kept at room temperature for 2 hours, then slowly heated to 110° C. and stirred at this temperature for 2 hours. The isocyanate solution was slightly cooled and treated with anhydrous benzyl alcohol (17.04 mL, 0.164 mol). The resulting solution was heated at 110° C. overnight, cooled and washed successively with water and brine. The organic phase was dried over sodium sulfate, filtered and concentrated in vacuo. The oily residue was purified by chromatography on silica gel to afford the title compound (3.36 g). $R_f$=4.61 min (Method L). Detected mass: 288 (M+H$^+$).

Benzyl [(3-endo)-9-hydroxybicyclo[3.3.1]non-3-yl]carbamate (123)

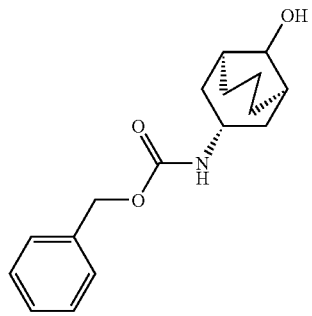 [SMILES: O=C(N[C@H]1C[C@H]2CCC[C@@H](C1)C2O)OCc1ccccc1]

To a stirred suspension of benzyl [(3-endo)-9-oxobicyclo[3.3.1]non-3-yl]carbamate (122, 0.7 g, 2.44 mmol) in absolute ethanol (25 mL) was added sodium borohydride (138 mg, 3.65 mmol). The resulting mixture was stirred at room temperature for 1 hour, then poured onto ice and stirred for 0.5 hour. Ethanol was evaporated under reduced pressure and the resulting aqueous layer was extracted with dichloromethane. The organic layer was dried over anhydrous sodium sulfate, filtered and concentrated under reduced pressure. The crude benzyl [(3-endo)-9-hydroxybicyclo[3.3.1]non-3-yl]carbamate (123, 0.7 g) was obtained as a syn/anti mixture and used in the next step without any further purification. $R_f$=4.53 min, 4.67 min (Method L). Detected mass: 290 (M+H$^+$).

(3-Endo)-3-aminobicyclo[3.3.1]nonan-9-ol (124)

Hydrogenolysis of benzyl [(3-endo)-9-hydroxybicyclo[3.3.1]non-3-yl]carbamate (123, 0.84 g, 2.90 mmol) was carried out in methanol (30 mL) containing 20% Pd(OH)$_2$ (163 mg, 1.16 mmol) at room temperature. The resulting suspension was stirred 1 hour under an H$_2$ atmosphere (1 bar), filtered and concentrated in vacuo to dryness to afford (3-endo)-3-aminobicyclo[3.3.1]nonan-9-ol (124, 0.45 g) as a syn/anti mixture. The obtained crude material was used in the next step without any further purification. Detected mass: 155 (m/z, EI).

(3-Endo)-9-{[1-(benzyloxy)-7-chloroisoquinolin-6-yl]oxy}bicyclo[3.3.1]nonan-3-amine (125)

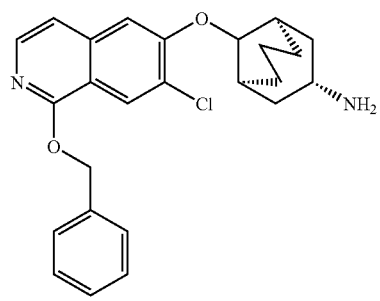 [SMILES: N[C@H]1C[C@H]2CCC[C@@H](C1)C2Oc1cc2ccnc(OCc3ccccc3)c2cc1Cl]

To a solution of (3-endo)-3-aminobicyclo[3.3.1]nonan-9-ol (124, 0.148 g, 0.96 mmol) in anhydrous N,N-dimethylacetamide (8 ml) at 0° C. was added 60% sodium hydride (0.104 g, 2.61 mmol) in portions. The reaction mixture was stirred for 10 min at room temperature, 1-(benzyloxy)-7-chloro-6-fluoroisoquinoline (11, 0.250 g, 0.87 mmol) was then added and stirring was continued overnight. The suspension was poured onto ice and the resulting aqueous phase was extracted with dichloromethane. The organic phase was dried over sodium sulfate, filtered and evaporated in vacuo. The crude product (2.18 g) was purified by chromatography on silica gel (eluting with 0 to 5% methanol in dichloromethane with 1% aq. ammonia) to yield (3-endo)-9-{[1-(benzyloxy)-7-chloroisoquinolin-6-yl]oxy}bicyclo[3.3.1]nonan-3-amine (125, 0.26 g) as a syn/anti mixture. $R_t$=5.82 min, 6.02 min (Method L). Detected mass: 423 (M+H$^+$).

6-{[(3-Endo)-3-aminobicyclo[3.3.1]non-9-yl]oxy}-7-chloroisoquinolin-1(2H)-one (126)

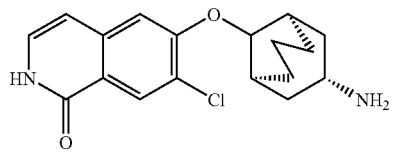 [SMILES: N[C@H]1C[C@H]2CCC[C@@H](C1)C2Oc1cc2cc[nH]c(=O)c2cc1Cl]

(3-endo)-9-{[1-(benzyloxy)-7-chloroisoquinolin-6-yl]oxy}bicyclo[3.3.1]nonan-3-amine (125, 0.26 g, 0.61 mmol) was suspended in 2-propanol (5 mL) and 1N HCl in diethyl ether (3.1 mL) was added. The resulting mixture was stirred at room temperature for 3 days, then concentrated in vacuo to dryness. The obtained solid was triturated in methanol and diethyl ether, filtered, rinsed with ether and dried in vacuo to afford the title compound (0.217 g) as a syn/anti mixture as the hydrochloride. $R_t$=6.29 min, 7.04 min (Method M). Detected mass: 333 (M+H$^+$).

Methyl (3-exo)-9-oxobicyclo[3.3.1]nonane-3-carboxylate (127)

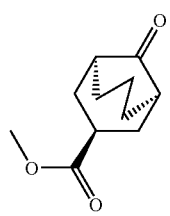

Following a slightly modified published procedure (Organic Letters 2006, 3963-3966), Amberlyst 15 (0.1 g) was added to a solution of methyl (3-endo)-9-oxobicyclo[3.3.1]nonane-3-carboxylate (3 g, 15.29 mmol) and trimethyl orthoformate (5.02 mL, 45.86 mmol) in dry methanol (15 mL). The mixture was heated at 80° C. for 1 hour, it was then filtered through a pad of silica and washed with diethyl ether. The resulting crude methyl (3-endo)-9,9-dimethoxybicyclo[3.3.1]nonane-3-carboxylate (15.29 mmol) was added to a solution of 0.5M sodium methoxide in methanol (46.43 mL, 23.21 mmol) at room temperature. The resulting mixture was heated to reflux for 12 hours before it was cooled to room temperature. The solvent was evaporated in vacuo and the residue was partitioned between ethyl acetate and 0.5N HCl. The organic layer was separated, then dried over sodium sulfate, filtered and concentrated under reduced pressure to afford the title compound 127 which was used without any further purification.

Benzyl [(3-exo)-9-oxobicyclo[3.3.1]non-3-yl]carbamate (128)

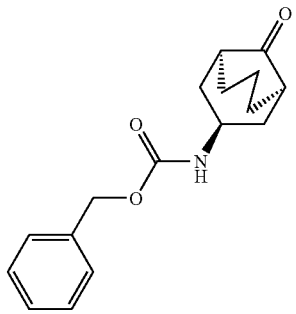 [SMILES: O=C(N[C@@H]1C[C@H]2CCC[C@@H](C1)C2=O)OCc1ccccc1]

Starting from methyl (3-exo)-9-oxobicyclo[3.3.1]nonane-3-carboxylate (127), the title compound was prepared following the reaction sequence described for the synthesis of benzyl [(3-exo)-9-oxobicyclo[3.3.1]non-3-yl]carbamate (122). $R_t$=7.75 min (Method K). Detected mass: 288 (M+H$^+$).

Benzyl [(3-exo)-9-hydroxybicyclo[3.3.1]non-3-yl]carbamate (129)

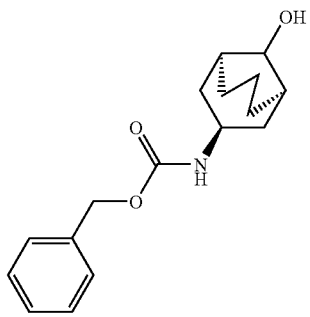 [SMILES: O=C(N[C@@H]1C[C@H]2CCC[C@@H](C1)C2O)OCc1ccccc1]

Benzyl [(3-exo)-9-oxobicyclo[3.3.1]non-3-yl]carbamate (128) was reduced as described for benzyl [(3-endo)-9-oxobicyclo[3.3.1]non-3-yl]carbamate (123). The title compound was obtained as a syn/anti mixture. $R_t$=7.47 min, 7.80 min (Method K). Detected mass: 290 (M+H$^+$).

(3-Exo)-3-aminobicyclo[3.3.1]nonan-9-ol (130)

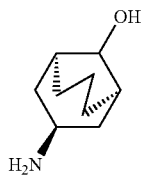

Benzyl [(3-exo)-9-hydroxybicyclo[3.3.1]non-3-yl]carbamate (129) was submitted to hydrogenolysis as described for benzyl [(3-endo)-9-hydroxybicyclo[3.3.1]non-3-yl]carbamate (124). The title compound was obtained as a syn/anti mixture. Detected mass: 155 (m/z, EI).

6-{[(3-Exo)-3-aminobicyclo[3.3.1]non-9-yl]oxy}-7-chloroisoquinolin-1(2H)-one (131)

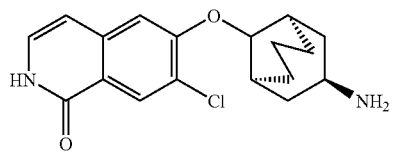 [SMILES: N[C@@H]1C[C@H]2CCC[C@@H](C1)C2Oc1cc2cc[nH]c(=O)c2cc1Cl]

Starting from (3-exo)-3-aminobicyclo[3.3.1]nonan-9-ol (130) and 1-(benzyloxy)-7-chloro-6-fluoroisoquinoline (11), the title compound was obtained as a syn/anti mixture as the hydrochloride following the procedures described for 6-{[(3-endo)-3-aminobicyclo[3.3.1]non-9-yl]oxy}-7-chloroisoquinolin-1(2H)-one (126). $R_t$=5.57 min, 5.85 min (Method K). Detected mass: 333 (M+H$^+$)

(3-Endo)-3-aminobicyclo[3.2.1]octan-8-ol (132)

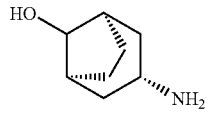

Starting from methyl (3-endo)-8-oxobicyclo[3.2.1]octane-3-carboxylate (preparation described in EP0130882), the title compound was prepared as hydrochloride following the reaction sequence described for (3-endo)-3-aminobicyclo[3.3.1]nonan-9-ol (124).

6-{[(3-Endo,8-syn)-3-aminobicyclo[3.2.1]oct-8-yl]oxy}-7-chloroisoquinolin-1(2H)-one (133) and 6-{[(3-endo,8-anti)-3-aminobicyclo[3.2.1]oct-8-yl]oxy}-7-chloroisoquinolin-1(2H)-one (134)

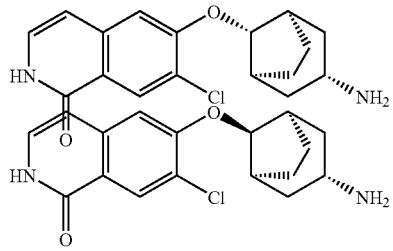

Starting from (3-endo)-3-aminobicyclo[3.2.1]octan-8-ol (132) and 1-(benzyloxy)-7-chloro-6-fluoroisoquinoline (11), the title compounds were prepared as the hydrochlorides, following the reaction sequence described for compound 126. $R_t$=0.62 min, 0.63 min (Method N). Detected mass: 319 (M+H$^+$).

LC/MS-Methods:

| Method A: | |
|---|---|
| Stationary phase: | Col YMC Jsphere 33 × 2 |
| Gradient: | ACN + 0.05% TFA:H$_2$O + 0.05% TFA |
| | 5:95(0 min) to 95:5(3.4 min) to 95:5(4.4 min) |
| Flow | 1 mL/min |

| Method B: | |
|---|---|
| Stationary phase: | Col YMC Jsphere 33 × 2 |
| Gradient: | ACN + 0.05% TFA:H$_2$O + 0.05% TFA |
| | 5:95(0 min) to 95:5(2.5 min) to 95:5(3.0 min) |
| Flow: | 1 mL/min |

| Method C: | |
|---|---|
| Stationary phase: | Col YMC Jsphere ODS H80 20 × 2 |
| Gradient: | ACN:H$_2$O + 0.05% TFA |
| | 4:96(0 min) to 95:5(2.0 min) to 95:5(2.4 min) |
| Flow | 1 mL/min |

| Method D: | |
|---|---|
| Stationary phase: | Col YMC Jsphere 33 × 2.1 |
| Gradient: | ACN + 0.08% FA:H$_2$O + 0.1% FA (Formic acid) |
| | 5:95 (0 min) to 95:5 (2.5 min) to 95:5 (3 min) |
| Flow | 1.3 mL/min |

| Method E: | |
|---|---|
| Stationary phase: | Col YMC Jsphere 33 × 2 |
| Gradient: | ACN + 0.05% TFA:H$_2$O + 0.05% TFA |
| | 5:95(0 min) to 5:95(0.5 min) to 95:5(3.5 min) to 95:5(4 min) |
| Flow | 1.3 mL/min |

| Method F: | |
|---|---|
| Stationary phase: | Col YMC Jsphere 33 × 2.1 |
| Gradient: | ACN + 0.05% TFA:H$_2$O + 0.05% TFA |
| | 2:98(0 min) to 2:98(1 min) to 95:5(5 min) to 95:5(6.25 min) |
| Flow | 1 mL/min |

| Method G: | |
|---|---|
| Stationary phase: | Col YMC Jsphere ODS H80 20 × 2 |
| Gradient: | ACN:H$_2$O + 0.05% TFA |
| | 7:93(0 min) to 95:5(1.2 min) to 95:5(1.4 min) |
| Flow | 1.1 mL/min |

| Method H: | |
|---|---|
| Stationary phase: | Waters XBridged C18 |
| Gradient: | ACN + 0.05% TFA:H$_2$O + 0.05% TFA |
| | 5:95(0 min) to 5:95(0.3 min) to 95:5(3.5 min) to 95:5 (4 min) |
| Flow | 1.3 mL/min |

| Method I: | |
|---|---|
| Stationary phase: | Col YMC Jsphere ODS H80 20 × 2 |
| Gradient: | ACN:H$_2$O + 0.05% TFA |
| | 20:80(0 min) to 98:2(1.6 min) to 98:2(2.4 min) |
| Flow | 1 mL/min |

| Method J: | |
|---|---|
| Stationary phase: | Waters XBridge C18 4 |
| Gradient: | H$_2$O + 0.1% FA:ACN + 0.08% FA |
| | 97:3(0 min) to 40:60(3.5 min) to 2:98(5 min) |
| Flow | 1.3 mL/min |

| Method K | |
|---|---|
| Stationary phase: | Column Kromasil C18, 50 × 2.1 mm, 3.5 μm |
| Gradient: | H$_2$O/ACN/TFA (1000/30/0.5):ACN/TFA (1000/0.5) |
| | 100:0(0 min) to 0:100(12 min) to 0:100(15 min) |
| Flow: | 0.5 mL/min |

| Method L | |
|---|---|
| Stationary phase: | Column Gemini C18, 30 × 4.6 mm, 3 μm |
| Gradient: | H$_2$O + 0.1% FA:ACN + 0.1% FA |
| | 95:5(0 min) to 0:100(5.5 min) to 0:100(7.5 min) |
| Flow: | 1 mL/min |

| Method M | |
|---|---|
| Stationary phase: | Column Gemini C18, 30 × 4.6 mm, 3 μm |
| Gradient: | H$_2$O + 0.1% FA:ACN + 0.1% FA |
| | 95:5(0 min) to 95:5(1 min) to 0:100(9 min) to 0:100(12 min) |
| Flow: | 1 mL/min |

| Method N | |
|---|---|
| Stationary phase: | Column Acquity BEH C18, 50 × 2.1 mm, 1.7 μm |
| Gradient: | H$_2$O + 0.05% TFA:ACN + 0.035% TFA<br>98:2(0 min) to 0:100(1.6 min) to 0:100(2.1 min) to<br>98:2(3 min) |
| Flow: | 1 mL/min |

Determination of Rho Kinase Inhibition

To measure Rho-kinase inhibition, IC$_{50}$ values were determined according to the following protocol:

Active human recombinant ROCK II (N-terminal His6-tagged recombinant human ROCK-II residues 11-552) was purchased from Upstate Ltd., Dundee, UK. The peptide substrate, Fluorescein-AKRRRLSSLRA-COOH, was obtained from JPT Peptide Technologies, Berlin, Germany. Adenosine-5'-triphosphate (ATP), bovine serum albumine (BSA), dimethylsulphoxide (DMSO), 4-(2-Hydroxyethyl)piperazine-1-ethanesulfonic acid (Hepes), Brij-35 and dithiothreitol (DTT) were purchased from Sigma-Aldrich, Munich, Germany. Tris(hydroxymethyl)-aminomethane (Tris), magnesium chloride, NaOH, 1M HCl and EDTA were obtained from Merck Biosciences, Darmstadt, Germany. "Complete" protease inhibitor was from Roche Diagnostics, Mannheim, Germany.

Test compounds were diluted to the appropriate concentrations in buffer 1 (25 mM Tris-HCl, pH 7.4, 5 mM MgCl$_2$, 2 mM DTT, 0.02% (w/v) BSA and 3% DMSO). The ROCK II enzyme was diluted to a concentration of 100 ng/ml in buffer 2 (25 mM Tris-HCl, pH 7.4, 5 mM MgCl$_2$, 2 mM DTT and 0.02% (w/v) BSA). The peptide substrate and ATP were diluted to concentrations of 3 μM and 120 μM, respectively, in the buffer 2. Two μl of the compound solution were mixed with 2 μl of the diluted enzyme in a 384-well small volume microtiter plate (Greiner, Bio-One, Frickenhausen, Germany), and the kinase reaction was initiated by addition of 2 μl of the solution containing peptide substrate and ATP. After 60 min incubation at 32° C., the reaction was stopped by addition of 20 μl of a solution containing 100 mM Hepes-NaOH, pH 7.4, 0.015% (v/v) Brij-35, 45 mM EDTA and 0.227% chip coating reagent 1 (Caliper Lifescience Inc, Hopkinton, Mass.). Phosphorylation of the substrate peptide was then detected on a Caliper 3000 instrument essentially as described by Pommereau et al (J. Biomol. Screening 9 (5), 409-416, 2004). Separation conditions were as follows: Pressure—1.3 psi, upstream voltage—1562 V, downstream voltage—500 V, sample sip time 200 ms. Positive controls (buffer 1 instead of compound) and negative controls (buffer 1 instead of compound and buffer 2 instead of ROCK II) were run in parallel on each plate.

The following products/compounds were tested in said assay by using the respective form (salt or free base) obtained as in the examples described above and the following activities were measured.

| Compound No. | pIC50 |
|---|---|
| 20 | +++++ |
| 41 | +++++ |
| 57 | +++++ |
| 107 | +++++ |
| 108 | +++++ |
| 109 | +++++ |
| 110 | +++++ |
| 111 | ++++ |
| 112 | +++++ |
| 113 | +++++ |
| 114 | +++++ |
| 116 | +++++ |
| 118 | +++++ |
| 119 | ++++ |
| 120 | +++++ |

The given activity is denoted as the negative decadal logarithm of the IC$_{50}$ (pIC$_{50}$) as follows:

| | |
|---|---|
| +: | pIC50 ≤ 3.0 |
| ++: | 3.0 ≤ pIC$_{50}$ < 4.0 |
| +++ | 4.0 ≤ pIC$_{50}$ < 5.0 |
| ++++: | 5.0 ≤ pIC$_{50}$ < 6.0 |
| +++++: | 6.0 ≤ pIC$_{50}$ |

The invention claimed is:
1. A compound of the formula (I)

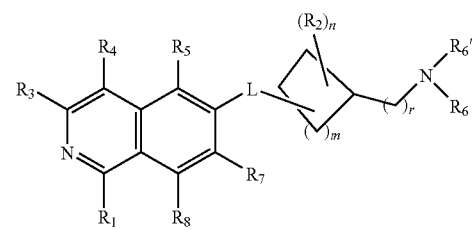

wherein
R$_1$ is H, OH or NH$_2$;
R$_2$ is
(C$_3$-C$_8$)cycloalkyl,
(C$_6$-C$_{10}$)aryl,
(C$_7$-C$_8$)alkyl,
(C$_1$-C$_6$)alkylene-(C$_6$-C$_{10}$)aryl,
(C$_2$-C$_6$)alkenyl,
(C$_2$-C$_6$)alkynyl,
(C$_1$-C$_6$)alkylene-C(O)NH$_2$,
(C$_1$-C$_6$)alkylene-C(O)NH—(C$_1$-C$_6$)alkyl,
(C$_1$-C$_6$)alkylene-C(O)N[(C$_1$-C$_6$)alkyl]$_2$,
(C$_1$-C$_6$)alkylene-C(O)O—(C$_1$-C$_6$)alkyl,
C(O)O—(C$_1$-C$_6$)alkyl,
C(O)(C$_1$-C$_6$)alkyl,
C(O)—NH—(C$_2$-C$_6$)alkenyl,
C(O)—NH—(C$_2$-C$_6$)alkynyl,
C(O)NH—(C$_1$-C$_6$)alkyl or
C(O)N[(C$_1$-C$_6$)alkyl]$_2$; or
R$_2$ is (C$_1$-C$_6$)alkyl, provided that in said alkyl residue at least one hydrogen is substituted by OH, OCH$_3$, COOH, COOCH$_3$, NH$_2$, NHCH$_3$, N(CH$_3$)$_2$, CONH$_2$, CONHCH$_3$ or CON(CH$_3$)$_2$;
R$_3$ is
H,
halogen,
(C$_1$-C$_6$)alkyl,
OH,
O—R",
NH$_2$,
NHR", NR"R" or
NH—C(O)—R",
$R_4$ is
H,
halogen,
hydroxy,
CN,
$(C_1-C_6)$alkyl,
$R_5$ is
H,
halogen,
CN,
$NO_2$,
$(C_1-C_6)$alkyl,
$(C_2-C_6)$alkenyl,
CH(OH)—$(C_1-C_6)$alkyl,
$NH_2$,
NH—$SO_2$H,
NH—$SO_2$—$(C_1-C_6)$alkyl,
NH—C(O)—$(C_1-C_6)$alkyl,
C(O)N[$(C_1-C_6)$alkyl]$_2$,
C(O)OH, or
C(O)O—$(C_1-C_6)$alkyl;
$R_6$ and $R_6'$ are independently of each other
H,
$(C_1-C_8)$alkyl,
$(C_1-C_6)$alkylene-O—$(C_1-C_6)$alkyl,
$(C_1-C_6)$alkylene-C(O)$NH_2$,
$(C_1-C_6)$alkylene-C(O)NH—$(C_1-C_6)$alkyl,
$(C_1-C_6)$alkylene-C(O)N[$(C_1-C_6)$alkyl]$_2$,
$(C_1-C_6)$alkylene-C(O)O—$(C_1-C_6)$alkyl,
C(O)O—$(C_1-C_6)$alkyl,
C(O)$(C_1-C_6)$alkyl,
C(O)NH—$(C_1-C_6)$alkyl,
C(O)N[$(C_1-C_6)$alkyl]$_2$,
or
$R_6$ and $R_6'$, together with the N-atom to which they are attached, form a $(C_5-C_{10})$ heterocyclyl group;
$R_7$ is
H,
halogen,
CN,
$NO_2$,
$(C_1-C_6)$alkyl,
O—$(C_1-C_6)$alkyl,
$(C_2-C_6)$alkenyl,
CH(OH)—$(C_1-C_6)$alkyl,
$NH_2$,
NH—$SO_2$H,
NH—$SO_2$—$(C_1-C_6)$alkyl,
$SO_2$—$NH_2$,
NH—C(O)—$(C_1-C_6)$alkyl,
C(O)N[$(C_1-C_6)$alkyl]$_2$,
C(O)OH, or
C(O)O—$(C_1-C_6)$alkyl;
$R_8$ is H, halogen or $(C_1-C_6)$alkyl;
n is 1;
m is 3;
r is 0, 1 or 2 and
L is O—$(CH_2)p$;
p 0, 1, 2, 3 or 4;
R' is
$(C_3-C_8)$cycloalkyl,
$(C_5-C_{10})$heterocyclyl,
$(C_6-C_{10})$aryl; and
R" is
$(C_1-C_6)$alkyl, $(C_1-C_6)$alkylene-O—$(C_1-C_6)$alkyl,
or
$(C_1-C_6)$alkylene-$NR_xR_y$; and
$R_x$ and $R_y$ are independently of each other
$(C_1-C_6)$alkyl,
$(C_1-C_4)$alkylene-NH$(C_1-C_6)$alkyl or
$(C_1-C_4)$alkylene-N[$(C_1-C_6)$alkyl]$_2$,
wherein in residues $R_2$, $R_4$, $R_5$, $R_6$, $R_6'$, $R_7$ and $R_8$ as alkyl, alkylene or cycloalkyl can optionally be substituted one or more times by OH, $OCH_3$, COOH, $COOCH_3$, $NH_2$, $NHCH_3$, $N(CH_3)_2$, $CONH_2$, $CONHCH_3$ or $CON(CH_3)_2$;
wherein in residues $R_2$ to $R_8$ as alkyl or alkylene can optionally be substituted one or more times by halogen;
wherein in residue R2 as $(C_6-C_{10})$aryl are unsubstituted or substituted one or more times by a group independently selected from halogen, OH, $NO_2$, $N_3$, CN, C(O)—$(C_1-C_6)$alkyl, COOH, COO$(C_1-C_6)$alkyl, $CONH_2$, CONH$(C_1-C_6)$alkyl, CON[$(C_1-C_6)$alkyl]$_2$, $(C_1-C_6)$alkyl, $(C_1-C_6)$alkylene-OH, $(C_1-C_6)$alkylene-$NH_2$, $(C_1-C_6)$alkylene-NH$(C_1-C_6)$alkyl, $(C_1-C_6)$alkylene-N[$(C_1-C_6)$alkyl]$_2$, $(C_2-C_6)$alkenyl, $(C_2-C_6)$alkynyl, O—$(C_1-C_6)$alkyl, O—C(O)—$(C_1-C_6)$alkyl, $PO_3H_2$, $SO_3H$, $SO_2$—$NH_2$, $SO_2$NH$(C_1-C_6)$alkyl, $SO_2$N[$(C_1-C_6)$alkyl]$_2$, S—$(C_1-C_6)$alkyl; SO—$(C_1-C_6)$alkyl, $SO_2$—$(C_1-C_6)$alkyl, $SO_2$—N=CH—N[$(C_1-C_6)$alkyl]$_2$, C(NH)($NH_2$), $NH_2$, NH—$(C_1-C_6)$alkyl, N[$(C_1-C_6)$alkyl]$_2$, NH—C(O)—$(C_1-C_6)$alkyl, NH—C(O)O—$(C_1-C_6)$alkyl, NH—$SO_2$—$(C_1-C_6)$alkyl, N$(C_1-C_6)$alkyl-C(O)—$(C_1-C_6)$alkyl, N$(C_1-C_6)$alkyl-C(O)O—$(C_1-C_6)$alkyl, N$(C_1-C_6)$alkyl-C(O)—NH—$(C_1-C_6)$alkyl], or
stereoisomeric form thereof and/or tautomeric form thereof and/or pharmaceutically acceptable salt thereof.

2. The compound according to claim 1, having the formula (II)

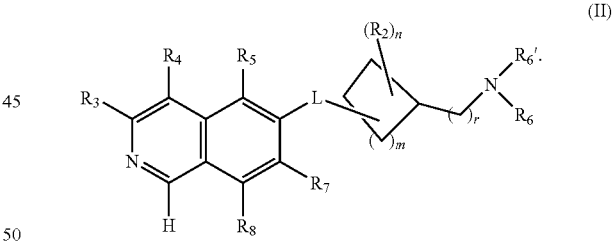

3. The compound according to claim 1, having the formula (III)

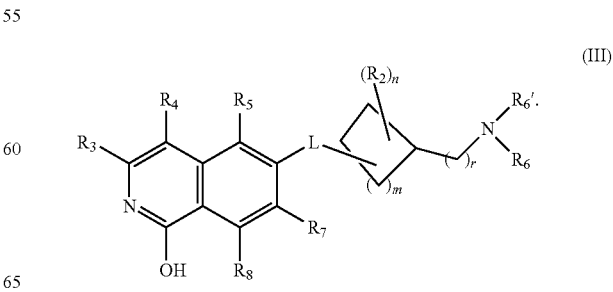

4. The compound according to claim 1, having the formula (III')

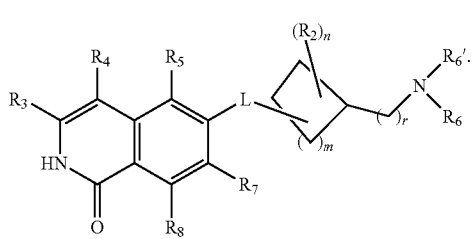

(III')

5. The compound according to claim 1, wherein $R_1$ is $NH_2$.
6. The compound according to claim 1, wherein $R_3$ is H, halogen, O—R" or NHR".
7. The compound according to claim 6, wherein $R_3$ is H or NHR".
8. The compound according to claim 7, wherein $R_3$ is H.
9. The compound according to claim 1, wherein $R_8$ is H, halogen or $(C_1-C_4)$alkyl.
10. The compound according to claim 9, wherein $R_8$ is H, Cl, F, methyl or ethyl.
11. The compound according to claim 10, wherein $R_8$ is H.
12. The compound according to claim 1, wherein $R_4$ is H, halogen or $(C_1-C_6)$alkyl.
13. The compound according to claim 12, wherein $R_4$ is H, halogen or $(C_1-C_4)$alkyl.
14. The compound according to claim 13, wherein $R_4$ is H.
15. The compound according to one of claim 1, wherein $R_5$ is H, halogen, CN, $(C_1-C_6)$alkyl, or $(C_2-C_6)$alkenyl.
16. The compound according to claim 15, wherein $R_5$ is H, halogen, $(C_1-C_6)$alkyl, or $(C_2-C_6)$alkenyl.
17. The compound according to claim 16, wherein $R_5$ is H, halogen, methyl, ethyl, or vinyl.
18. The compound according to claim 17, wherein $R_5$ is H, halogen, methyl, or ethyl.
19. The compound according to claim 18, wherein $R_5$ is H.
20. The compound according to claim 1, wherein $R_7$ is H, halogen, CN, $(C_1-C_6)$alkyl, O—$(C_1-C_6)$alkyl, or $(C_2-C_6)$alkenyl.
21. The compound according to claim 20, wherein $R_7$ is H, halogen, CN, $(C_1-C_4)$alkyl, O—$(C_1-C_4)$alkyl, or $(C_2-C_4)$alkenyl.
22. The compound according to claim 21, wherein $R_7$ is H, fluoro, chloro, bromo, methyl, ethyl, methoxy, nitrile, or vinyl.
23. The compound according to claim 22, wherein $R_7$ is H, fluoro, chloro, bromo, methyl or methoxy.
24. The compound according to claim 23, wherein $R_7$ is H.
25. The compound according to claim 1, wherein $R_2$ is
$(C_3-C_8)$cycloalkyl,
$(C_6-C_{10})$aryl,
$(C_7-C_8)$alkyl,
$(C_1-C_6)$alkylene-$(C_6-C_{10})$aryl,
$(C_2-C_6)$alkenyl,
$(C_1-C_6)$alkylene-C(O)$NH_2$,
$(C_1-C_6)$alkylene-C(O)NH—$(C_1-C_6)$alkyl,
$(C_1-C_6)$alkylene-C(O)N[$(C_1-C_6)$alkyl]$_2$,
$(C_1-C_6)$alkylene-C(O)O—$(C_1-C_6)$alkyl,
C(O)NH—$(C_1-C_6)$alkyl,
C(O)—NH—$(C_2-C_6)$alkenyl,
C(O)—NH—$(C_2-C_6)$alkynyl,
C(O)N[$(C_1-C_6)$alkyl]$_2$, $R_2$ is $(C_1-C_6)$alkyl, provided that in said alkyl residue at least one hydrogen is substituted by OH, $OCH_3$, COOH, $COOCH_3$, $NH_2$, $NHCH_3$, $N(CH_3)_2$, $CONH_2$, $CONHCH_3$ or $CON(CH_3)_2$.

26. The compound according to claim 25, wherein $R_2$ is
$(C_3-C_8)$cycloalkyl,
$(C_6-C_{10})$aryl,
$(C_1-C_6)$alkylene-$(C_6-C_{10})$aryl,
$(C_2-C_6)$alkenyl,
$(C_1-C_6)$alkylene-C(O)$NH_2$,
$(C_1-C_6)$alkylene-C(O)NH—$(C_1-C_6)$alkyl,
C(O)NH—$(C_1-C_6)$alkyl,
C(O)—NH—$(C_2-C_6)$alkynyl,
or
$R_2$ is $(C_1-C_3)$alkyl, provided that in said alkyl residue at least one hydrogen is substituted by OH, $OCH_3$, COOH, $COOCH_3$, $NH_2$, $NHCH_3$, $N(CH_3)_2$, $CONH_2$, $CONHCH_3$ or $CON(CH_3)_2$.

27. The compound according to claim 26, wherein $R_2$ is
$(C_3-C)$cycloalkyl,
$(C_6-C_{10})$aryl,
$(C_1-C_6)$alkylene-$(C_6-C_{10})$aryl,
$(C_2-C_6)$alkenyl,
$(C_1-C_6)$alkylene-C(O)NH—$(C_1-C_6)$alkyl,
C(O)NH—$(C_1-C_6)$alkyl,
C(O)—NH—$(C_2-C_6)$alkynyl.

28. The compound according to claim 1, wherein r is 0 or 1.
29. The compound according to claim 1, wherein
$R_6$ and $R_6'$ are independently of each other
H,
$(C_1-C_6)$alkyl,
$(C_1-C_6)$alkylene-O—$(C_1-C_6)$alkyl,
$(C_1-C_6)$alkylene-C(O)N[$(C_1-C_6)$alkyl]$_2$,
$(C_1-C_6)$alkylene-C(O)NH—$(C_1-C_6)$alkyl,
$(C_1-C_6)$alkylene-C(O)O—$(C_1-C_6)$alkyl,
C(O)O—$(C_1-C_6)$alkyl,
C(O)$(C_1-C_6)$alkyl,
C(O)NH—$(C_1-C_6)$alkyl,
C(O)N[$(C_1-C_6)$alkyl]$_2$,
or $R_6$ and $R_6'$, together with the N-atom to which they are attached, form a $(C_5-C_{10})$heterocyclyl group.

30. The compound according to claim 29, wherein $R_6$ and $R_6'$ are independently of each other
H,
$(C_1-C_6)$alkyl,
$(C_1-C_6)$alkylene-O—$(C_1-C_6)$alkyl,
$(C_1-C_6)$alkylene-C(O)N[$(C_1-C_6)$alkyl]$_2$,
$(C_1-C_6)$alkylene-C(O)NH—$(C_1-C_6)$alkyl,
$(C_1-C_6)$alkylene-C(O)O—$(C_1-C_6)$alkyl,
C(O)O—$(C_1-C_6)$alkyl,
C(O)$(C_1-C_6)$alkyl,
C(O)NH—$(C_1-C_6)$alkyl,
C(O)N[$(C_1-C_6)$alkyl]$_2$,
or $R_6$ and $R_6'$, together with the N-atom to which they are attached form a $(C_5-C_{10})$heterocyclyl group.

31. The compound according to claim 30, wherein
$R_6$ is H, $(C_1-C_6)$alkyl, and $R_6'$ is H,
$(C_1-C_6)$alkyl,
$(C_1-C_6)$alkylene-O—$(C_1-C_6)$alkyl,
$(C_1-C_6)$alkylene-C(O)NH—$(C_1-C_6)$alkyl,
$(C_1-C_6)$alkylene-C(O)N[$(C_1-C_6)$alkyl]$_2$,
$(C_1-C_6)$alkylene-C(O)O—$(C_1-C_6)$alkyl,
C(O)O—$(C_1-C_6)$alkyl,
C(O)$(C_1-C_6)$alkyl,
C(O)NH—$(C_1-C_6)$alkyl,
C(O)N[$(C_1-C_6)$alkyl]$_2$, $R_6$ and $R_6'$, together with the N-atom to which they are attached, form a $(C_5-C_{10})$heterocyclyl group.

32. The compound according to claim 31, wherein
$R_6$ is H or $(C_1-C_6)$alkyl and
$R_6'$ is H,
$(C_1-C_6)$alkyl,
$(C_1-C_4)$alkylene-O—$(C_1-C_4)$alkyl,
$(C_1-C_4)$alkylene-C(O)N[$(C_1-C_4)$alkyl]$_2$,
$(C_1-C_6)$alkylene-C(O)NH—$(C_1-C_6)$alkyl,
C(O)$(C_1-C_6)$alkyl,
or
$R_6$ and $R_6'$, together with the N-atom to which they are attached, form a $(C_5-C_{10})$heterocyclyl group.

33. The compound according to claim 32, wherein
$R_6$ is H or $(C_1-C_6)$alkyl and
$R_6'$ is
H,
$(C_1-C_6)$alkyl;
$(C_1-C_4)$alkylene-O—$(C_1-C_4)$alkyl;
$(C_1-C_4)$alkylene-C(O)N[$(C_1-C_4)$alkyl]$_2$;
C(O)$(C_1-C_4)$alkyl;
or $R_6$ and $R_6'$, together with the N-atom to which they are attached, form a $(C_5-C_6)$heterocyclyl group.

34. The compound according to claim 33, wherein $R_6$ is H or $(C_1-C_6)$alkyl and $R_6'$ is H or $(C_1-C_6)$alkyl.

35. The compound according to claim 34, wherein $R_6$ is H and $R_6'$ is H or $(C_1-C_6)$alkyl.

36. The compound according to claim 35, wherein $R_6$ and $R_6'$ are H.

37. The compound according to claim 1, wherein m is 3 and L is attached to the 3-position or to the 4-position of the amino cyclohexane ring.

38. The compound according to claim 1, wherein m is 3 and L is attached to the 4-position of the amino cyclohexane ring.

39. The compound according to claim 1, wherein p is 0.

40. The compound according to claim 1, wherein
$R_1$ is H or OH
$R_2$ is $(C_7-C_8)$alkyl, $(C_3-C_8)$cycloalkyl, $(C_6-C_{10})$aryl, $(C_1-C_6)$alkylene-$(C_6-C_{10})$aryl, $(C_2-C_6)$alkenyl, $(C_1-C_6)$alkylene-C(O)NH$_2$, $(C_1-C_6)$alkylene-C(O)NH—$(C_1-C_6)$alkyl, $(C_1-C_6)$alkylene-C(O)N[$(C_1-C_6)$alkyl]$_2$, $(C_1-C_6)$alkylene-C(O)O—$(C_1-C_6)$alkyl, C(O)NH—$(C_1-C_6)$alkyl, C(O)—NH—$(C_2-C_6)$alkenyl, C(O)—NH—$(C_2-C_6)$alkynyl, C(O)N[$(C_1-C_6)$alkyl]$_2$; or
$R_2$ is $(C_1-C_6)$alkyl, provided that in said alkyl residue at least one hydrogen is substituted by OH, OCH$_3$, COOH, COOCH$_3$, NH$_2$, NHCH$_3$, N(CH$_3$)$_2$, CONH$_2$, CONHCH$_3$ or CON(CH$_3$)$_2$;
$R_3$ is H, halogen, O—R" or NHR";
$R_4$ is H, halogen or $(C_1-C_6)$alkyl;
$R_5$ is H, $(C_1-C_6)$alkyl, halogen, CN, or $(C_2-C_6)$alkenyl;
$R_6$ and $R_6'$ are independently of each other H, $(C_1-C_8)$alkyl, $(C_1-C_6)$alkylene-O—$(C_1-C_6)$alkyl, $(C_1-C_6)$alkylene—C(O)NH$_2$, $(C_1-C_6)$alkylene-C(O)N[$(C_1-C_4)$alkyl]$_2$, C(O)O—$(C_1-C_6)$alkyl, C(O)$(C_1-C_6)$alkyl, C(O)NH—$(C_1-C_6)$alkyl, C(O)N[$(C_1-C_6)$alkyl]$_2$,
or $R_6$ and $R_6'$, together with the N-atom to which they are attached, form a $(C_5-C_6)$heterocyclyl group;
$R_7$ is H, halogen, CN, $(C_1-C_6)$alkyl, O—$(C_1-C_6)$alkyl, or $(C_2-C_6)$alkenyl;
m is 3,
n is 1,
r is 0, 1 or 2
L is O—$(CH_2)$p; and
p is 0, 1 or 2.

41. The compound according to claim 1, wherein
$R_1$ is H or OH;
$R_2$ is, $(C_3-C_8)$cycloalkyl, $(C_6-C_{10})$aryl, $(C_1-C_6)$alkylene-$(C_6-C_{10})$aryl, $(C_2-C_6)$alkenyl, $(C_1-C_6)$alkylene-C(O)NH$_2$, $(C_1-C_6)$alkylene-C(O)NH—$(C_1-C_6)$alkyl, C(O)NH—$(C_1-C_6)$alkyl, C(O)—NH—$(C_2-C_6)$alkynyl, or
$R_2$ is $(C_1-C_3)$alkyl, provided that in said alkyl residue at least one hydrogen is substituted by OH, OCH$_3$, COOH, COOCH$_3$, NH$_2$, NHCH$_3$, N(CH$_3$)$_2$, CONH$_2$, CONHCH$_3$ or CON(CH$_3$)$_2$;
$R_3$ is H, halogen or NHR";
$R_4$ is H, halogen or $(C_1-C_4)$alkyl;
$R_5$ is H, $(C_1-C_6)$alkyl, halogen, or $(C_2-C_4)$alkenyl;
$R_6$ and $R_6'$ are independently of each other H, $(C_1-C_8)$alkyl, $(C_1-C_6)$alkylene-O—$(C_1-C_6)$alkyl, C(O)$(C_1-C_6)$alkyl;
$R_7$ is H, halogen, CN, $(C_1-C_6)$alkyl, O—$(C_1-C_6)$alkyl, or $(C_2-C_6)$alkenyl;
m is 3;
n is 1;
r is 0 or 1;
L is O—$(CH_2)$p; and
p is 0 or 1.

42. The compound according to claim 1, wherein
$R_1$ is H or OH;
$R_2$ is $C_3-C_8$)cycloalkyl, $(C_6-C_{10})$aryl, $(C_1-C_6)$alkylene-$(C_6-C_{10})$aryl, $(C_2-C_6)$alkenyl, $(C_1-C_6)$alkylene-C(O)NH—$(C_1-C_6)$alkyl, C(O)NH—$(C_1-C_6)$alkyl or C(O)—NH—$(C_2-C_6)$alkynyl;
$R_3$ is H;
$R_4$ is H, halogen or $(C_1-C_4)$alkyl;
$R_5$ is H, $(C_1-C_4)$alkyl, halogen, or $(C_2-C_4)$alkenyl;
$R_6$ is H or $(C_1-C_4)$alkyl;
$R_6'$ is H, $(C_1-C_8)$alkyl, C(O)O—$(C_1-C_6)$alkyl, C(O)$(C_1-C_6)$alkyl;
$R_7$ is H, halogen, CN, $(C_1-C_4)$alkyl, O—$(C_1-C_4)$alkyl, or $(C_2-C_4)$alkenyl;
$R_8$ is H, halogen or $(C_1-C_4)$alkyl;
m is 3
n is 1;
r is 0 or 1 and
L is 0; or
stereoisomeric form thereof and/or tautomeric form thereof and/or pharmaceutically acceptable salt thereof.

43. A compound selected from the group consisting of
6-(4-Allyl-4-amino-cyclohexyloxy)-7-chloro-2H-isoquinolin-1-one,
6-(4-Allyl-4-amino-cyclohexyloxy)-2H-isoquinolin-1-one,
6-(4-amino-4-benzyl-cyclohexyloxy)-7-chloro-2H-isoquinolin-1-one,
6-(4-Amino-4-phenyl-cyclohexyloxy)-7-chloro-2H-isoquinolin-1-one,
6-(4-Aminomethyl-4-phenyl-cyclohexyloxy)-7-chloro-2H-isoquinolin-1-one,
6-[4-Aminomethyl-4-(4-chloro-phenyl)-cyclohexyloxy]-7-chloro-2H-isoquinolin-1-one,
6-[4-Aminomethyl-4-(3-chloro-phenyl)-cyclohexyloxy]-7-chloro-2H-isoquinolin-1-one,
6-[4-Aminomethyl-4-(3-methyl-phenyl)-cyclohexyloxy]-7-chloro-2H-isoquinolin-1-one,
6-[4-Aminomethyl-4-(3,4-dimethoxy-phenyl)-cyclohexyloxy]-7-chloro-2H-isoquinolin-1-one,
6-[4-Aminomethyl-4-(4-fluoro-phenyl)-cyclohexyloxy]-7-chloro-2H-isoquinolin-1-one,
6-[4-Aminomethyl-4-(4-methoxy-phenyl)-cyclohexyloxy]-7-chloro-2H-isoquinolin-1-one, 6-[4-Aminomethyl-4-(4-methyl-phenyl)-cyclohexyloxy]-7-chloro-2H-isoquinolin-1-one,
6-[4-Aminomethyl-4-(3,4-chloro-phenyl)-cyclohexyloxy]-7-chloro-2H-isoquinolin-1-one, and
C—[4-(7-Chloro-isoquinolin-6-yloxy)-1-phenyl-cyclohexyl]-methylamine), and
stereoisomeric form thereof and/or tautomeric form thereof and/or pharmaceutically acceptable salt thereof.

44. A compound selected from the group consisting of
6-(4-Allyl-4-amino-cyclohexyloxy)-4,7-dimethyl-2H-isoquinolin-1-one,
6-(cis-4-Allyl-4-amino-cyclohexyloxy)-7-methyl-2H-isoquinolin-1-one,
6-(cis-4-Amino-4-cyclopropyl-cyclohexyloxy)-7-chloro-2H-isoquinolin-1-one,
6-(trans-4-amino-4-cyclopropyl-cyclohexyloxy)-7-chloro-2H-isoquinolin-1-one,
6-(trans-4-amino-4-cyclopropyl-cyclohexyloxy)-7-methyl-2H-isoquinolin-1-one,
6-(cis-1-amino-bicyclohexyl-4-yloxy)-7-chloro-2H-isoquinolin-1-one,
6-(trans-1-amino-bicyclohexyl-4-yloxy)-7-chloro-2H-isoquinolin-1-one,
6-[cis-4-amino-4-(3-methoxy-propyl)-cyclohexyloxy]-7-chloro-2H-isoquinolin-1-one,
6-[trans-4-amino-4-(3-methoxy-propyl)-cyclohexyloxy]-7-chloro-2H-isoquinolin-1-one,
6-(trans-4-Benzylamino-4-cyclopropyl-cyclohexyloxy)-7-chloro-2H-isoquinolin-1-one,
7-chloro-6-(trans-4-cyclopropyl-4-isopropylamino-cyclohexyloxy)-2H-isoquinolin-1-one,
7-chloro-6-(4-cyclopropyl-4-ethylamino-cyclohexyloxy)-2H-isoquinolin-1-one,
6-[cis-4-Amino-4-(3-hydroxy-propyl)-cyclohexyloxy]-7-chloro-2H-isoquinolin-1-one,
6-[trans-4-amino-4-(3-hydroxy-propyl)-cyclohexyloxy]-7-chloro-2H-isoquinolin-1-one,
6-[4-amino-4-(2,3-dihydroxy-propyl)-cyclohexyloxy]-7-chloro-2H-isoquinolin-1-one,
6-[cis-4-Amino-4-(4-fluoro-phenyl)-cyclohexyloxy]-7-chloro-2H-isoquinolin-1-one,
6-(cis-4-Amino-4-phenyl-cyclohexyloxy)-7-chloro-2H-isoquinolin-1-one,
6-(trans-4-Amino-4-phenyl-cyclohexyloxy)-7-chloro-2H-isoquinolin-1-one,
6-[cis-4-Amino-4-(4-trifluoromethyl-phenyl)-cyclohexyloxy]-7-chloro-2H-isoquinolin-1-one,
6-[cis-4-Amino-4-(3,5-dimethyl-phenyl)-cyclohexyloxy]-7-chloro-2H-isoquinolin-1-one,
6-[cis-4-Amino-4-(3,5-dimethyl-phenyl)-cyclohexyloxy]-7-methyl-2H-isoquinolin-1-one,
6-[cis-4-Amino-difluoro-phenyl)-cyclohexyloxy]-7-chloro-2H-isoquinolin-1-one,
6-[cis-4-Amino-4-(2,6-difluoro-phenyl)-cyclohexyloxy]-7-chloro-2H-isoquinolin-1-one,
6-[cis-4-Amino-4-(2,6-difluoro-phenyl)-cyclohexyloxy]-7-methyl-2H-isoquinolin-1-one,
6-[cis-4-Amino-4-(4-fluoro-phenyl)-cyclohexyloxy]-7-methyl-2H-isoquinolin-1-one,
6-[cis-4-Amino-4-(2,4-difluoro-phenyl)-cyclohexyloxy]-7-methyl-2H-isoquinolin-1-one,
6-[cis-4-Amino-4-(2-fluoro-phenyl)-cyclohexyloxy]-7-chloro-2H-isoquinolin-1-one,
6-[cis-4-Amino-4-(2-fluoro-phenyl)-cyclohexyloxy]-7-methyl-2H-isoquinolin-1-one,
6-[cis-4-Amino-4-(3,5-dimethyl-phenyl)-cyclohexyloxy]-7-chloro-2H-isoquinolin-1-one, and
stereoisomeric form thereof and/or tautomeric form thereof and/or pharmaceutically acceptable salt thereof.

45. A pharmaceutical composition comprising a pharmaceutically effective amount of at least one compound according to claim 1 and/or a pharmacologically acceptable salt thereof, and physiologically tolerated excipient or carriers, and, optionally one or more additives and/or one or more other active compounds.

46. A pharmaceutical composition comprising a pharmaceutically effective amount of at least one compound according to claim 43 and/or a pharmacologically acceptable salt thereof, and physiologically tolerated excipient or carriers, and, optionally one or more additives and/or one or more other active compounds.

47. A pharmaceutical composition comprising a pharmaceutically effective amount of at least one compound according to claim 44 and/or a pharmacologically acceptable salt thereof, and physiologically tolerated excipient or carriers, and, optionally one or more additives and/or one or more other active compounds.

\* \* \* \* \*